US010221234B2

(12) United States Patent
Bhinder et al.

(10) Patent No.: US 10,221,234 B2
(45) Date of Patent: Mar. 5, 2019

(54) ANTIGEN BINDING PROTEINS

(71) Applicant: GLAXO GROUP LIMITED, Brentford, Middlesex (GB)

(72) Inventors: Tejinder Kaur Bhinder, Stevenage (GB); Susannah Karen Ford, Stevenage (GB); Volker Germaschewski, Stevenage (GB); Alan Peter Lewis, Stevenage (GB); Mark Brian Pepys, London (GB)

(73) Assignee: Glaxo Group Limited (GB)

( * ) Notice: Subject to any disclaimer, the term of this patent is extended or adjusted under 35 U.S.C. 154(b) by 0 days.

(21) Appl. No.: 15/229,155

(22) Filed: Aug. 5, 2016

(65) Prior Publication Data

US 2016/0333086 A1    Nov. 17, 2016

Related U.S. Application Data

(62) Division of application No. 13/037,505, filed on Mar. 1, 2011, now Pat. No. 9,434,716.

(60) Provisional application No. 61/309,957, filed on Mar. 3, 2010.

(51) Int. Cl.
| | | |
|---|---|---|
| *A61K 39/395* | (2006.01) | |
| *C07K 16/18* | (2006.01) | |
| *C07D 403/06* | (2006.01) | |
| *A61K 31/4025* | (2006.01) | |
| *A61K 39/00* | (2006.01) | |

(52) U.S. Cl.
CPC .......... *C07K 16/18* (2013.01); *A61K 31/4025* (2013.01); *A61K 39/3955* (2013.01); *C07D 403/06* (2013.01); *A61K 2039/505* (2013.01); *C07K 2317/24* (2013.01); *C07K 2317/33* (2013.01); *C07K 2317/34* (2013.01); *C07K 2317/54* (2013.01); *C07K 2317/56* (2013.01); *C07K 2317/565* (2013.01); *C07K 2317/567* (2013.01); *C07K 2317/70* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,429,192 B1 | 8/2002 | Laursen | |
| 6,750,324 B1 | 6/2004 | Schenk et al. | |
| 7,910,106 B2 * | 3/2011 | Pepys | A61K 31/401 424/145.1 |

FOREIGN PATENT DOCUMENTS

| | | |
|---|---|---|
| EP | 0 620 276 | 12/1990 |
| EP | 0 915 088 | 10/1998 |
| WO | WO 95/05394 | 2/1995 |
| WO | WO 2004/059318 | 7/2004 |
| WO | WO 2004/099173 | 11/2004 |
| WO | WO 2009/000926 | 12/2008 |
| WO | WO 2009/155962 | 12/2009 |

OTHER PUBLICATIONS

Alberts et al., Molecular Biology of the Cell 3rd edition, pp. 1216-1220.
Casset et al. (BBRC 2003, 307:198-205).
Chen et al. (J. Mol. Bio. (1999) 293, 865-881).
Duong, T., et al., Immunodetection of the amyloid component in Alzheimer's disease. Acta Neuropathol. 1989, 78:429-437.
Gewurz, A., et al., Monoclonal antibodies to human serum amyloid P-component. Amyloid P component. FASEB J. 4(7):A2198; Meeting abstract (1989).
Hazenberg BP, et al., Diagnostic performance of 1231-labled serum amyloid P component scintigraphy in patients with amyloidosis. Am. J. Med., Apr. 2006: 119(4):355.e15-24.
Kuby, Immunology 3rd edition, pp. 131-134.
Lamminmaki et al. (JBC 2001,276:36687-36694).
MacCallum et al. J. Mol. Biol. (1996) 262,732-745.
O'Sullivan, G., et al., Monoclonal antibodies to human serum amyloid P-component. Amyloid Amyloidosis 1990, 6th Int. Symp. Amyloidosis, pp. 906-910; Meeting abstract. (1991).
O'Sullivan, G., et al., Monoclonal antibodies to serum amyloid P component to define binding sites. Amyloid Amyloidosis 1993, 7th Proc. Int. Symp. Amyloidosis, pp. 186-188; Meeting abstract.
Padlan et al. (PNAS 1989, 86:5938-5942).
Pascal is et al. (The Journal of Immunology (2002) 169,3076-3084).
Rudikoff et al. (Proc Natl Acad Sci USA 1982 vol. 79 p. 1979).
Santa Cruz Biotechnology, Inc. Research Antibodies Catalog '07, entry for SAP (SAP-5) sc-59686, p. 576m, Jan. 2007.
Vajdos et al. (J. Mol. Biol. (2002) 320, 415-428).
Wu et al. (J. Mol. Biol. (1999) 294,151-162).
Ying, SC, et al., Reactivity of anti-human C.reactive protein (CRP) and serum amyloid P component (SAP) monoclonal antibodies with limulin and pentraxins of other species. Immunol 76:324-330 (1192).
Zandman-Goddard, G., et al., Anti-serum amyloid component P antibodies in patients with systemic lupus erythematosus correlate with disease activity. Ann. Rheum. Dis. 2005; 64:1698-1702.
Bodin, et al., Antibodies to human serum amyloid P. component eliminate visceral amyloid deposits, Nature, vol. 468, pp. 93-97, Nov. 4, 2010.
Gillmore, et al., Sustained pharmacological depletion of serum amyloid P. component in patients with systemic amyloidosis, British Journal of Haematology, vol. 148, pp. 760-767, Jan. 8, 2010.

(Continued)

*Primary Examiner* — Laura B Goddard
*Assistant Examiner* — Meera Natarajan
(74) *Attorney, Agent, or Firm* — Jason C. Fedon

(57) ABSTRACT

The present invention relates to antigen binding proteins, such as antibodies, which bind to serum amyloid P component (SAP), polynucleotides encoding such antigen binding proteins, pharmaceutical compositions comprising said antigen binding proteins and methods of manufacture. The present invention also concerns the use of such antigen binding proteins in the treatment or prophylaxis of diseases associated with amyloid deposition including systemic amyloidosis, local amyloidosis, Alzheimer's disease, and type 2 diabetes.

12 Claims, 9 Drawing Sheets

Specification includes a Sequence Listing.

(56) References Cited

OTHER PUBLICATIONS

Kolstoe, et al., Molecular dissection of Alzheimer's disease neuropathology by depletion of serum amyloid P. component, PNAS, vol. 106, No. 18, pp. 7619-7623, May 5, 2009.

Pepys, et al., Targeted phannacological depletion of serum amyloid P. component for treabnent of human amyloidosis, Nature, vol. 417, pp. 254-259, May 16, 2002.

* cited by examiner (A)

(B)

(C)

(D)

```
    136 140  147
h  EQDSYGGKFDRS
m  EQDNYGGGFQRS
```

(A)

(B)

(A)
-ve

+ve (B) Immunoblot probed with anti-mouse C3 at 1:5000
-ve

+ve (C) Immunoblot probed with anti-mouse C3 at 1:10000
-ve

+ve

ANTIGEN BINDING PROTEINS

FIELD OF INVENTION

The present invention relates to antigen binding proteins, such as antibodies, which bind to serum amyloid P component (SAP), polynucleotides encoding such antigen binding proteins, pharmaceutical compositions comprising said antigen binding proteins and methods of manufacture. The present invention also concerns the use of such antigen binding proteins in the treatment or prophylaxis of diseases associated with amyloid deposition including systemic amyloidosis, local amyloidosis, Alzheimer's disease, and type 2 diabetes.

BACKGROUND OF THE INVENTION

Amyloidosis is a serious and usually fatal disease caused by the extracellular accumulation in the tissues of abnormal insoluble protein fibres known as amyloid fibrils. These are derived from more than 20 different proteins in different forms of the disease but all amyloid fibrils share a common cross-β core structure and all are derived by misfolding of normally soluble precursor proteins (Pepys, M. B. (2006) Annu. Rev. Med., 57: 223-241). A normal non-fibrillar plasma protein, serum amyloid P component (SAP), is also always present in amyloid deposits by virtue of its avid specific calcium dependent binding to all types of amyloid fibrils (Pepys et al. (1979) Clin. Exp. Immunol., 38: 284-293; Pepys et al. (1997) Amyloid: Int. J. Exp. Clin. Invest., 4: 274-295).

Human SAP is a constitutive protein in the plasma, at a concentration of around 20-40 mg/l (Nelson et al. (1991) Clin. Chim. Acta, 200:191-200) and with a total of about 50-100 mg of SAP in the combined plasma and extravascular compartments both of normal individuals and patients with diseases other than amyloidosis (Hawkins et al. (1990) J. Clin. Invest., 86: 1862-1869). In patients with amyloidosis, SAP is also specifically concentrated in the amyloid deposits and in an individual with extensive systemic amyloidosis there may be as much as 20,000 mg of SAP in the amyloid (Pepys et al. (1994) PNAS, 91: 5602-5606), reversibly bound to the fibrils and in equilibrium with the fluid phase SAP pool. The normal physiological function of circulating SAP is poorly understood, but animal experiments and in vitro studies suggest a role in host defence (Noursadeghi et al. (2000) PNAS, 97: 14584-14589)). SAP is also a normal tissue matrix constituent associated with elastic fibres and the glomerular basement membrane although its function there is not known.

In amyloidosis, the extracellular amyloid deposits cause disease by progressive accumulation until they damage the structure and thus the function of whatever tissue they occupy (Pepys, M. B. (2006) Annu. Rev. Med., 57: 223-241). There is very rarely any inflammatory or 'foreign body' response to amyloid deposition, either seen locally in the tissues or suggested by systemic markers of inflammation. Systemic amyloidosis can involve any organ, is usually fatal and causes ~1 per thousand deaths in developed countries. Localised amyloid, confined to a single anatomical location or tissue type, can also be very serious, for example cerebral amyloid angiopathy is an important cause of haemorrhagic stroke. The clinical presentations of amyloidosis are extremely diverse and the diagnosis is rarely made before significant organ damage is present. Over 20 different amyloid fibril proteins are responsible for different forms of amyloidosis, but treatments that substantially reduce the abundance of the respective amyloid fibril precursor protein do halt amyloid accumulation and the deposits may regress. Unfortunately effective measures are not always available and, when they do exist, are toxic or hazardous and slow to act (Pepys, M. B (2006) Annu. Rev. Med., 57: 223-241). There is therefore a major unmet medical need for therapy which safely promotes the clearance of established amyloid deposits. Furthermore, there are other conditions in which amyloid deposits are always present, most importantly Alzheimer's disease (AD) and type 2 diabetes mellitus, in which the contribution of amyloid deposition to the pathogenesis of disease, specifically loss of cognitive and pancreatic islet function, respectively, is not known (Pepys, M. B. (2006) Annu. Rev. Med., 57: 223-241). However, amyloid deposits anywhere else in the body are demonstrably pathogenic and it is likely that the cerebral deposits of AD and the islet amyloid deposits of type 2 diabetes are also harmful. Since treatment which clears amyloid deposits in systemic amyloidosis will certainly be therapeutic (Pepys, M. B. (2006) Annu. Rev. Med., 57: 223-241), removal of the amyloid deposits in AD and type 2 diabetes should also be clinically beneficial.

Binding of SAP stabilises amyloid fibrils, protects them from proteolysis in vitro (Tennent et al., (1995) PNAS, 92: 4299-4303), can enhance amyloid fibrillogenesis in vitro (Myers et al., (2006), Biochemistry, 45: 2311-2321) and contributes to pathogenesis of systemic amyloidosis in vivo (Botto et al., (1997) Nature Med., 3: 855-859). Coupled with its universal presence in all amyloid deposits, these properties of SAP make it an attractive therapeutic target.

European patent application EP 0915088 discloses D-proline derivative compounds that are competitive inhibitors of binding of SAP to amyloid fibrils, as well as methods for their manufacture. A preferred compound disclosed in EP 0915088 is (R)-1-[6-[(R)-2-Carboxy-pyrrolidin-1-yl]-6-oxo oxohexanoyl] pyrrolidine-2-carboxylic acid (CPHPC).

International patent application WO 03/051836 discloses prodrugs for D-proline derivative compounds.

International patent application WO 2004/099173 discloses glycerol cyclic pyruvate derivatives that are competitive inhibitors of binding of SAP to amyloid fibrils.

International patent application WO 04/059318 describes methods which are asserted to enhance fibrocyte formation which comprise the provision of compositions which bind SAP. Such compositions include anti-SAP antibodies and CPHPC. WO 04/059318 does not disclose the treatment of disease associated with amyloid deposition. Furthermore, there is compelling clinical and in vivo evidence that neither SAP nor its depletion have any effect on fibrosis in humans (Tennent et al., (2007) Arthritis Rheum., 56: 2013-2017; Pepys, M. B., Tennent, G. A. and Denton, C. P. (2007) Reply to Letter from Pilling, D., Buckley, C. D., Salmon, M. and Gomer, R. G., Serum amyloid P and fibrosis in systemic sclerosis: comment on the article by Tennent et al. *Arthritis Rheum.*, 56: 4229-4230).

The bis-D-proline compound, CPHPC, disclosed in the patents listed above, is bound with high affinity by human SAP and was intended as a drug to remove SAP from amyloid deposits in vivo and thereby facilitate their clearance. Binding of CPHPC by SAP triggers rapid clearance of the complex by the liver, depletes almost all circulating SAP for as long as the drug is administered, and removes much but not all amyloid bound SAP (Pepys et al., (2002) Nature, 417: 254-259). In initial clinical studies (Gillmore et al., (2010) Brit. J. Haematol., doi:10.1111/j.1365-2141.2009.08036.x), administration of CPHPC seemed to arrest amyloid accumulation but it did not produce amyloid regression and since CPHPC does not completely remove all SAP from amyloid deposits, another approach is needed.

International patent application WO 2009/000926 discloses the use of compounds which deplete SAP from the circulation, such as D-proline derivatives, in particular CPHPC, in combination with an antibody specific for SAP for the treatment or prophylaxis of amyloidosis.

Related International patent application PCT/EP2008/011135 concerns various mouse monoclonal antibodies which may be used in combination with compounds which deplete SAP from the circulation, such as D-proline derivatives, in particular CPHPC, for the treatment or prophylaxis of amyloidosis.

Accordingly, there is a need in the art for antibodies, particularly humanised or human antibodies, which specifically target SAP and provide improved therapeutic efficacy in patients, particularly human patients, with diseases associated with amyloid deposition in order to preserve organ function and prolong life.

SUMMARY OF THE INVENTION

The present invention provides, in a first aspect, an antigen binding protein which specifically binds to SAP and competes for binding to SAP with a reference antibody which comprises a heavy chain variable region sequence of SEQ ID NO:7, and a light chain variable region sequence of SEQ ID NO:9.

In a second aspect of the invention, there is provided an antigen binding protein which binds to SAP and comprises CDRH3 set forth in SEQ ID NO: 3 or a functional variant of CDRH3.

In a third aspect of the invention, there is provided an antigen binding protein which specifically binds to SAP, wherein the antigen binding protein is a chimeric or a humanised antibody comprising the corresponding CDRH3 of the variable domain sequence of SEQ ID NO:7, or a functional variant of CDRH3.

In a fourth aspect of the invention, there is provided an antigen binding protein which specifically binds to SAP, and comprises a binding unit H3 comprising Kabat residues 95-101 of SEQ ID NO:7, or a functional variant of binding unit H3.

In a fifth aspect of the invention, there is provided an antigen binding protein which specifically binds to SAP and comprises a heavy chain variable region selected from SEQ ID NO:27-31; and/or a light chain variable region selected from SEQ ID NO:34-36; or a variant heavy chain variable region or light chain variable region with 75% or greater sequence identity.

In a sixth aspect of the invention, there is provided an antigen binding protein which specifically binds to SAP and comprises a heavy chain of SEQ ID NO:62; and/or a light chain of SEQ ID NO:64; or a variant heavy chain or light chain with 75% or greater sequence identity.

The present invention also provides a nucleic acid molecule encoding an antigen binding protein of the invention, expression vectors comprising the same, and host cells capable of producing antigen binding proteins of the invention.

In a further aspect of the invention a pharmaceutical composition comprising an antigen binding protein as defined herein is provided. The present invention also provides methods of preventing and/or treating a subject susceptible to or afflicted with a disease associated with amyloid deposition, which method comprises the step of administering a prophylactically or therapeutically effective amount of an antigen binding protein to said subject. The use of an antigen binding protein as defined herein for preventing and/or treating a subject susceptible to or afflicted with a disease associated with amyloid deposition is provided. The use of an antigen binding protein as defined herein for the manufacture of a medicament for preventing and/or treating a subject susceptible to or afflicted with a disease associated with amyloid deposition is also provided.

DETAILED DESCRIPTION OF THE INVENTION

Figure 1:
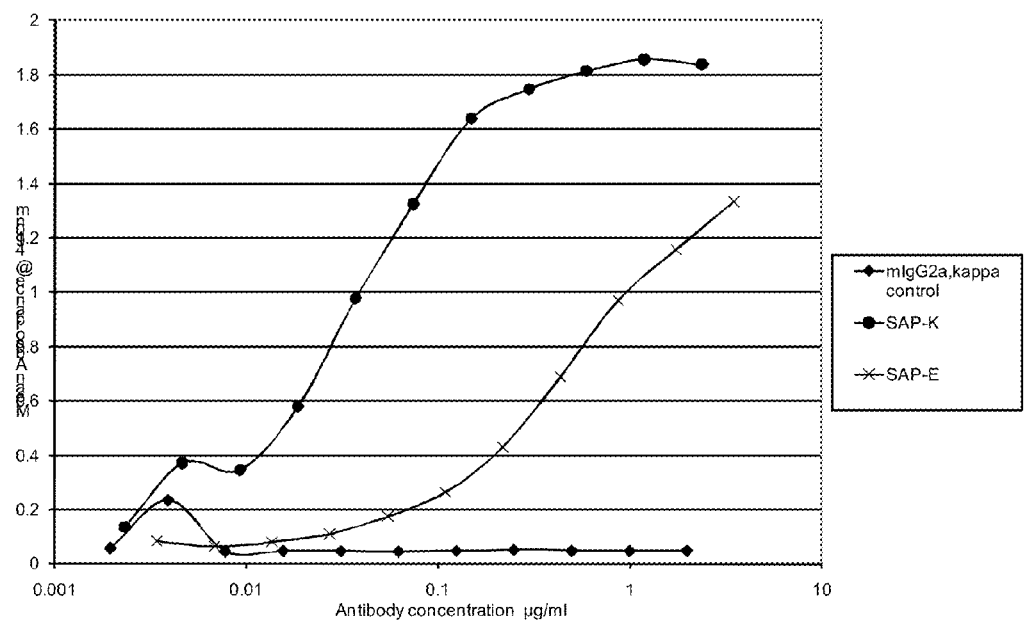
FIG. 1 shows the binding curves for murine antibodies SAP-E and SAP-K at a 1 µg/mL coating concentration of human SAP.

The present invention provides an antigen binding protein which binds to serum amyloid P component (SAP), for example human SAP, as its specific antigen (i.e. a SAP binding protein). In therapeutic applications of the invention, the antigen binding protein activates the body's potent mechanisms for clearance of abnormal debris from tissues. The antigen binding protein may be an antibody, for example a monoclonal antibody. An antigen binding protein of the invention is not a murine antibody. In an embodiment, an antigen binding protein of the invention is not a murine antigen binding protein. In particular, an antigen binding protein of the invention is a chimeric, humanised or human antigen binding protein.

"Serum amyloid P component" or "SAP" refers to a homopentameric plasma glycoprotein of the pentraxin family. Each molecule is composed of 5 identical protomers, each with a flattened β-jelly roll fold and single alpha helix, non-covalently associated in a disc-like ring with cyclic pentameric symmetry (Hutchinson et al., (2000) Mol. Med., 6: 482-493); Pepys et al., (2002) Nature, 417: 254-259). The term "SAP" as used herein also includes the individual subunit encoded by the human gene APCS (chromosome: 1; Location: 1q21-q23) or homologous genes in other organisms, for example the human SAP polypeptide subunit having the sequence as set forth in SEQ ID NO:43 as well as the native pentameric form of SAP, and any fragments and variants of SAP that retain the biological activity of binding to amyloid fibrils in vivo.

The SAP binding protein of the invention can bind to any one or any combination of the above described different forms of SAP. In a particular embodiment, the antigen binding protein of the invention binds human SAP. The SAP binding protein of the invention can bind to SAP when the SAP is bound to amyloid fibrils of any type and in any extracellular location within the body. The antigen binding protein of the invention may also bind to native unbound SAP.

An essential aspect of utilising SAP-binding proteins of the invention in therapeutic methods is that the concentration of SAP in the circulation must be reduced by at least 90% below its normal value before administration of the SAP-binding protein. Specifically, this can be achieved by compounds that decrease the amount of circulating SAP and, in particular, compounds that result in the depletion of circulating SAP, defined here as "SAP depleting compounds". Such compounds are ligands bound by SAP and are competitive inhibitors of the binding of SAP to amyloid fibrils, such as D-proline derivatives and glycerol cyclic pyruvate derivatives. D-proline derivatives are disclosed in EP 0915088, which is incorporated herein by reference in its entirety, and the term "D-proline derivatives" includes prodrugs, such as those disclosed in WO 03/051836, which is also incorporated herein by reference in its entirety. D-prolines of the following formula are contemplated:

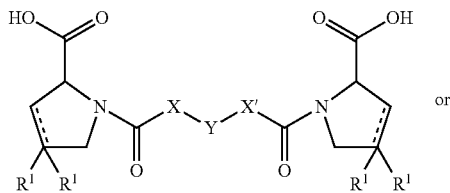

I-A

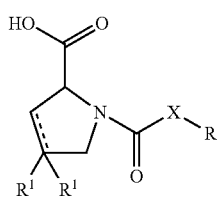

I-B wherein
R is

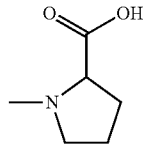

and the group
R$^1$ is hydrogen or halogen;
and
X is —(CH$_2$)$_n$—; —CH(R$^2$)(CH$_2$)$_n$—; —CH$_2$O(CH$_2$)$_n$—; —CH$_2$NH—; —C(R$^2$)=CH—; —CH$_2$CH(OH)—; or thiazol-2,5-diyl; —O—;
Y is —S—S—; —(CH$_2$)$_n$—; —O—; —NH—; —N(R$^2$)—; —CH=CH—; —NHC(O)NH—; —N(R$^2$)C(O)N(R$^2$)—; —N[CH$_2$C$_6$H$_3$(OCH$_3$)$_2$]—; —N(CH$_2$C$_6$H$_5$)—; —N(CH$_2$C$_6$H$_5$)C(O)N(CH$_2$C$_6$H$_5$)—; —N(alkoxyalkyl)-; N(cycloalkylmethyl)-; 2,6-pyridyl; 2,5-furanyl; 2,5-thienyl; 1,2-cyclohexyl; 1,3-cyclohexyl; 1,4-cyclohexyl; 1,2-naphthyl; 1,4-naphthyl; 1,5-naphthyl; 1,6-naphthyl; or 1,2-phenylene, 1,3-phenylene and 1,4-phenylene, wherein the phenylene groups are optionally substituted by 1-4 substituents, selected from halogen, lower alkyl, lower alkoxy, hydroxyl, carboxy, —COO-lower alkyl, nitrilo, 5-tetrazol, (2-carboxylic acid pyrrolidin-1-yl)-2-oxo-ethoxy, N-hydroxycarbamimiodyl, 5-oxo [1,2,4oxadiazolyl, 2-oxo [1,2,3,5] oxathiadiazolyl, 5-thioxo[1,2,4]oxadiazolyl and 5-tert-butylsulfanyl-[1,2,4]oxadiazolyl;
X' is —(CH$_2$)$_n$—; —(CH$_2$)$_n$CH(R$_2$)—; —(CH$_2$)$_n$OCH$_2$—; —NHCH$_2$—; —CH=C(R$^2$)—; CH(OH)CH$_2$—; or thiazol-2,5-diyl; —O—;
R$^2$ is lower alkyl, lower alkoxy or benzyl,
n is 0-3 and wherein
alkyl or lower alkyl is C$_{1-6}$ alkyl; alkoxy or lower alkoxy is C$_{1-6}$ alkoxy; cycloalkyl is C$_{3-6}$ cyclocalkyl; halogen is F, Cl or Br; and the location where the dotted line appears in the formula is either a single or double bond; or a pharmaceutically acceptable salt or mono- or diester thereof.

D-prolines of formula I-A above can be written as Ligand-linker-Ligand, wherein the X—Y—X' moiety of formal I-A forms the linker. The linker (X—Y—X') can be from 4 to 20 linear carbon atoms in length, including from 4-15 linear carbon atoms, 5-10 linear carbon atoms, and 6-8 linear carbon atoms in length. The linker can be a straight or branched chain, or can optionally form one or more ring structures, with the proviso that at least 4 linear or straight-chain carbon atoms are present in the linker. At least one of the linear or straight-chain C atoms can be optionally substituted by at least one hetero atom selected from N, O, or S, advantageously O or S, advantageously O.

Thus, an "optionally substituted linker" can have one or more substitutions that lead to branching and/or one or more substitutions of carbon atom(s) of the linear or straight chain carbon atoms of the linker, e.g. the linker can be an ether or a substituted ether.

(R)-1-[6-[(R)-2-Carboxy-pyrrolidin-1-yl]-6-oxo-hexanoyl]pyrrolidine-2-carboxylic acid (CPHPC) is a specific D-proline contemplated by the invention. In a particular embodiment, CPHPC is to be administered to a human patient.

Gylcerol cyclic pyruvate derivatives are disclosed in WO 2004/099173, which is incorporated herein by reference in its entirety.

The term "antigen binding protein" as used herein refers to antibodies, antibody fragments and other protein constructs, such as domains, which are capable of binding to SAP.

The term "antibody" is used herein in the broadest sense to refer to molecules with an immunoglobulin-like domain and includes monoclonal, recombinant, polyclonal, chimeric, humanised, bispecific and heteroconjugate antibodies; a single variable domain, a domain antibody, antigen binding fragments, immunologically effective fragments, single chain Fv, diabodies, Tandabs™, etc. (for a summary of alternative "antibody" formats see Holliger and Hudson, Nature Biotechnology, 2005, Vol 23, No. 9, 1126-1136).

The phrase "single variable domain" refers to an antigen binding protein variable domain (for example, VH, VHH, VL) that specifically binds an antigen or epitope independently of a different variable region or domain.

A "domain antibody" or "dAb" may be considered the same as a "single variable domain" which is capable of binding to an antigen. A single variable domain may be a human antibody variable domain, but also includes single antibody variable domains from other species such as rodent (for example, as disclosed in WO 00/29004), nurse shark and Camelid VHH dAbs. Camelid VHH are immunoglobulin single variable domain polypeptides that are derived from species including camel, llama, alpaca, dromedary, and guanaco, which produce heavy chain antibodies naturally devoid of light chains. Such VHH domains may be humanised according to standard techniques available in the art, and such domains are considered to be "domain antibodies". As used herein VH includes camelid VHH domains.

As used herein the term "domain" refers to a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A domain can bind an antigen or epitope independently of a different variable region or domain.

An antigen binding fragment may be provided by means of arrangement of one or more CDRs on non-antibody protein scaffolds such as a domain. The domain may be a domain antibody or may be a domain which is a derivative of a scaffold selected from the group consisting of CTLA-4, lipocalin, SpA, an Affibody, an avimer, GroEI, transferrin, GroES and fibronectin/adnectin, which has been subjected to protein engineering in order to obtain binding to an antigen, such as SAP, other than the natural ligand.

An antigen binding fragment or an immunologically effective fragment may comprise partial heavy or light chain variable sequences. Fragments are at least 5, 6, 7, 8, 9 or 10 amino acids in length. Alternatively the fragments are at least 15, at least 20, at least 50, at least 75, or at least 100 amino acids in length.

The term "specifically binds" as used throughout the present specification in relation to antigen binding proteins means that the antigen binding protein binds to SAP with no or insignificant binding to any other proteins, including closely related molecules such as C-reactive protein (CRP) which, in humans, shares 55% of strict residue for residue amino acid sequence homology and has essentially the same protein fold.

The equilibrium dissociation constant (KD) of the antigen binding protein-SAP interaction may be 1 mM or less, 100 nM or less, 10 nM or less, 2 nM or less or 1 nM or less. Alternatively the KD may be between 5 and 10 nM; or between 1 and 2 nM. The KD may be between 1 pM and 500 pM; or between 500 pM and 1 nM.

The binding affinity may be measured by BIAcore™, for example by antigen capture with SAP coupled onto a carboxymethydextran chip by primary amine coupling and antibody capture onto this surface. Alternatively, the binding affinity can be measured by BIAcore™ by binding of anti-SAP antibodies to human SAP captured by O-phosphoethanolamine immobilised on a CM5 chip. The BIAcore™ methods described in Example 8 may be used to measure binding affinity.

The dissociation rate constant (kd) may be $1 \times 10^{-3}$ s$^{-1}$ or less, $1 \times 10^{-4}$ s$^{-1}$ or less, or $1 \times 10^{-5}$ s$^{-1}$ or less. The kd may be between $1 \times 10^{-5}$ s$^{-1}$ and $1 \times 10^{-4}$ s$^{-1}$; or between $1 \times 10^{-4}$ s$^{-1}$ and $1 \times 10^{-3}$ s$^{-1}$. A small kd may result in a slow dissociation of the antigen binding protein-ligand complex and improved clearance of complexes of SAP bound to amyloid.

It will be apparent to those skilled in the art that the term "derived" is intended to define not only the source in the sense of it being the physical origin for the material but also to define material which is structurally identical to the material but which does not originate from the reference source. Thus "residues found in the donor antibody" need not necessarily have been purified from the donor antibody.

By "isolated" it is intended that the molecule, such as an antigen binding protein, is removed from the environment in which it may be found in nature. For example, the molecule may be purified away from substances with which it would normally exist in nature. For example, the mass of the molecule in a sample may be 95% of the total mass.

A "chimeric antibody" refers to a type of engineered antibody which contains a naturally-occurring variable region (light chain and heavy chains) derived from a donor antibody in association with light and heavy chain constant regions derived from an acceptor antibody.

A "humanised antibody" refers to a type of engineered antibody having its CDRs derived from a non-human donor immunoglobulin, the remaining immunoglobulin-derived parts of the molecule being derived from one or more human immunoglobulin(s). In addition, framework support residues may be altered to preserve binding affinity (see, e.g., Queen et al. Proc. Natl Acad Sci USA, 86:10029-10032 (1989), Hodgson et al. Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanised antibodies—see for example EP-A-0239400 and EP-A-054951.

The term "donor antibody" refers to an antibody which contributes the amino acid sequences of its variable regions, CDRs, or other functional fragments or analogs thereof to a first immunoglobulin partner. The donor therefore provides the altered immunoglobulin coding region and resulting expressed altered antibody with the antigenic specificity and neutralising activity characteristic of the donor antibody.

The term "acceptor antibody" refers to an antibody which is heterologous to the donor antibody, which contributes all (or any portion) of the amino acid sequences encoding its heavy and/or light chain framework regions and/or its heavy and/or light chain constant regions to the first immunoglobulin partner. A human antibody may be the acceptor antibody.

The term "human antibody" refers to an antibody derived from human immunoglobulin gene sequences. These fully human antibodies provide an alternative to re-engineered, or de-immunized, rodent monoclonal antibodies (e.g. humanised antibodies) as a source of low immunogenicity therapeutic antibodies and they are normally generated using either phage display or transgenic mouse platforms. In an embodiment, an antibody of the invention is a human antibody.

The terms "VH" and "VL" are used herein to refer to the heavy chain variable region and light chain variable region respectively of an antigen binding protein.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

Throughout this specification, amino acid residues in variable domain sequences and full length antibody sequences are numbered according to the Kabat numbering convention. Similarly, the terms "CDR", "CDRL1", "CDRL2", "CDRL3", "CDRH1", "CDRH2", "CDRH3" used in the Examples follow the Kabat numbering convention. For further information, see Kabat et al., Sequences of Proteins of Immunological Interest, 4th Ed., U.S. Department of Health and Human Services, National Institutes of Health (1987).

However, although we use the Kabat numbering convention for amino acid residues in variable domain sequences and full length antibody sequences throughout this specification, it will be apparent to those skilled in the art that there are alternative numbering conventions for amino acid residues in variable domain sequences and full length antibody sequences. There are also alternative numbering conventions for CDR sequences, for example those set out in Chothia et al. (1989) Nature 342: 877-883. The structure and protein folding of the antibody may mean that other residues are considered part of the CDR sequence and would be understood to be so by a skilled person.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Table 1 below represents one definition using each numbering convention for each CDR or binding unit. The Kabat numbering scheme is used in Table 1 to number the variable domain amino acid sequence. It should be noted that some of the CDR definitions may vary depending on the individual publication used.

TABLE 1

|  | Kabat CDR | Chothia CDR | AbM CDR | Contact CDR | Minimum binding unit |
|---|---|---|---|---|---|
| H1 | 31-35/35A/35B | 26-32/33/34 | 26-35/35A/35B | 30-35/35A/35B | 31-32 |
| H2 | 50-65 | 52-56 | 50-58 | 47-58 | 52-56 |
| H3 | 95-102 | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

As used herein, the term "antigen binding site" refers to a site on an antigen binding protein which is capable of specifically binding to an antigen. This may be a single domain (for example, an epitope-binding domain), or single-chain Fv (ScFv) domains or it may be paired VH/VL domains as can be found on a standard antibody.

The term "epitope" as used herein refers to that portion of the antigen that makes contact with a particular binding domain of the antigen binding protein. An epitope may be linear, comprising an essentially linear amino acid sequence from the antigen. Alternatively, an epitope may be conformational or discontinuous. For example, a conformational epitope comprises amino acid residues which require an element of structural constraint. In the case of a conformational epitope, although the residues may be from different regions of the peptide chain, they may be in close proximity in the three dimensional structure of the antigen. In the case of multimeric antigens, such as SAP, a conformational epitope may include residues from different peptide chains that may be in close proximity in the three dimensional structure of the antigen. Such structurally neighbouring residues can be determined through computer modelling programs or via three-dimensional structures obtained through methods known in the art, such as X-ray crystallography.

A discontinuous epitope comprises amino acid residues that are separated by other sequences, i.e. not in a continuous sequence in the antigen's primary sequence. In the context of the antigen's tertiary and quaternary structure, the residues of a discontinuous epitope are near enough to each other to be bound by an antigen binding protein.

In an embodiment, an antigen binding protein of the invention binds to an epitope within residues 140-158 of human SAP.

For nucleotide and amino acid sequences, the term "identical" or "sequence identity" indicates the degree of identity between two nucleic acid or two amino acid sequences when optimally aligned and compared with appropriate insertions or deletions.

The percent identity between two sequences is a function of the number of identical positions shared by the sequences (i.e., % identity=number of identical positions/total number of positions multiplied by 100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

By way of example, a polynucleotide sequence may be identical to a reference polynucleotide sequence as described herein (see for example SEQ ID NO:8, 10, 18, 20, 45-48, 51-61, 63, 65-73), that is be 100% identical, or it may include up to a certain integer number of nucleotide alterations as compared to the reference sequence, such as at least 50, 60, 70, 75, 80, 85, 90, 95, 96, 97, 98, or 99% identical. Such alterations are selected from at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference polynucleotide sequence as described herein (see for example SEQ ID NO:8, 10, 18, 20, 45-48, 51-61, 63, 65-73), by the numerical percent of the respective percent identity (divided by 100) and subtracting that product from said total number of nucleotides in the reference polynucleotide sequence as described herein (see for example SEQ ID NO:8, 10, 18, 20, 45-48, 51-61, 63, 65-73), or:

$$n_n \leq x_n - (x_n \cdot y),$$

wherein $n_n$ is the number of nucleotide alterations, $x_n$ is the total number of nucleotides in the reference polynucleotide sequence as described herein (see for example SEQ ID NO:8, 10, 18, 20, 45-48, 51-61, 63, 65-73), and y is 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99% or 1.00 for 100%, · is the symbol for the multiplication operator, and wherein any non-integer product of $x_n$ and y is rounded down to the nearest integer prior to subtracting it from $x_n$.

Similarly, a polypeptide sequence may be identical to a polypeptide reference sequence as described herein (see for example SEQ ID NO:1-7, 9, 11-17, 19, 21-24, 27-31, 34-42, 62, 64, 74), that is be 100% identical, or it may include up to a certain integer number of amino acid alterations as compared to the reference sequence such that the % identity is less than 100%, such as at least 50, 60, 70, 75, 80, 85, 90, 95, 96, 97, 98, or 99% identical. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the polypeptide sequence encoded by the polypeptide reference sequence as described herein (see for example SEQ ID NO:1-7, 9, 11-17, 19, 21-24, 27-31, 34-42, 62, 64, 74) by the numerical percent of the respective percent identity (divided by 100) and then subtracting that product from said total number of amino acids in the polypeptide reference sequence as described herein (see for example SEQ ID NO:1-7, 9, 11-17, 19, 21-24, 27-31, 34-42, 62, 64, 74), or:

$$n_a \leq x_a - (x_a \cdot y),$$

wherein $n_a$ is the number of amino acid alterations, $x_a$ is the total number of amino acids in the reference polypeptide sequence as described herein (see for example SEQ ID NO:1-7, 9, 11-17, 19, 21-24, 27-31, 34-42, 62, 64, 74), and y is, 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99%, or 1.00 for 100%, · is the symbol for the multiplication operator, and wherein any non-integer product of $x_a$ and y is rounded down to the nearest integer prior to subtracting it from $x_a$.

The % identity may be determined across the length of the sequence.

The terms "peptide", "polypeptide" and "protein" each refers to a molecule comprising two or more amino acid residues. A peptide may be monomeric or polymeric.

It is well recognised in the art that certain amino acid substitutions are regarded as being "conservative". Amino acids are divided into groups based on common side-chain properties and substitutions within groups that maintain all or substantially all of the binding affinity of the antigen binding protein are regarded as conservative substitutions, see Table 2 below:

TABLE 2

| Side chain | Members |
| --- | --- |
| Hydrophobic | Met, Ala, Val, Leu, Ile |
| Neutral hydrophilic | Cys, Ser, Thr |
| Acidic | Aap, Glu |
| Basic | Asn, Gln, His, Lys, Arg |
| Residues that influence chain orientation | Gly, Pro |
| Aromatic | Trp, Tyr, Phe |

The antigen binding protein may compete for binding to SAP with a reference antibody comprising a heavy chain variable region sequence of SEQ ID NO: 7, and a light chain variable region sequence of SEQ ID NO: 9. Alternatively, the antigen binding protein may compete for binding to SAP with a reference antibody comprising a heavy chain variable region sequence of SEQ ID NO: 17, and a light chain variable region sequence of SEQ ID NO: 19.

Competition between the antigen binding protein and the reference antibody may be determined by competition ELISA, FMAT or BIAcore. A competing antigen binding protein may bind to the same epitope, an overlapping epitope, or an epitope in close proximity of the epitope to which the reference antibody binds.

The present invention also provides an antigen binding protein which specifically binds to SAP and comprises CDRH3 of SEQ ID NO:3 or a variant CDR thereof. The antigen binding protein may further comprise one or more CDRs, or all CDRs, in any combination, selected from: CDRH1 (SEQ ID NO:1), CDRH2 (SEQ ID NO:2), CDRL1 (SEQ ID NO:4), CDRL2 (SEQ ID NO:5), and CDRL3 (SEQ ID NO:6); or a variant thereof.

For example, the antigen binding protein may comprise CDRH3 (SEQ ID NO:3) and CDRH1 (SEQ ID NO:1), or variants thereof. The antigen binding protein may comprise CDRH3 (SEQ ID NO:3) and CDRH2 (SEQ ID NO:2), or variants thereof. The antigen binding protein may comprise CDRH1 (SEQ ID NO:1) and CDRH2 (SEQ ID NO:2), and CDRH3 (SEQ ID NO:3), or variants thereof.

The antigen binding protein may comprise CDRL1 (SEQ ID NO:4) and CDRL2 (SEQ ID NO:5), or variants thereof. The antigen binding protein may comprise CDRL2 (SEQ ID NO:5) and CDRL3 (SEQ ID NO:6), or variants thereof. The antigen binding protein may comprise CDRL1 (SEQ ID NO:4), CDRL2 (SEQ ID NO:5) and CDRL3 (SEQ ID NO:6), or variants thereof.

The antigen binding protein may comprise CDRH3 (SEQ ID NO:3) and CDRL3 (SEQ ID NO:6), or variants thereof. The antigen binding protein may comprise CDRH3 (SEQ ID NO:3), CDRH2 (SEQ ID NO:2) and CDRL3 (SEQ ID NO:6), or variants thereof. The antigen binding protein may comprise CDRH3 (SEQ ID NO:3), CDRH2 (SEQ ID NO:2), CDRL2 (SEQ ID NO:5) and CDRL3 (SEQ ID NO:6), or variants thereof.

The antigen binding protein may comprise CDRH1 (SEQ ID NO:1), CDRH2 (SEQ ID NO:2), CDRH3 (SEQ ID NO:3), CDRL1 (SEQ ID NO:4), CDRL2 (SEQ ID NO:5) and CDRL3 (SEQ ID NO:6), or variants thereof.

The present invention also provides an antigen binding protein which specifically binds to SAP and comprises CDRH3 of SEQ ID NO:13 or a variant CDR thereof. The antigen binding protein may further comprise one or more CDRs, or all CDRs, in any combination, selected from: CDRH1 (SEQ ID NO:11), CDRH2 (SEQ ID NO:12), CDRL1 (SEQ ID NO:14), CDRL2 (SEQ ID NO:15), and CDRL3 (SEQ ID NO:16); or a variant thereof.

The present invention also provides an antigen binding protein which specifically binds to SAP, wherein the antigen binding protein is a chimeric or a humanised antibody comprising the corresponding CDRH3 of the variable domain sequence of SEQ ID NO:7, or a variant CDRH3.

The chimeric or humanised antigen binding protein may further comprise one or more, or all of the corresponding CDRs selected from the variable domain sequence of SEQ ID NO:7 or SEQ ID NO:9, or a variant CDR thereof.

For example, the antigen binding protein may comprise corresponding CDRH3 and corresponding CDRH1, or variants thereof. The antigen binding protein may comprise corresponding CDRH3 and corresponding CDRH2, or variants thereof. The antigen binding protein may comprise corresponding CDRH1, corresponding CDRH2, and corresponding CDRH3; or variants thereof.

The antigen binding protein may comprise corresponding CDRL1 and corresponding CDRL2, or variants thereof. The antigen binding protein may comprise corresponding CDRL2 and corresponding CDRL3, or variants thereof. The antigen binding protein may comprise corresponding CDRL1, corresponding CDRL2 and corresponding CDRL3, or variants thereof.

The antigen binding protein may comprise corresponding CDRH3 and corresponding CDRL3, or variants thereof. The antigen binding protein may comprise corresponding CDRH3, corresponding CDRH2 and corresponding CDRL3, or variants thereof. The antigen binding protein may comprise corresponding CDRH3, corresponding CDRH2, corresponding CDRL2 and corresponding CDRL3, or variants thereof.

The antigen binding protein may comprise corresponding CDRH1, corresponding CDRH2, corresponding CDRH3, corresponding CDRL1, corresponding CDRL2 and corresponding CDRL3, or variants thereof.

The corresponding CDRs can be defined by reference to Kabat (1987), Chothia (1989), AbM or contact methods, or a combination of these methods. One definition of each of the methods can be found at Table 1 and can be applied to the reference heavy chain variable domain SEQ ID NO:7 and the reference light chain variable domain SEQ ID NO:9 to determine the corresponding CDR.

The present invention also provides an antigen binding protein which specifically binds to SAP, wherein the antigen binding protein is a chimeric or a humanised antibody comprising the corresponding CDRH3 of the variable domain sequence of SEQ ID NO:17, or a variant CDRH3.

The chimeric or humanised antigen binding protein may further comprise one or more, or all of the corresponding CDRs selected from the variable domain sequence of SEQ ID NO:17 or SEQ ID NO:19, or a variant CDR thereof.

The present invention also provides an antigen binding protein which specifically binds to SAP, and comprises a binding unit H3 comprising Kabat residues 95-101 of SEQ ID NO:7, or a variant H3. The antigen binding protein may further comprise one or more or all binding units selected from: H1 comprising Kabat residues 31-32 of SEQ ID NO:7, H2 comprising Kabat residues 52-56 of SEQ ID NO:7, L1 comprising Kabat residues 30-34 of SEQ ID NO:9, L2 comprising Kabat residues 50-55 of SEQ ID NO:9 and L3 comprising Kabat residues 89-96 of SEQ ID NO:9; or a variant binding unit.

For example, the antigen binding protein may comprise a binding unit H3 and a binding unit H1, or variants thereof. The antigen binding protein may comprise a binding unit H3 and a binding unit H2, or variants thereof. The antigen binding protein may comprise a binding unit H1, a binding unit H2, and a binding unit H3; or variants thereof.

The antigen binding protein may comprise a binding unit L1 and a binding unit L2, or variants thereof. The antigen binding protein may comprise a binding unit L2 and a binding unit L3, or variants thereof. The antigen binding protein may comprise a binding unit L1, a binding unit L2, and a binding unit L3; or variants thereof.

The antigen binding protein may comprise a binding unit H3 and a binding unit L3, or variants thereof. The antigen binding protein may comprise a binding unit H3, a binding unit H2, and a binding unit L3; or variants thereof. The antigen binding protein may comprise a binding unit H3, a binding unit H2, a binding unit L2, and a binding unit L3; or variants thereof.

The antigen binding protein may comprise a binding unit H1, a binding unit H2, a binding unit H3, a binding unit L1, a binding unit L2, and a binding unit L3; or variants thereof.

The present invention also provides an antigen binding protein which specifically binds to SAP, and comprises a binding unit H3 comprising Kabat residues 95-101 of SEQ ID NO:17, or a variant H3. The antigen binding protein may further comprise one or more or all binding units selected from: H1 comprising Kabat residues 31-32 of SEQ ID NO:17, H2 comprising Kabat residues 52-56 of SEQ ID NO:17, L1 comprising Kabat residues 30-34 of SEQ ID NO:19, L2 comprising Kabat residues 50-55 of SEQ ID NO:19 and L3 comprising Kabat residues 89-96 of SEQ ID NO:19; or a variant binding unit.

A CDR variant or variant binding unit includes an amino acid sequence modified by at least one amino acid, wherein said modification can be chemical or a partial alteration of the amino acid sequence (for example by no more than 10 amino acids), which modification permits the variant to retain the biological characteristics of the unmodified sequence. For example, the variant is a functional variant which specifically binds to SAP and activates clearance of complexes of SAP bound to amyloid from tissues. A partial alteration of the CDR amino acid sequence may be by deletion or substitution of one to several amino acids, or by addition or insertion of one to several amino acids, or by a combination thereof (for example by no more than 10 amino acids). The CDR variant or binding unit variant may contain 1, 2, 3, 4, 5 or 6 amino acid substitutions, additions or deletions, in any combination, in the amino acid sequence. The CDR variant or binding unit variant may contain 1, 2 or 3 amino acid substitutions, insertions or deletions, in any combination, in the amino acid sequence. The substitutions in amino acid residues may be conservative substitutions, for example, substituting one hydrophobic amino acid for an alternative hydrophobic amino acid. For example leucine may be substituted with valine, or isoleucine.

One or more of the CDRs, corresponding CDRs, variant CDRs or binding units described herein may be present in the context of a human framework, for example as a humanised or chimeric variable domain. Fully human antibodies comprising one or more of the CDRs, corresponding CDRs, variant CDRs or binding units described herein are also contemplated and are within the scope of the invention.

The CDRs L1, L2, L3, H1 and H2 tend to structurally exhibit one of a finite number of main chain conformations. The particular canonical structure class of a CDR is defined by both the length of the CDR and by the loop packing, determined by residues located at key positions in both the CDRs and the framework regions (structurally determining residues or SDRs). Martin and Thornton (1996; J Mol Biol 263:800-815) have generated an automatic method to define the "key residue" canonical templates. Cluster analysis is used to define the canonical classes for sets of CDRs, and canonical templates are then identified by analysing buried hydrophobics, hydrogen-bonding residues, and conserved glycines and prolines. The CDRs of antibody sequences can be assigned to canonical classes by comparing the sequences to the key residue templates and scoring each template using identity or similarity matrices.

Examples of CDR canonicals within the scope of the invention are given below. The amino acid numbering used is Kabat.

Examples of canonicals for CDRH1 as set out in SEQ ID NO:1, a variant thereof, the CDRH1 of SEQ ID NO:7 or a corresponding CDR are: Tyr 32 is substituted for Ile, His, Phe, Thr, Asn, Cys, Glu or Asp; Asn 33 is substituted for Tyr, Ala, Trp, Gly, Thr, Leu or Val; Met 34 is substituted for Ile, Val or Trp; and/or His 35 is substituted for Glu, Asn, Gin, Ser, Tyr or Thr.

Examples of canonicals for CDRH2 as set out in SEQ ID NO:2, a variant thereof, the CDRH2 of SEQ ID NO:7 or a corresponding CDR are: Tyr 50 is substituted for Arg, Glu, Trp, Gly, Gin, Val, Leu, Asn, Lys or Ala; Ile51 is substituted for Leu, Val, Thr, Ser or Asn; Tyr 52 is substituted for Asp, Leu, Asn or Ser; Gly 53 is substituted for Ala, Tyr, Ser, Lys, Thr or Asn; Asp 54 is substituted for Asn, Ser, Thr, Lys or Gly; Asn 56 is substituted for Tyr, Arg, Glu, Asp, Gly, Val, Ser or Ala; and/or Asn 58 is substituted for Lys, Thr, Ser, Asp, Arg, Gly, Phe or Tyr.

Examples of canonicals for CDRH3 as set out in SEQ ID NO:3, a variant thereof, the CDRH3 of SEQ ID NO:7 or a corresponding CDR are: Ser 102 is substituted for Tyr, His, Val, Ile, Asp or Gly.

Examples of canonicals for CDRL1 as set out in SEQ ID NO:4, a variant thereof, the CDRL1 of SEQ ID NO:9 or a corresponding CDR are: Asn 28 is substituted for Ser, Asp, Thr or Glu; Ile 29 is substituted for Val; Tyr 30 is substituted for Asp, Leu, Val, Ile, Ser, Asn, Phe, His, Gly or Thr; Ser 31 is substituted for Asn, Thr, Lys or Gly; Tyr 32 is substituted for Phe, Asn, Ala, His, Ser or Arg; Leu 33 is substituted for Met, Val, Ile or Phe; and/or Ala 34 is substituted for Gly, Asn, Ser, His, Val or Phe.

Examples of canonicals for CDRL2 as set out in SEQ ID NO:5, a variant thereof, the CDRL1 of SEQ ID NO:9 or a corresponding CDR are: Ala 51 is substituted for Thr, Gly or Val.

Examples of canonicals for CDRL3 as set out in SEQ ID NO:6, a variant thereof, the CDRL1 of SEQ ID NO:9 or a corresponding CDR are: Gln 89 is substituted for Ser, Gly, Phe or Leu; His 90 is substituted for Gln or Asn; His 91 is substituted for Asn, Phe, Gly, Ser, Arg, Asp, Thr, Tyr or Val; Tyr 92 is substituted for Asn, Trp, Thr, Ser, Arg, Gin, His, Ala or Asp; Gly 93 is substituted for Glu, Asn, His, Thr, Ser, Arg or Ala; Ala 94 is substituted for Asp, Tyr, Thr, Val, Leu, His, Asn, Ile, Trp, Pro or Ser; and/or Leu 96 is substituted for Pro, Tyr, Arg, Ile, Trp or Phe.

Examples of canonicals for CDRH1 as set out in SEQ ID NO:11, a variant thereof, the CDRH1 of SEQ ID NO:17 or a corresponding CDR are: Tyr 32 is substituted for Ile, His, Phe, Thr, Asn, Cys, Glu or Asp; Trp 33 is substituted for Tyr, Ala, Gly, Thr, Leu or Val; Met 34 is substituted for Ile, Val or Trp; and/or His 35 is substituted for Glu, Asn, Gin, Ser, Tyr or Thr.

Examples of canonicals for CDRH2 as set out in SEQ ID NO:12, a variant thereof, the CDRH1 of SEQ ID NO:17 or a corresponding CDR are: Met 50 is substituted for Arg, Glu, Trp, Tyr, Gly, Gin, Val, Leu, Asn, Lys or Ala; Ile51 is substituted for Leu, Val, Thr, Ser or Asn; His 52 is substituted for Asp, Leu, Asn, Ser or Tyr; Asn 53 is substituted for Ala, Gly, Tyr, Ser, Lys or Thr; Ser 54 is substituted for Asn, Thr, Lys, Asp or Gly; Asn 56 is substituted for Tyr, Arg, Glu, Asp, Gly, Val, Ser or Ala; and/or Asn 58 is substituted for Lys, Thr, Ser, Asp, Arg, Gly, Phe or Tyr.

Examples of canonicals for CDRH3 as set out in SEQ ID NO:13, a variant thereof, the CDRH1 of SEQ ID NO:17 or a corresponding CDR are: Val 102 is substituted for Tyr, His, Ile, Ser, Asp or Gly.

Examples of canonicals for CDRL1 as set out in SEQ ID NO:14, a variant thereof, the CDRL1 of SEQ ID NO:19 or a corresponding CDR are: Asn 28 is substituted for Ser, Asp, Thr or Glu; Val 29 is substituted for Ile; Asn 30 is substituted for Asp, Leu, Tyr, Val, Ile, Ser, Phe, His, Gly or Thr; Ser 31 is substituted for Asn, Thr, Lys or Gly; Asn 32 is substituted for Phe, Tyr, Ala, His, Ser or Arg; Val 33 is substituted for Met, Leu, Ile or Phe; Ala 34 is substituted for Gly, Asn, Ser, His, Val or Phe.

Examples of canonicals for CDRL2 as set out in SEQ ID NO:15, a variant thereof, the CDRL1 of SEQ ID NO:19 or a corresponding CDR are: Ala 51 is substituted for Thr, Gly or Val.

Examples of canonicals for CDRL3 as set out in SEQ ID NO:16, a variant thereof, the CDRL1 of SEQ ID NO:19 or a corresponding CDR are: Gin 89 is substituted for Ser, Gly, Phe or Leu; Gin 90 is substituted for Asn or His; Cys 91 is substituted for Asn, Phe, Gly, Ser, Arg, Asp, His, Thr, Tyr or Val; Asn 92 is substituted for Tyr, Trp, Thr, Ser, Arg, Gin, His, Ala or Asp; Asn 93 is substituted for Glu, Gly, His, Thr, Ser, Arg or Ala; Tyr 94 is substituted for Asp, Thr, Val, Leu, His, Asn, Ile, Trp, Pro or Ser; and/or Phe 96 is substituted for Pro, Leu, Tyr, Arg, Ile or Trp.

There may be multiple variant CDR canonical positions per CDR, per corresponding CDR, per binding unit, per heavy or light chain variable region, per heavy or light chain, and per antigen binding protein, and therefore any combination of substitution may be present in the antigen binding protein of the invention, provided that the canonical structure of the CDR is maintained such that the antigen binding protein is capable of specifically binding SAP.

As discussed above, the particular canonical structure class of a CDR is defined by both the length of the CDR and by the loop packing, determined by residues located at key positions in both the CDRs and the framework regions.

Thus in addition to the CDRs listed in SEQ ID NO: 1-6 or 11-16, CDRs of SEQ ID NO:7, 9, 17 or 19, corresponding CDRs, binding units, or variants thereof, the canonical framework residues of an antigen binding protein of the invention may include (using Kabat numbering):
Heavy chain: Val, Ile or Gly at position 2; Leu or Val at position 4; Leu, Ile, Met or Val at position 20; Cys at position 22; Thr, Ala, Val, Gly or Ser at position 24; Gly at position 26; Ile, Phe, Leu or Ser at position 29; Trp at position 36; Trp or Tyr at position 47; Ile, Met, Val or Leu at position 48; Ile, Leu, Phe, Met or Val at position 69; Val, Ala or Leu at position 71; Ala, Leu, Val, Tyr or Phe at position 78; Leu or Met at position 80; Tyr or Phe at position 90; Cys at position 92; and/or Arg, Lys, Gly, Ser, His or Asn at position 94.
Light chain: Ile, Leu or Val at position 2; Val, Gln, Leu or Glu at position 3; Met or Leu at position 4; Cys at position 23; Trp at position 35; Tyr, Leu or Phe at position 36; Leu, Arg or Val at position 46; Tyr, His, Phe or Lys at position 49; Tyr or Phe at position 71; Cys at position 88; and/or Phe at position 98.

In a particular embodiment, the heavy chain framework comprises the following residues: Val at position 2, Leu at position 4, Val at position 20, Cys at position 22, Ala at position 24, Gly at position 26, Phe at position 29, Trp at position 36, Trp at position 47, Met at position 48, Ile at position 69, Ala at position 71, Ala at position 78, Met at position 80, Tyr at position 90, Cys at position 92, and Arg at position 94; and the light chain framework comprises the following residues: Ile at position 2, Gln at position 3, Met at position 4, Cys at position 23, Trp at position 35, Tyr at position 36, Leu at position 46, His at position 49, Phe at position 71, Cys at position 88, and Phe at position 98.

Any one, any combination, or all of the framework positions described above may be present in the antigen binding protein of the invention. There may be multiple variant framework canonical positions per heavy or light chain variable region, per heavy or light chain, and per antigen binding protein, and therefore any combination may be present in the antigen binding protein of the invention, provided that the canonical structure of the framework is maintained.

The humanised heavy chain variable domain may comprise the CDRs listed in SEQ ID NO:1-3; variant CDRs; corresponding CDRs in SEQ ID NO:7; binding units; or variants thereof, within an acceptor antibody framework having 75% or greater, 80% or greater, 85% or greater, 90% or greater, 95% or greater, 98% or greater, 99% or greater or 100% identity in the framework regions to the human acceptor variable domain sequence in SEQ ID NO:25. The humanised light chain variable domain may comprise the CDRs listed in SEQ ID NO:4-6; variant CDRs; corresponding CDRs in SEQ ID NO:9; binding units; or variants thereof, within an acceptor antibody framework having 75% or greater, 80% or greater, 85% or greater, 90% or greater, 95% or greater, 98% or greater, 99% or greater or 100% identity in the framework regions to the human acceptor variable domain sequence in SEQ ID NO:32.

The humanised heavy chain variable domain may comprise the CDRs listed in SEQ ID NO:11-13; variant CDRs; corresponding CDRs in SEQ ID NO:17; binding units; or variants thereof, within an acceptor antibody framework having 75% or greater, 80% or greater, 85% or greater, 90% or greater, 95% or greater, 98% or greater, 99% or greater or 100% identity in the framework regions to the human acceptor variable domain sequence in SEQ ID NO:25. The humanised light chain variable domain may comprise the CDRs listed in SEQ ID NO:14-16; variant CDRs; corresponding CDRs in SEQ ID NO:19; binding units; or variants thereof, within an acceptor antibody framework having 75% or greater, 80% or greater, 85% or greater, 90% or greater, 95% or greater, 98% or greater, 99% or greater or 100% identity in the framework regions to the human acceptor variable domain sequence in SEQ ID NO:32.

The invention also provides an antigen binding protein which specifically binds to SAP and comprises a heavy chain variable region selected from any one of SEQ ID NO:27-31. The antigen binding protein may comprise a light chain variable region selected from any one of SEQ ID NO:34-36 Any of the heavy chain variable regions may be combined with any of the light chain variable regions.

The antigen binding protein may comprise any one of the following heavy chain and light chain variable region combinations: H0L0 (SEQ ID NO:27 and SEQ ID NO:34), H0L1 (SEQ ID NO:27 and SEQ ID NO:35), H0L2 (SEQ ID NO:27 and SEQ ID NO:36), H1L0 (SEQ ID NO:28 and SEQ ID NO:34), H1L1 (SEQ ID NO:28 and SEQ ID NO:35), H1L2 (SEQ ID NO:28 and SEQ ID NO:36), H2L0 (SEQ ID NO:29 and SEQ ID NO:34), H2L1 (SEQ ID NO:29 and SEQ ID NO:35), H2L2 (SEQ ID NO:29 and SEQ ID NO:36), H3L0 (SEQ ID NO:30 and SEQ ID NO:34), H3L1 (SEQ ID NO:30 and SEQ ID NO:35), H3L2 (SEQ ID NO:30 and SEQ ID NO:36), H4L0 (SEQ ID NO:31 and SEQ ID NO:34), H4L1 (SEQ ID NO:31 and SEQ ID NO:35), or H4L2 (SEQ ID NO:31 and SEQ ID NO:36).

The invention also provides an antigen binding protein which specifically binds to SAP and comprises a heavy chain variable region selected from any one of SEQ ID NO:37-40. The antigen binding protein may comprise a light chain variable region of SEQ ID NO:41, SEQ ID NO:42 or SEQ ID NO:74. Any of the heavy chain variable regions may be combined with any of the light chain variable regions.

The antigen binding protein may comprise any one of the following heavy chain and light chain variable region combinations: H0L0 (SEQ ID NO:37 and SEQ ID NO:41), H0L1 (SEQ ID NO:37 and SEQ ID NO:42), H1L0 (SEQ ID NO:38 and SEQ ID NO:41), H1L1 (SEQ ID NO:38 and SEQ ID NO:42), H2L0 (SEQ ID NO:39 and SEQ ID NO:41), H2L1 (SEQ ID NO:39 and SEQ ID NO:42), H3L0 (SEQ ID NO:40 and SEQ ID NO:41), or H3L1 (SEQ ID NO:40 and SEQ ID NO:42). L0 (SEQ ID NO:41) may be substituted with L0 91 A (SEQ ID NO:74).

The antibody heavy chain variable region may have 75% or greater, 80% or greater, 85% or greater, 90% or greater, 95% or greater, 96% or greater, 97% or greater, 98% or greater, 99% or greater or 100% identity to SEQ ID NO:28. The antibody light chain variable region may have 75% or greater, 80% or greater, 85% or greater, 90% or greater, 95% or greater, 96% or greater, 97% or greater, 98% or greater, 99% or greater, or 100% identity to SEQ ID NO:35.

The antibody heavy chain variable region may have 75% or greater, 80% or greater, 85% or greater, 90% or greater, 95% or greater, 96% or greater, 97% or greater, 98% or greater, 99% or greater or 100% identity to SEQ ID NO:40. The antibody light chain variable region may have 75% or greater, 80% or greater, 85% or greater, 90% or greater, 95% or greater, 96% or greater, 97% or greater, 98% or greater, 99% or greater, or 100% identity to SEQ ID NO:41. The antibody light chain variable region may have 75% or greater, 80% or greater, 85% or greater, 90% or greater, 95% or greater, 96% or greater, 97% or greater, 98% or greater, 99% or greater, or 100% identity to SEQ ID NO:74.

The antibody heavy chain variable region may be a variant of any one of SEQ ID NO:27-31 which contains 30, 25, 20, 15, 10, 9, 8, 7, 6, 5, 4, 3, 2 or 1 amino acid substitutions, insertions or deletions. The antibody light chain variable region may be a variant of any one of SEQ ID NO:34-36 which contains 30, 25, 20, 15, 10, 9, 8, 7, 6, 5, 4, 3, 2 or 1 amino acid substitutions, insertions or deletions.

The antibody heavy chain variable region may be a variant of any one of SEQ ID NO:37-40 which contains 30, 25, 20, 15, 10, 9, 8, 7, 6, 5, 4, 3, 2 or 1 amino acid substitutions, insertions or deletions. The antibody light chain variable region may be a variant of SEQ ID NO:41, 42 or 74 which contains 30, 25, 20, 15, 10, 9, 8, 7, 6, 5, 4, 3, 2 or 1 amino acid substitutions, insertions or deletions.

For example, the canonical CDRs and canonical framework residue substitutions described above may also be present in the variant heavy or light chain variable regions as variant sequences that are at least 75% identical or which contain up to 30 amino acid substitutions.

Any of the heavy chain variable regions may be combined with a suitable human constant region. Any of the light chain variable regions may be combined with a suitable constant region.

The antigen binding protein of the invention may comprise a heavy chain of SEQ ID NO:62 and/or a light chain variable region of SEQ ID NO:64.

The antibody heavy chain may have 75% or greater, 80% or greater, 85% or greater, 90% or greater, 95% or greater, 96% or greater, 97% or greater, 98% or greater, 99% or greater or 100% identity to SEQ ID NO:62. The antibody light chain may have 75% or greater, 80% or greater, 85% or greater, 90% or greater, 95% or greater, 96% or greater, 97% or greater, 98% or greater, 99% or greater, or 100% identity to SEQ ID NO:64.

The antibody heavy chain may be a variant of any one of SEQ ID NO:62 which contains 30, 25, 20, 15, 10, 9, 8, 7, 6, 5, 4, 3, 2 or 1 amino acid substitutions, insertions or deletions. The antibody light chain may be a variant of any one of SEQ ID NO:64 which contains 30, 25, 20, 15, 10, 9, 8, 7, 6, 5, 4, 3, 2 or 1 amino acid substitutions, insertions or deletions.

The disc-like SAP molecule has two faces. The single alpha helix present on each of the 5 protomers is located on the A face. The calcium dependent ligand binding pocket of each protomer is located on the B face and this face is therefore occluded when SAP is bound to amyloid fibrils. For antigen binding proteins of the present invention to have therapeutic utility, the epitope recognised by the antigen binding protein described herein is desirably accessible in SAP when SAP is bound to amyloid deposits and is therefore located on the A face or the edges of the SAP molecule. The antigen binding protein can then recognise and bind to amyloid bound SAP, leading to complement activation that triggers the body's efficient macrophage dependent clearance mechanism. Accordingly, in an embodiment of the invention the antigen binding protein binds human SAP which is bound to amyloid fibrils in vivo. In another embodiment of the invention, the antigen binding protein binds to the A face of human SAP.

The antigen binding protein may be derived from rat, mouse, rabbit, camel (or related camelid species), or primate (e.g. cynomolgus, Old World monkey, Great Ape or human). In a particular embodiment the antigen binding protein is derived from mouse. In another embodiment the antigen binding protein is derived from human. The antigen binding protein may be a humanised or chimeric antibody. The antigen binding protein may be a human antibody. The antigen binding protein is not a murine antibody.

The antigen binding protein may comprise a constant region, which may be of any isotype or subclass. The constant region may be of the IgG isotype, for example IgG1, IgG2, IgG3, IgG4 or variants thereof. The antigen binding protein constant region may be IgG1.

In a particular embodiment of the invention, the antigen binding protein comprises a constant region that is functional in activating complement e.g. human IgG1, IgG2 or IgG3.

In another embodiment of the invention, the antigen binding protein comprises a constant region that is functional in binding macrophages e.g. human IgG1 or IgG3.

In a further embodiment of the invention, the antigen binding protein comprises a constant region that is functional in both activating complement and binding macrophages e.g. human IgG1 or IgG3.

The antigen binding protein may comprise one or more modifications selected from a mutated constant domain such that the antibody has altered effector functions/ADCC and/or complement activation. Examples of suitable modifications are described in Shields et al. J. Biol. Chem (2001) 276: 6591-6604, Lazar et al. PNAS (2006) 103: 4005-4010 and U.S. Pat. No. 6,737,056, WO2004063351 and WO2004029207.

The antigen binding protein may comprise a constant domain with an altered glycosylation profile such that the antigen binding protein has altered effector functions/ADCC and/or complement activation. Examples of suitable methodologies to produce an antigen binding protein with an altered glycosylation profile are described in WO2003/011878, WO2006/014679 and EP1229125.

In an embodiment of the invention, antigen binding proteins are selected which do not have residues within regions that are responsible for antigen binding, e.g. the CDRs, that are susceptible to deamidation. In a further embodiment of the invention, antigen binding proteins are selected which do not have residues within regions responsible for complement activation that are susceptible to deamidation.

The present invention also provides a nucleic acid molecule which encodes an antigen binding protein as described herein. The nucleic acid molecule may comprise sequences encoding both the heavy chain variable or full length sequence; and the light chain variable or full length sequence. Alternatively, the nucleic acid molecule which encodes an antigen binding protein described herein may comprise sequences encoding the heavy chain variable or full length sequence; or light chain variable or full length sequence.

The nucleic acid molecule which encodes the heavy chain variable region may comprise any one of SEQ ID NO:51 or 53-57. The nucleic acid molecule which encodes the light chain variable region may comprise any one of SEQ ID NO:52 or 58-60.

The nucleic acid molecule which encodes the heavy chain may comprise SEQ ID NO:61. The nucleic acid molecule which encodes the light chain may comprise SEQ ID NO:63.

The nucleic acid molecule which encodes the heavy chain variable region may comprise any one of SEQ ID NO:65 or 67-70. The nucleic acid molecule which encodes the light chain variable region may comprise any one of SEQ ID NO:66 or 71-73.

The nucleic acid molecule may also contain one or more nucleotide substitutions which do not alter the amino acid sequence of the encoded heavy and/or light chain.

The present invention also provides an expression vector comprising a nucleic acid molecule as described herein. Also provided is a recombinant host cell, comprising an expression vector as described herein.

The antigen binding protein described herein may be produced in a suitable host cell. A method for the production of the antigen binding protein as described herein may comprise the step of culturing a host cell as described herein and recovering the antigen binding protein. A recombinant transformed, transfected, or transduced host cell may comprise at least one expression cassette, whereby said expression cassette comprises a polynucleotide encoding a heavy chain of the antigen binding protein described herein and further comprises a polynucleotide encoding a light chain of the antigen binding protein described herein. Alternatively, a recombinant transformed, transfected or transduced host cell may comprise at least one expression cassette, whereby a first expression cassette comprises a polynucleotide encoding a heavy chain of the antigen binding protein described herein and further comprise a second cassette comprising a polynucleotide encoding a light chain of the antigen binding protein described herein. A stably transformed host cell may comprise a vector comprising one or more expression cassettes encoding a heavy chain and/or a light chain of the antigen binding protein described herein. For example such host cells may comprise a first vector encoding the light chain and a second vector encoding the heavy chain.

The host cell may be eukaryotic, for example mammalian. Examples of such cell lines include CHO or NS0. The host cell may be cultured in a culture media, for example serum-free culture media. The antigen binding protein may be secreted by the host cell into the culture media. The antigen binding protein can be purified to at least 95% or greater (e.g. 98% or greater) with respect to said culture media containing the antigen binding protein.

A pharmaceutical composition comprising the antigen binding protein and a pharmaceutically acceptable carrier may be provided. A kit-of-parts comprising the pharmaceutical composition together with instructions for use may be provided. For convenience, the kit may comprise the reagents in predetermined amounts with instructions for use.

Antibody Structures
Intact Antibodies

The light chains of antibodies from most vertebrate species can be assigned to one of two types called Kappa and Lambda based on the amino acid sequence of the constant region. Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, IgG2b.

The more conserved portions of the variable region are called Framework regions (FR). The variable domains of intact heavy and light chains each comprise four FR connected by three CDRs. The CDRs in each chain are held together in close proximity by the FR regions and with the CDRs from the other chain contribute to the formation of the antigen binding site of antibodies.

The constant regions are not directly involved in the binding of the antibody to the antigen but exhibit various effector functions such as participation in antibody dependent cell-mediated cytotoxicity (ADCC), phagocytosis via binding to Fcγ receptor, half-life/clearance rate via neonatal Fc receptor (FcRn) and complement activation via the C1q component, leading to the chemotactic, opsonic and, potentially in the case of a viable cellular antigen target, cytolytic actions of complement. Human antibodies of the IgG1 class are the most potent in activating the complement system and are therefore the desirable isotype for the therapeutic application of the antibodies of the present invention.

The human IgG2 constant region has been reported to essentially lack the ability to activate complement by the classical pathway or to mediate antibody-dependent cellular cytotoxicity. The IgG4 constant region has been reported to lack the ability to activate complement by the classical pathway and mediates antibody-dependent cellular cytotoxicity only weakly. Antibodies essentially lacking these effector functions may be termed 'non-lytic' antibodies.

Human Antibodies

Human antibodies may be produced by a number of methods known to those of skill in the art. Human antibodies can be made by the hybridoma method using human myeloma or mouse-human heteromyeloma cells lines see Kozbor (1984) J. Immunol 133, 3001, and Brodeur, Monoclonal Antibody Production Techniques and Applications, 51-63 (Marcel Dekker Inc, 1987). Alternative methods include the use of phage libraries or transgenic mice both of which utilize human variable region repertoires (see Winter (1994) Annu. Rev. Immunol 12: 433-455; Green (1999) J. Immunol. Methods 231: 11-23).

Several strains of transgenic mice are now available wherein their mouse immunoglobulin loci has been replaced with human immunoglobulin gene segments (see Tomizuka (2000) PNAS 97: 722-727; Fishwild (1996) Nature Biotechnol. 14: 845-851; Mendez (1997) Nature Genetics, 15: 146-156). Upon antigen challenge such mice are capable of producing a repertoire of human antibodies from which antibodies of interest can be selected.

Phage display technology can be used to produce human antigen binding proteins (and fragments thereof), see McCafferty (1990) Nature 348: 552-553 and Griffiths et al. (1994) EMBO 13: 3245-3260.

The technique of affinity maturation (Marks Bio/technol (1992) 10: 779-783) may be used to improve binding affinity wherein the affinity of the primary human antibody is improved by sequentially replacing the heavy (H) and light (L) chain variable regions with naturally occurring variants and selecting on the basis of improved binding affinities. Variants of this technique such as "epitope imprinting" are now also available, see for example WO 93/06213; Waterhouse (1993) Nucl. Acids Res. 21: 2265-2266.

Chimeric and Humanised Antibodies

Chimeric antibodies are typically produced using recombinant DNA methods. DNA encoding the antibodies (e.g. cDNA) is isolated and sequenced using conventional procedures (e.g. by using oligonucleotide probes that are capable of binding specifically to genes encoding the H and L chains of the antibody. Hybridoma cells serve as a typical source of such DNA. Once isolated, the DNA is placed into expression vectors which are then transfected into host cells such as *E. coli*, COS cells, CHO cells or myeloma cells that do not otherwise produce immunoglobulin protein to obtain synthesis of the antibody. The DNA may be modified by substituting the coding sequence for human L and H chains for the corresponding non-human (e.g. murine) H and L constant regions, see for example Morrison (1984) PNAS 81: 6851.

A large decrease in immunogenicity can be achieved by grafting only the CDRs of non-human (e.g. murine) antibodies ("donor" antibodies) onto human framework ("acceptor framework") and constant regions to generate humanised antibodies (see Jones et al. (1986) Nature 321: 522-525; and Verhoeyen et al. (1988) Science 239: 1534-1536). However, CDR grafting per se may not result in the complete retention of antigen-binding properties and it is frequently found that some framework residues (sometimes referred to as "back mutations") of the donor antibody need to be preserved in the humanised molecule if significant antigen-binding affinity is to be recovered (see Queen et al. (1989) PNAS 86: 10,029-10,033: Co et al. (1991) Nature 351: 501-502). In this case, human variable regions showing the greatest sequence homology to the non-human donor antibody are chosen from a database in order to provide the human framework (FR). The selection of human FRs can be made either from human consensus or individual human antibodies. Where necessary, key residues from the donor antibody can be substituted into the human acceptor framework to preserve CDR conformations. Computer modelling of the antibody maybe used to help identify such structurally important residues, see WO 99/48523.

Alternatively, humanisation maybe achieved by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan et al. (1991) Mol. Immunol. 28: 489-498; and Pedersen et al. (1994) J. Mol. Biol. 235: 959-973). Therefore it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable region "invisible" to the human immune system (see also Mark et al. (1994) in Handbook of Experimental Pharmacology Vol. 113: The pharmacology of Monoclonal Antibodies, Springer-Verlag, 105-134). This procedure of humanisation is referred to as "veneering" because only the surface of the antibody is altered, the supporting residues remain undisturbed. Further alternative approaches include that set out in WO04/006955 and the procedure of Humaneering™ (Kalobios) which makes use of bacterial expression systems and produces antibodies that are close to human germline in sequence (Alfenito-M Advancing Protein Therapeutics January 2007, San Diego, Calif.).

Bispecific Antigen Binding Proteins

A bispecific antigen binding protein is an antigen binding protein having binding specificities for at least two different epitopes. Methods of making such antigen binding proteins are known in the art. Traditionally, the recombinant production of bispecific antigen binding proteins is based on the co-expression of two immunoglobulin H chain-L chain pairs, where the two H chains have different binding specificities, see Millstein et al. (1983) Nature 305: 537-539; WO 93/08829; and Traunecker et al. (1991) EMBO 10: 3655-3659. Because of the random assortment of H and L chains, a potential mixture of ten different antibody structures are produced of which only one has the desired binding specificity. An alternative approach involves fusing the variable domains with the desired binding specificities to heavy chain constant region comprising at least part of the hinge region, CH2 and CH3 regions. The CH1 region containing the site necessary for light chain binding may be present in at least one of the fusions. DNA encoding these fusions, and if desired the L chain are inserted into separate expression vectors and are then co-transfected into a suitable host organism. It is possible though to insert the coding sequences for two or all three chains into one expression vector. In one approach, the bispecific antibody is composed of a H chain with a first binding specificity in one arm and a H-L chain pair, providing a second binding specificity in the other arm, see WO 94/04690. Also see Suresh et al. (1986) Methods in Enzymology 121: 210.

Antigen Binding Fragments

Fragments lacking the constant region lack the ability to activate complement by the classical pathway or to mediate antibody-dependent cellular cytotoxicity. Traditionally such fragments are produced by the proteolytic digestion of intact antibodies by e.g. papain digestion (see for example, WO 94/29348) but may be produced directly from recombinantly transformed host cells. For the production of ScFv, see Bird et al. (1988) Science 242: 423-426. In addition, antigen binding fragments may be produced using a variety of engineering techniques as described below.

Fv fragments appear to have lower interaction energy of their two chains than Fab fragments. To stabilise the association of the VH and VL domains, they have been linked with peptides (Bird et al. (1988) Science 242: 423-426; Huston et al. (1988) PNAS 85(16): 5879-5883), disulphide bridges (Glockshuber et al. (1990) Biochemistry 29: 1362-1367) and "knob in hole" mutations (Zhu et al. (1997) Protein Sci., 6: 781-788). ScFv fragments can be produced by methods well known to those skilled in the art, see Whitlow et al. (1991) Methods Companion Methods Enzymol, 2: 97-105 and Huston et al. (1993) Int. Rev. Immunol 10: 195-217. ScFv may be produced in bacterial cells such as *E. coli* or in eukaryotic cells. One disadvantage of ScFv is the monovalency of the product, which precludes an increased avidity due to polyvalent binding, and their short half-life. Attempts to overcome these problems include bivalent (ScFv')2 produced from ScFv containing an additional C-terminal cysteine by chemical coupling (Adams et al. (1993) Can. Res 53: 4026-4034; and McCartney et al. (1995) Protein Eng. 8: 301-314) or by spontaneous site-specific dimerisation of ScFv containing an unpaired C-terminal cysteine residue (see Kipriyanov et al. (1995) Cell. Biophys 26: 187-204). Alternatively, ScFv can be forced to form multimers by shortening the peptide linker to 3 to 12 residues to form "diabodies", see Holliger et al. (1993) PNAS 90: 6444-6448. Reducing the linker still further can result in ScFv trimers ("triabodies", see Kortt et al. (1997) Protein Eng 10: 423-433) and tetramers ("tetrabodies", see Le Gall et al. (1999) FEBS Lett, 453: 164-168). Construction of bivalent ScFv molecules can also be achieved by genetic fusion with protein dimerising motifs to form "miniantibodies" (see Pack et al. (1992) Biochemistry 31: 1579-1584) and "minibodies" (see Hu et al. (1996) Cancer Res. 56: 3055-3061). ScFv-Sc-Fv tandems ((ScFV)2) may also be produced by linking two ScFv units by a third peptide linker, see Kurucz et al. (1995) J. Immol. 154: 4576-4582. Bispecific diabodies can be produced through the non-covalent association of two single chain fusion products consisting of VH domain from one antibody connected by a short linker to the VL domain of another antibody, see Kipriyanov et al. (1998) Int. J. Can 77: 763-772. The stability of such bispecific diabodies can be enhanced by the introduction of disulphide bridges or "knob in hole" mutations as described supra or by the formation of single chain diabodies (ScDb) wherein two hybrid ScFv fragments are connected through a peptide linker see Kontermann et al. (1999) J. Immunol. Methods 226:179-188. Tetravalent bispecific molecules are available by e.g. fusing a ScFv fragment to the CH3 domain of an IgG molecule or to a Fab fragment through the hinge region, see Coloma et al. (1997) Nature Biotechnol. 15: 159-163. Alternatively, tetravalent bispecific molecules have been created by the fusion of bispecific single chain diabodies (see Alt et al. (1999) FEBS Lett 454: 90-94. Smaller tetravalent bispecific molecules can also be formed by the dimerization of either ScFv-ScFv tandems with a linker containing a helix-loop-helix motif (DiBi miniantibodies, see Muller et al. (1998) FEBS Lett 432: 45-49) or a single chain molecule comprising four antibody variable domains (VH and VL) in an orientation preventing intramolecular pairing (tandem diabody, see Kipriyanov et al. (1999) J. Mol. Biol. 293: 41-56). Bispecific F(ab')2 fragments can be created by chemical coupling of Fab' fragments or by heterodimerization through leucine zippers (see Shalaby et al. (1992) J. Exp. Med. 175: 217-225; and Kostelny et al. (1992), J. Immunol. 148: 1547-1553). Also available are isolated VH and VL domains (Domantis plc), see U.S. Pat. No. 6,248,516; U.S. Pat. No. 6,291,158; and U.S. Pat. No. 6,172,197.

Heteroconjugate Antibodies

Heteroconjugate antibodies are composed of two covalently joined antibodies formed using any convenient cross-linking methods. See, for example, U.S. Pat. No. 4,676,980.

Other Modifications

The antigen binding proteins of the present invention may comprise other modifications to enhance or change their effector functions. The interaction between the Fc region of an antibody and various Fc receptors (FcγR) is believed to mediate the effector functions of the antibody which include antibody-dependent cellular cytotoxicity (ADCC), fixation of complement, phagocytosis and half-life/clearance of the antibody. Various modifications to the Fc region of antibodies may be carried out depending on the desired property. For example, specific mutations in the Fc region to render an otherwise lytic antibody, non-lytic are detailed in EP 0629240 and EP 0307434 or one may incorporate a salvage receptor binding epitope into the antibody to increase serum half life see U.S. Pat. No. 5,739,277. Human Fcγ receptors include FcγR (I), FcγRIIa, FcγRIIb, FcγRIIIa and neonatal FcRn. Shields et al. (2001) J. Biol. Chem 276: 6591-6604 demonstrated that a common set of IgG1 residues is involved in binding all FcγRs, while FcγRII and FcγRIII utilize distinct sites outside of this common set. One group of IgG1 residues reduced binding to all FcγRs when altered to alanine: Pro-238, Asp-265, Asp-270, Asn-297 and Pro-239. All are in the IgG CH2 domain and clustered near the hinge joining CH1 and CH2. While FcγRI utilizes only the common set of IgG1 residues for binding, FcγRII and FcγRIII interact with distinct residues in addition to the common set. Alteration of some residues reduced binding only to FcγRII (e.g. Arg-292) or FcγRIII (e.g. Glu-293). Some variants showed improved binding to FcγRII or FcγRIII but did not affect binding to the other receptor (e.g. Ser-267Ala improved binding to FcγRII but binding to FcγRIII was unaffected). Other variants exhibited improved binding to FcγRII or FcγRIII with reduction in binding to the other receptor (e.g. Ser-298Ala improved binding to FcγRIII and reduced binding to FcγRII). For FcγRIIIa, the best binding IgG1 variants had combined alanine substitutions at Ser-298, Glu-333 and Lys-334. The neonatal FcRn receptor is believed to be involved in both antibody clearance and the transcytosis across tissues (see Junghans (1997) Immunol. Res 16: 29-57; and Ghetie et al. (2000) Annu. Rev. Immunol. 18: 739-766). Human IgG1 residues determined to interact directly with human FcRn includes Ile253, Ser254, Lys288, Thr307, Gln311, Asn434 and His435. Substitutions at any of the positions described in this section may enable increased serum half-life and/or altered effector properties of the antibodies.

Other modifications include glycosylation variants of the antibodies. Glycosylation of antibodies at conserved positions in their constant regions is known to have a profound effect on antibody function, particularly effector functioning such as those described above, see for example, Boyd et al. (1996) Mol. Immunol. 32: 1311-1318. Glycosylation variants of the antibodies or antigen binding fragments thereof wherein one or more carbohydrate moiety is added, substituted, deleted or modified are contemplated. Introduction of an asparagine-X-serine or asparagine-X-threonine motif creates a potential site for enzymatic attachment of carbohydrate moieties and may therefore be used to manipulate the glycosylation of an antibody. In Raju et al. (2001) Biochemistry 40: 8868-8876 the terminal sialyation of a TNFR-IgG immunoadhesin was increased through a process of regalactosylation and/or resialylation using beta-1, 4-galactosyltransferace and/or alpha, 2,3 sialyltransferase. Increasing the terminal sialylation is believed to increase the half-life of the immunoglobulin. Antibodies, in common with most glycoproteins, are typically produced as a mixture of glycoforms. This mixture is particularly apparent when antibodies are produced in eukaryotic, particularly mammalian cells. A variety of methods have been developed to manufacture defined glycoforms, see Zhang et al. (2004) Science 303: 371: Sears et al. (2001) Science 291: 2344; Wacker et al. (2002) Science 298: 1790; Davis et al. (2002) Chem. Rev. 102: 579; Hang et al. (2001) Acc. Chem. Res 34: 727. The antibodies (for example of the IgG isotype, e.g. IgG1) as herein described may comprise a defined number (e.g. 7 or less, for example 5 or less, such as two or a single) of glycoform(s).

The antibodies may be coupled to a non-proteinaeous polymer such as polyethylene glycol (PEG), polypropylene glycol or polyoxyalkylene. Conjugation of proteins to PEG is an established technique for increasing half-life of proteins, as well as reducing antigenicity and immunogenicity of proteins. The use of PEGylation with different molecular weights and styles (linear or branched) has been investigated with intact antibodies as well as Fab' fragments, see Koumenis et al. (2000) Int. J. Pharmaceut. 198: 83-95.

Production Methods

Antigen binding proteins may be produced in transgenic organisms such as goats (see Pollock et al. (1999) J. Immunol. Methods 231: 147-157), chickens (see Morrow (2000) Genet. Eng. News 20: 1-55, mice (see Pollock et al.) or plants (see Doran (2000) Curr. Opinion Biotechnol. 11: 199-204; Ma (1998) Nat. Med. 4: 601-606; Baez et al. (2000) BioPharm 13: 50-54; Stoger et al. (2000) Plant Mol. Biol. 42: 583-590).

Antigen binding proteins may also be produced by chemical synthesis. However, antigen binding proteins are typically produced using recombinant cell culturing technology well known to those skilled in the art. A polynucleotide encoding the antigen binding protein is isolated and inserted into a replicable vector such as a plasmid for further cloning (amplification) or expression. One expression system is a glutamate synthetase system (such as sold by Lonza Biologics), particularly where the host cell is CHO or NS0. Polynucleotide encoding the antigen binding protein is readily isolated and sequenced using conventional procedures (e.g. oligonucleotide probes). Vectors that may be used include plasmid, virus, phage, transposons, minichromosomes of which plasmids are typically used. Generally such vectors further include a signal sequence, origin of replication, one or more marker genes, an enhancer element, a promoter and transcription termination sequences operably linked to the antigen binding protein polynucleotide so as to facilitate expression. Polynucleotide encoding the light and heavy chains may be inserted into separate vectors and introduced (for example by transformation, transfection, electroporation or transduction) into the same host cell concurrently or sequentially or, if desired, both the heavy chain and light chain can be inserted into the same vector prior to said introduction.

Codon optimisation may be used with the intent that the total level of protein produced by the host cell is greater when transfected with the codon-optimised gene in comparison with the level when transfected with the sequence. Several methods have been published (Nakamura et al. (1996) Nucleic Acids Research 24: 214-215; WO98/34640; WO97/11086). Due to the redundancy of the genetic code, alternative polynucleotides to those disclosed herein (particularly those codon optimised for expression in a given host cell) may also encode the antigen binding proteins described herein. The codon usage of the antigen binding protein of this invention therefore can be modified to accommodate codon bias of the host cell such to augment transcript and/or product yield (e.g. Hoekema et al Mol Cell Biol 1987 7(8): 2914-24). The choice of codons may be based upon suitable compatibility with the host cell used for expression.

Signal Sequences

Antigen binding proteins may be produced as a fusion protein with a heterologous signal sequence having a specific cleavage site at the N-terminus of the mature protein. The signal sequence should be recognised and processed by the host cell. For prokaryotic host cells, the signal sequence may be for example an alkaline phosphatase, penicillinase, or heat stable enterotoxin II leaders. For yeast secretion the signal sequences may be for example a yeast invertase leader, α factor leader or acid phosphatase leaders see e.g. WO90/13646. In mammalian cell systems, viral secretory leaders such as herpes simplex gD signal and a native immunoglobulin signal sequence may be suitable. Typically the signal sequence is ligated in reading frame to DNA encoding the antigen binding protein. A murine signal sequence such as that shown in SEQ ID NO: 79 may be used.

Origin of Replication

Origin of replications are well known in the art with pBR322 suitable for most gram-negative bacteria, 2µ plasmid for most yeast and various viral origins such as SV40, polyoma, adenovirus, VSV or BPV for most mammalian cells. Generally the origin of replication component is not needed for mammalian expression vectors but the SV40 may be used since it contains the early promoter.

Selection Marker

Typical selection genes encode proteins that (a) confer resistance to antibiotics or other toxins e.g. ampicillin, neomycin, methotrexate or tetracycline or (b) complement auxiotrophic deficiencies or supply nutrients not available in the complex media or (c) combinations of both. The selection scheme may involve arresting growth of the host cell. Cells, which have been successfully transformed with the genes encoding the antigen binding protein, survive due to e.g. drug resistance conferred by the co-delivered selection marker. One example is the DHFR selection marker wherein transformants are cultured in the presence of methotrexate. Cells can be cultured in the presence of increasing amounts of methotrexate to amplify the copy number of the exogenous gene of interest. CHO cells are a particularly useful cell line for the DHFR selection. A further example is the glutamate synthetase expression system (Lonza Biologics). An example of a selection gene for use in yeast is the trp1 gene, see Stinchcomb et al. (1979) Nature 282: 38.

Promoters

Suitable promoters for expressing antigen binding proteins are operably linked to DNA/polynucleotide encoding the antigen binding protein. Promoters for prokaryotic hosts include phoA promoter, beta-lactamase and lactose promoter systems, alkaline phosphatase, tryptophan and hybrid promoters such as Tac. Promoters suitable for expression in yeast cells include 3-phosphoglycerate kinase or other glycolytic enzymes e.g. enolase, glyceralderhyde 3 phosphate dehydrogenase, hexokinase, pyruvate decarboxylase, phosphofructokinase, glucose 6 phosphate isomerase, 3-phosphoglycerate mutase and glucokinase. Inducible yeast promoters include alcohol dehydrogenase 2, isocytochrome C, acid phosphatase, metallothionein and enzymes responsible for nitrogen metabolism or maltose/galactose utilization.

Promoters for expression in mammalian cell systems include viral promoters such as polyoma, fowlpox and adenoviruses (e.g. adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40. Of course the choice of promoter is based upon suitable compatibility with the host cell used for expression. A first plasmid may comprise a RSV and/or SV40 and/or CMV promoter, DNA encoding light chain variable region (VL), KC region together with neomycin and ampicillin resistance selection markers and a second plasmid comprising a RSV or SV40 promoter, DNA encoding the heavy chain variable region (VH), DNA encoding the γ1 constant region, DHFR and ampicillin resistance markers.

Enhancer Element

Where appropriate, e.g. for expression in higher eukaryotes, an enhancer element operably linked to the promoter element in a vector may be used. Mammalian enhancer sequences include enhancer elements from globin, elastase, albumin, fetoprotein and insulin. Alternatively, one may use an enhancer element from a eukaroytic cell virus such as SV40 enhancer (at bp100-270), cytomegalovirus early promoter enhancer, polyma enhancer, baculoviral enhancer or murine IgG2a locus (see WO04/009823). The enhancer may be located on the vector at a site upstream to the promoter. Alternatively, the enhancer may be located elsewhere, for example within the untranslated region or downstream of the polyadenylation signal. The choice and positioning of enhancer may be based upon suitable compatibility with the host cell used for expression.

Polyadenylation/Termination

In eukaryotic systems, polyadenylation signals are operably linked to DNA/polynucleotide encoding the antigen binding protein. Such signals are typically placed 3' of the open reading frame. In mammalian systems, non-limiting examples include signals derived from growth hormones, elongation factor-1 alpha and viral (e.g. SV40) genes or retroviral long terminal repeats. In yeast systems non-limiting examples of polydenylation/termination signals include those derived from the phosphoglycerate kinase (PGK) and the alcohol dehydrogenase 1 (ADH) genes. In prokaryotic systems, polyadenylation signals are typically not required and it is instead usual to employ shorter and more defined terminator sequences. The choice of polyadenylation/termination sequences may be based upon suitable compatibility with the host cell used for expression.

Other Methods/Elements for Enhanced Yields

In addition to the above, other features that can be employed to enhance yields include chromatin remodelling elements, introns and host-cell specific codon modification.

Host Cells

Suitable host cells for cloning or expressing vectors encoding antigen binding proteins are prokaroytic, yeast or higher eukaryotic cells. Suitable prokaryotic cells include eubacteria e.g. enterobacteriaceae such as *Escherichia* e.g. *E. coli* (for example ATCC 31,446; 31,537; 27,325), *Enterobacter, Erwinia, Klebsiella Proteus, Salmonella* e.g. *Salmonella typhimurium, Serratia* e.g. *Serratia marcescans* and *Shigella* as well as Bacilli such as *B. subtilis* and *B. licheniformis* (see DD 266 710), *Pseudomonas* such as *P. aeruginosa* and *Streptomyces*. Of the yeast host cells, *Saccharomyces cerevisiae, Schizosaccharomyces pombe, Kluyveromyces* (e.g. ATCC 16,045; 12,424; 24178; 56,500), *yarrowia* (EP402, 226), *Pichia pastoris* (EP 183 070, see also Peng et al. (2004) J. Biotechnol. 108: 185-192), *Candida, Trichoderma reesia* (EP 244 234), Penicillin, *Tolypocladium* and *Aspergillus* hosts such as *A. nidulans* and *A. niger* are also contemplated.

Higher eukaryotic host cells include mammalian cells such as COS-1 (ATCC No. CRL 1650) COS-7 (ATCC CRL 1651), human embryonic kidney line 293, baby hamster kidney cells (BHK) (ATCC CRL.1632), BHK570 (ATCC NO: CRL 10314), 293 (ATCC NO. CRL 1573), Chinese hamster ovary cells CHO (e.g. CHO-K1, ATCC NO: CCL 61, DHFR-CHO cell line such as DG44 (see Urlaub et al. (1986) Somatic Cell Mol. Genet. 12: 555-556), particularly those CHO cell lines adapted for suspension culture, mouse sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NS0 (see U.S. Pat. No. 5,807,715), Sp2/0, Y0.

Such host cells may also be further engineered or adapted to modify quality, function and/or yield of the antigen binding protein. Non-limiting examples include expression of specific modifying (e.g. glycosylation) enzymes and protein folding chaperones.

Cell Culturing Methods

Host cells transformed with vectors encoding antigen binding proteins may be cultured by any method known to those skilled in the art. Host cells may be cultured in spinner flasks, roller bottles or hollow fibre systems but for large scale production that stirred tank reactors are used particularly for suspension cultures. The stirred tankers may be adapted for aeration using e.g. spargers, baffles or low shear impellers. For bubble columns and airlift reactors direct aeration with air or oxygen bubbles maybe used. Where the host cells are cultured in a serum free culture media, the media is supplemented with a cell protective agent such as pluronic F-68 to help prevent cell damage as a result of the aeration process. Depending on the host cell characteristics, either microcarriers maybe used as growth substrates for anchorage dependent cell lines or the cells may be adapted to suspension culture (which is typical). The culturing of host cells, particularly invertebrate host cells may utilise a variety of operational modes such as fed-batch, repeated batch processing (see Drapeau et al. (1994) Cytotechnology 15: 103-109), extended batch process or perfusion culture. Although recombinantly transformed mammalian host cells may be cultured in serum-containing media such as fetal calf serum (FCS), such host cells may be cultured in synthetic serum-free media such as disclosed in Keen et al. (1995) Cytotechnology 17: 153-163, or commercially available media such as ProCHO-CDM or UltraCHO™ (Cambrex N.J., USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g. Scharfenberg et al. (1995) in Animal Cell Technology: Developments towards the 21st century (Beuvery et al. eds, 619-623, Kluwer Academic publishers).

Antigen binding proteins secreted into the media may be recovered and purified using a variety of techniques to provide a degree of purification suitable for the intended use. For example the use of antigen binding proteins for the treatment of human patients typically mandates at least 95% purity, more typically 98% or 99% or greater purity (compared to the crude culture medium). Cell debris from the culture media is typically removed using centrifugation followed by a clarification step of the supernatant using e.g. microfiltration, ultrafiltration and/or depth filtration. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429,746) are available. The antibodies, following various clarification steps, can be captured using Protein A or G affinity chromatography. Further chromatography steps can follow such as ion exchange and/or HA chromatography, anion or cation exchange, size exclusion chromatography and ammonium sulphate precipitation. Various virus removal steps may also be employed (e.g. nanofiltration using e.g. a DV-20 filter). Following these various steps, a purified (for example a monoclonal) preparation comprising at least 75 mg/ml or greater, or 100 mg/ml or greater, of the antigen binding protein is provided. Such preparations are substantially free of aggregated forms of antigen binding proteins.

Bacterial systems may be used for the expression of antigen binding fragments. Such fragments can be localised intracellularly, within the periplasm or secreted extracellularly. Insoluble proteins can be extracted and refolded to form active proteins according to methods known to those skilled in the art, see Sanchez et al. (1999) J. Biotechnol. 72: 13-20; and Cupit et al. (1999) Lett Appl Microbiol 29: 273-277.

Deamidation is a chemical reaction in which an amide functional group is removed. In biochemistry, the reaction is important in the degradation of proteins because it damages the amide-containing side chains of the amino acids asparagine and glutamine. Asparagine is converted to a mixture of isoaspartate and aspartate. Deamidation of glutamine residues occurs at a much lower rate. Deamidation reactions are believed to be one of the factors that can limit the useful lifetime of a protein, they are also one of the most common post-translational modifications occurring during the manufacture of therapeutic proteins. For example, a reduction or loss of in vitro or in vivo biological activity has been reported for recombinant human DNAse and recombinant soluble CD4, whereas other recombinant proteins appear to be unaffected.

Pharmaceutical Compositions

Purified preparations of an antigen binding protein as described herein may be incorporated into pharmaceutical compositions for use in the treatment of the human diseases, disorders and conditions described herein. The terms diseases, disorders and conditions are used interchangeably. The pharmaceutical composition can be used in the treatment of any diseases where amyloid deposits are present in the tissues and contribute to structural and functional damage leading to clinical illness. SAP is always present in all amyloid deposits in vivo and the pharmaceutical composition comprising a therapeutically effective amount of the antigen binding protein described herein can be used in the treatment of diseases responsive to clearance of amyloid deposits from the tissues.

The pharmaceutical preparation may comprise an antigen binding protein in combination with a pharmaceutically acceptable carrier. The antigen binding protein may be administered alone, or as part of a pharmaceutical composition.

Typically such compositions comprise a pharmaceutically acceptable carrier as known and called for by acceptable pharmaceutical practice, see e.g. Remingtons Pharmaceutical Sciences, 16th edition (1980) Mack Publishing Co. Examples of such carriers include sterilised carriers such as saline, Ringers solution or dextrose solution, optionally buffered with suitable buffers to a pH within a range of 5 to 8.

Pharmaceutical compositions may be administered by injection or continuous infusion (e.g. intravenous, intraperitoneal, intradermal, subcutaneous, intramuscular or intraportal). Such compositions are suitably free of visible particulate matter. Pharmaceutical compositions may also be administered orally, specifically those containing CPHPC.

Pharmaceutical compositions may comprise between 1 mg to 10 g of antigen binding protein, for example between 5 mg and 1 g of antigen binding protein. Alternatively, the composition may comprise between 5 mg and 500 mg, for example between 5 mg and 50 mg.

Methods for the preparation of such pharmaceutical compositions are well known to those skilled in the art. Pharmaceutical compositions may comprise between 1 mg to 10 g of antigen binding protein in unit dosage form, optionally together with instructions for use. Pharmaceutical compositions may be lyophilised (freeze dried) for reconstitution prior to administration according to methods well known or apparent to those skilled in the art. Where antibodies have an IgG1 isotype, a chelator of copper, such as citrate (e.g. sodium citrate) or EDTA or histidine, may be added to the pharmaceutical composition to reduce the degree of copper-mediated degradation of antibodies of this isotype, see EP0612251. Pharmaceutical compositions may also comprise a solubiliser such as arginine base, a detergent/anti-aggregation agent such as polysorbate 80, and an inert gas such as nitrogen to replace vial headspace oxygen.

Effective doses and treatment regimes for administering the antigen binding protein are generally determined empirically and may be dependent on factors such as the age, weight and health status of the patient and disease or disorder to be treated. Such factors are within the purview of the attending physician. Guidance in selecting appropriate doses may be found in e.g. Smith et al (1977) Antibodies in human diagnosis and therapy, Raven Press, New York.

The dosage of antigen binding protein administered to a subject is generally between 1 µg/kg to 150 mg/kg, between 0.1 mg/kg and 100 mg/kg, between 0.5 mg/kg and 50 mg/kg, between 1 and 25 mg/kg or between 1 and 10 mg/kg of the subject's body weight. For example, the dose may be 10 mg/kg, 30 mg/kg, or 60 mg/kg. The antigen binding protein may be administered parenterally, for example subcutaneously, intravenously or intramuscularly.

The SAP-depleting compound may be administered at a dose of between 0.1 mg/kg and 2 mg/kg, depending on its activity. The SAP-depleting compound may be administered as a fixed dose, independent of a dose per subject weight ratio. The SAP-depleting compound may be administered in one or more separate, simultaneous or sequential parenteral doses of 100 mg or less, of 50 mg or less, 25 mg or less, or 10 mg or less.

If desired, the effective daily dose of a therapeutic composition may be administered as two, three, four, five, six or more sub-doses administered separately at appropriate intervals throughout the day, optionally, in unit dosage forms.

The antigen binding protein may be administered in a single large dose or in smaller repeated doses.

The administration of a dose may be by slow continuous infusion over a period of from 2 to 24 hours, such as from 2 to 12 hours, or from 2 to 6 hours. This may result in reduced toxic side effects.

The administration of a dose may be repeated one or more times as necessary, for example, three times daily, once every day, once every 2 days, once a week, once a fortnight, once a month, once every 3 months, once every 6 months, or once every 12 months. The antigen binding proteins may be administered by maintenance therapy, for example once a week for a period of 6 months or more. The antigen binding proteins may be administered by intermittent therapy, for example for a period of 3 to 6 months and then no dose for 3 to 6 months, followed by administration of antigen binding proteins again for 3 to 6 months, and so on in a cycle.

For example, the dose may be administered subcutaneously, once every 14 or 28 days in the form of multiple sub-doses on each day of administration.

The antigen binding protein may be administered to the subject in such a way as to target therapy to a particular site. For example, the antigen binding protein may be injected locally into a circumscribed local amyloid mass in the tissues, or infused into the blood supply to an amyloidotic organ.

The antigen binding protein must be used in combination with one or more other therapeutically active agents, specifically SAP depleting compounds, for the treatment of the diseases described herein. Effective depletion of SAP from the circulation must be achieved before administration of the SAP binding protein in order for the latter to be given both safely and effectively.

The SAP depleting compound is administered first so that almost all of the circulating SAP is cleared. Since this leaves substantial amounts of SAP associated with the amyloid deposits in the tissues the sequential administration of an anti-SAP antigen binding protein enables the localisation and specific binding to the amyloid deposits to promote their rapid and extensive regression. Suitably, the anti-SAP antigen binding protein may be administered 1, 2, 3, 4, 5, 6, 7, 8, 9, 10, 12, 15, 20 or 25 or more days after starting the treatment(s) with the SAP depleting compound.

The sequential administration may involve two or more sequential treatments with SAP depleting compound followed by two or more sequential treatments with the anti-SAP antigen binding protein.

The sequential administration may involve one treatment with SAP depleting compound followed by one sequential treatment with the anti-SAP antigen binding protein, which is then repeated one or more times.

The sequential/subsequent dose may be an amount that is more than the initial/previous dose or less than the initial/previous dose.

The administration of an initial dose of SAP-depleting compound protein may be followed by the administration of one or more sequential (e.g. subsequent) doses of SAP depleting compound and/or the anti-SAP antigen binding protein, and wherein said one or more sequential doses may be in an amount that is approximately the same or less than the initial dose.

After initial depletion of circulating SAP, the administration of further doses of SAP depleting compound and the first dose of anti-SAP antigen binding protein may be followed by the administration of one or more sequential (e.g. subsequent) doses, and wherein at least one of the subsequent doses is in an amount that is more than the initial dose.

Accordingly, the administration may use a pre-determined or routine schedule for administration, thereby resulting in a predetermined designated period of time between dose administrations. The schedule may encompass periods of time which are identical or which differ in length, as long as the schedule is predetermined. Any particular combination would be covered by the schedule as long as it is determined ahead of time that the appropriate schedule involves administration on a certain day.

The pharmaceutical composition may comprise a kit of parts of the antigen binding protein together with other medicaments, optionally with instructions for use. For convenience, the kit may comprise the reagents in predetermined amounts with instructions for use.

The terms "individual", "subject" and "patient" are used herein interchangeably. The subject may be a primate (e.g. a marmoset or monkey). The subject is typically a human.

Treatment can be therapeutic, prophylactic or preventative. The subject will be one who is in need thereof. Those in need of treatment may include individuals already suffering from a particular medical disease in addition to those who may develop the disease in the future.

Thus, the SAP depleting compound followed by the SAP antigen binding protein described herein can be used for prophylactic or preventative treatment. In this case, the sequential treatments described herein are administered to an individual in order to prevent or delay the onset of one or more aspects or symptoms of the disease. The subject can be asymptomatic or may have a genetic predisposition to the disease, as amyloid deposits are known to be present in the tissues and to accumulate for periods of time before they cause sufficient damage to produce clinical symptoms. Such sub-clinical amyloid deposition can be detected by histological examination of tissue biopsies or by non-invasive imaging procedures, including radiolabelled SAP scintigraphy, echocardiography and cardiac magnetic resonance imaging. After first depleting circulating SAP, a prophylactically effective amount of the antigen binding protein is administered to such an individual. A prophylactically effective amount is an amount which prevents or delays the onset of one or more aspects or symptoms of a disease described herein.

The antigen binding protein described herein may also be used in methods of therapy. The term "therapy" encompasses alleviation, reduction, or prevention of at least one aspect or symptom of a disease. For example, the antigen binding protein described herein may be used to ameliorate or reduce one or more aspects or symptoms of a disease described herein.

The antigen binding protein described herein is used in an effective amount for therapeutic, prophylactic or preventative treatment. A therapeutically effective amount of the antigen binding protein described herein is an amount effective to ameliorate or reduce one or more aspects or symptoms of the disease. The antigen binding protein described herein may also be used to treat, prevent, or cure the disease described herein.

The antigen binding protein described herein can have a generally beneficial effect on the subject's health, for example it can increase the subject's expected longevity.

The antigen binding protein described herein need not affect a complete cure, or eradicate every symptom or manifestation of the disease to constitute a viable therapeutic treatment. As is recognised in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a disease in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur (for example by delaying the onset of the disease) or worsen in a subject, is sufficient.

Antigen binding proteins described herein may be used in treating or preventing a disease associated with amyloid deposition i.e. amyloidosis.

"Amyloidosis" is any disease characterized by the extracellular accumulation of amyloid in various organs and tissues of the body.

The term "amyloid" refers to extracellular deposits in the tissues of insoluble protein fibres composed of fibrils with characteristic ultrastructural morphology, a cross-β sheet core structure and the pathognomonic histochemical tinctorial property of binding Congo red dye from alkaline alcoholic solution and then giving red-green dichroism when viewed microscopically in strong cross polarised light. About 25 different unrelated proteins are known to form amyloid fibrils which deposit in human tissues and share all these typical properties. Amyloid deposits in the brain substance, cerebral amyloid, differ somewhat from amyloid deposits elsewhere in the body in that they are always focal and microscopic in size, and are commonly referred to as amyloid plaques.

Amyloidosis, that is disease directly caused by deposition of amyloid in the tissues, comprises both local amyloidosis, in which the deposits are confined to one anatomical region and/or one tissue or organ system, and systemic amyloidosis in which the deposits can occur in any organ or tissue in the body, including blood vessels and connective tissues. The cause of amyloidosis can be either acquired or hereditary. Acquired amyloidosis arises as a complication of a preceding medical condition, which can itself be either acquired or hereditary. Thus reactive systemic amyloidosis, known as amyloid A protein (AA) type is a complication of chronic active inflammatory diseases such as rheumatoid arthritis, juvenile rheumatoid arthritis, Crohn's disease, chronic infections and chronic sepsis, and of hereditary periodic fever syndromes such as familial Mediterranean fever, Muckle-Wells syndrome and CINCA syndrome. Dialysis related amyloidosis is caused by accumulation of β2-microglobulin as a result of end stage renal failure. Monoclonal immunoglobulin light chain (AL) amyloidosis is a complication of multiple myeloma or otherwise benign monoclonal gammopathy (monoclonal gammopathy of uncertain significance, MGUS). Acquired amyloidosis of transthyretin type can occur without any preceding illness and is merely a complication of old age. Hereditary amyloidosis is caused by mutations in the genes for various proteins which encode expression of variant proteins having an increased propensity to form amyloid fibrils, and includes disease caused by transthyretin, apolipoprotein AI, gelsolin, lysozyme, cystatin C and amyloid β-protein. Comprehensive descriptions of all the different forms of amyloidosis and the proteins involved are available in textbooks and the scientific literature (Pepys, M. B. (2006) Annu. Rev. Med., 57: 223-241; Pepys and Hawkins (2003) Amyloidosis. Oxford Textbook of Medicine, 4$^{th}$ Ed., Vol. 2, Oxford University Press, Oxford, pp. 162-173; Pepys and Hawkins (2001) Amyloidosis. Samter's Immunologic Diseases, Sixth Ed., Vol. 1, Lippincott Williams & Williams, Philadelphia, pp. 401-412).

Local amyloid deposition, confined to one organ or tissue, can be clinically silent or can cause serious tissue damage and disease. For example, cerebral amyloid angiopathy in which the vascular amyloid deposits are composed of Aβ protein, is usually a sporadic acquired condition arising for reasons which are not understood in the absence of any other pathology, and is a major cause of cerebral haemorrhage and stroke. There are several very important and common diseases, particularly Alzheimer's disease (AD) and type 2 diabetes, in which amyloid deposits are always present but in which the precise mechanisms causing these respective diseases are not yet known. Nevertheless the local deposition of amyloid in the brain and cerebral blood vessels in Alzheimer's disease, and in the pancreatic islets in diabetes is very likely to exacerbate pathology and disease. Accordingly, the present invention includes treatment of both Alzheimer's disease and type 2 diabetes, indeed of any condition associated with the presence of amyloid deposits in the tissues, with antigen binding proteins as disclosed herein.

Many forms of transmissible spongiform encephalopathy (prion diseases) are associated with amyloid deposits in the brain, and the present invention therefore relates to all these conditions, including variant Creutzfeldt-Jakob disease in humans, Creutzfeldt-Jakob disease itself, kuru and the various other forms of human prion disease, and also bovine spongiform encephalopathy, chronic wasting disease of mule-deer and elk, and transmissible encephalopathy of mink.

Diagnostic Methods of Use

The antigen binding proteins described herein may be used to detect SAP in a biological sample in vitro or in vivo for diagnostic purposes. For example, the anti-SAP antigen binding proteins can be used to detect SAP in serum or in associated with amyloid e.g. amyloid plaques. The amyloid may have been first removed (for example a biopsy) from a human or animal body. Conventional immunoassays may be employed, including ELISA, Western blot, immunohistochemistry, or immunoprecipitation.

The antigen binding proteins may be provided in a diagnostic kit comprising one or more antigen binding proteins, a detectable label, and instructions for use of the kit. For convenience, the kit may comprise the reagents in predetermined amounts with instructions for use.

EXAMPLES

Example 1—Sequencing of Hybridoma Variable Domains: SAP-E and SAP-K

SAP-E and SAP-K are from two groups of anti-SAP monoclonals, each group having been tested separately for their binding to human SAP in vitro. SAP-E and SAP-K showed the strongest binding to SAP, within their groups, and were compared with each other in different assays.

The first group of antibodies comprised antibodies from 7 hybridomas generated in a single conventional immunization with purified human SAP (SEQ ID NO:43 shown below) (details of method for purifying human SAP are given in Hawkins et al. (1991) Clin. Exp. Immunol. 84, 308-316) and fusion protocol and are designated SAP-A to SAP-G. Two of these antibodies, SAP-E and SAP-B, are IgG2a isotype while the others are all IgG1 isotype (see Example 13, Table 11).

The second group of antibodies comprised 6 different IgG2a monoclonals (SAP-H to SAP-M) derived by standard techniques from immunization with purified human SAP (SEQ ID NO:43 shown below) (Hawkins et al. (1991) Clin. Exp. Immunol. 84, 308-316) and a conventional fusion to produce hybridomas which were cloned by routine methods.

homo sapiens SAP mature amino acid sequence
(SEQ ID NO: 43)
HTDLSGKVFVFPRESVTDHVNLITPLEKPLQNFTLCFRAYSDLSRAYS

LFSYNTQGRDNELLVYKERVGEYSLYIGRHKVTSKVIEKFPAPVHICV

SWESSSGIAEFWINGTPLVKKGLRQGYFVEAQPKIVLGQEQDSYGGKF

DRSQSFVGEIGDLYMWDSVLPPENILSAYQGTPLPANILDWQALNYEI

RGYVIIKPLVWV

For comparison purposes, the mouse SAP sequence, which has a 69.4% identity with human SAP, is given below.

mus musculus SAP mature protein
(SEQ ID NO: 44)
QTDLKRKVFVFPRESETDHVKLIPHLEKPLQNFTLCFRTYSDLSRSQS

LFSYSVKGRDNELLIYKEKVGEYSLYIGQSKVTVRGMEEYLSPVHLCT

TWESSSGIVEFWVNGKPWVKKSLQREYTVKAPPSIVLGQEQDNYGGGF

QRSQSFVGEFSDLYMWDYVLTPQDILFVYRDSPVNPNILNWQALNYEI

NGYVVIRPRVW

Total RNA was extracted from hybridoma cell pellets of approximately 10$^6$ cells using the RNeasy kit from Qiagen (#74106). AccessQuick RT-PCR System (A1702) was used to produce cDNA of the variable heavy and light regions using degenerate primers specific for the murine immunoglobulin gene leader sequences and murine IgG2a/κ constant regions. The purified RT-PCR fragments were cloned using the TA cloning kit from Invitrogen (K2000-01). A consensus sequence was obtained for each hybridoma by sequence alignment, and alignment with known immunoglobulin variable sequences listed in KABAT (Sequences of Proteins of Immunological Interest, 4th Ed., U.S. Department of Health and Human Services, National Institutes of Health (1987)). The consensus sequences for SAP-E and SAP-K are shown below.

SAP-E sequences
SAP-E CDRH1
(SEQ ID NO: 1)
TYNMH

SAP-E CDRH2
(SEQ ID NO: 2)
YIYPGDGNANYNQQFKG

SAP-E CDRH3
(SEQ ID NO: 3)
GDFDYDGGYYFDS

SAP-E CDRL1
(SEQ ID NO: 4)
RASENIYSYLA

SAP-E CDRL2
(SEQ ID NO: 5)
NAKTLAE

SAP-E CDRL3
(SEQ ID NO: 6)
QHHYGAPLT

SAP-E $V_H$ amino acid sequence (SEQ ID NO: 7) with CDRs underlined
QASLQQSGTELVRSGASVKMSCKASGFTFA<u>TYNMH</u>WIKQTPGQGLEWI G<u>YIYPGDGNANYNQQFKG</u>KATLTADTSSNTAYMQISSLTSEDSAVYFC AR<u>GDFDYDGGYYFDS</u>WGQGTTLTVSS SAP-E $V_H$ DNA sequence
(SEQ ID NO: 8)
CAGGCTTCTCTACAGCAGTCTGGGACTGAGCTGGTGAGGTCTGGGGCC

TCAGTGAAGATGTCCTGCAAGGCTTCTGGCTTCACATTTGCCACTTAC

AATATGCACTGGATTAAGCAGACACCCGGACAGGGCCTGGAATGGATT

GGGTATATTTATCCTGGAGATGGTAATGCTAACTACAATCAGCAGTTC

AAGGGCAAGGCCACATTGACTGCAGACACATCCTCCAACACAGCCTAC

ATGCAGATCAGCAGCCTGACATCTGAAGACTCTGCGGTCTATTTCTGT

GCAAGAGGGGACTTTGATTACGACGGAGGGTACTACTTTGACTCCTGG

GGCCAGGGCACCACTCTCACAGTCTCCTCA

SAP-E $V_L$ amino acid sequence (SEQ ID NO: 9) with CDRs underlined
DIQMTQSPASLSASVGETVTITC<u>RASENIYSYLA</u>WYQQKQGRSPCILL VH<u>NAKTLAE</u>GVPSRVSGSGSGTHFSLKINGLQPEDFGNYYC<u>QHHYGAP</u>

<u>LT</u>FGAGTKLELK

SAP-E $V_L$ DNA sequence
(SEQ ID NO: 10)
GACATCCAGATGACTCAGTCTCCAGCCTCCCTATCTGCATCTGTGGGA

GAAACTGTCACCATCACATGTCGAGCAAGTGAGAATATTTACAGTTAT

TTAGCATGGTATCAGCAGAAACAGGGAAGATCCCCTCAGCTCCTGGTC

CATAATGCAAAAACCTTAGCAGAAGGTGTGCCATCAAGGGTCAGTGGC

AGTGGATCAGGCACACACTTTTCTCTGAAGATCAACGGCCTGCAGCCT

GAAGATTTTGGAATTATTACTGTCAACATCATTATGGTGCTCCGCTC

ACGTTCGGTGCTGGGACCAAGCTGGAACTGAAA

SAP-K sequences
SAP-K CDRH1
(SEQ ID NO: 11)
SYWMH

SAP-K CDRH2
(SEQ ID NO: 12)
MIHPNSVNTNYNEKFKS

SAP-K CDRH3
(SEQ ID NO: 13)
RNDYYWYFDV

SAP-K CDRL1
(SEQ ID NO: 14)
KASQNVNSNVA

SAP-K CDRL2
(SEQ ID NO: 15)
SASYRYS

SAP-K CDRL3
(SEQ ID NO: 16)
QQCNNYPFT

SAP-K $V_H$ amino acid sequence (SEQ ID NO: 17) with CDRs underlined
QVQLQQPGAELIKPGASVKLSCKASGYTFT<u>SYWMH</u>WVKQRPGQGLEWI G<u>MIHPNSVNTNYNEKFKS</u>KATLTVDKSSSTAYMQLNSLTSEDSAVYYC AR<u>RNDYYWYFDV</u>WGTGTTVTSS SAP-K $V_H$ DNA sequence
(SEQ ID NO: 18)
CAGGTCCAACTGCAGCAGCCTGGGGCTGAGCTGATAAAGCCTGGGGCT

TCAGTGAAGTTGTCCTGCAAGGCTTCTGGCTACACTTTCACCAGCTAC

TGGATGCACTGGGTGAAGCAGAGGCCTGGACAAGGCCTTGAGTGGATT

GGAATGATTCATCCTAATAGTGTTAATACTAACTACAATGAGAAGTTC

AAGAGTAAGGCCACACTGACTGTAGACAAATCCTCCAGCACAGCCTAC

ATGCAACTCAACAGCCTGACATCTGAGGACTCTGCGGTCTATTACTGT

GCAAGACGGAATGATTACTACTGGTACTTCGATGTCTGGGGCACAGGG

ACCACGGTCACCGTCTCCTCA

SAP-K $V_L$ amino acid sequence (SEQ ID NO: 19) with CDRs underlined
DIVMTQSQKFMSTSVGDRVSVTC<u>KASQNVNSNVA</u>WYQQKPGQSPKALI Y<u>SASYRYS</u>GVPDRFTGSGSGTDFTLTITNVQSEDLAEYFC<u>QQCNNYPF</u>

<u>T</u>FGSGTKLEIK

SAP-K $V_L$ DNA sequence
(SEQ ID NO: 20)
GACATTGTGATGACCCAGTCTCAAAAATTCATGTCCACATCAGTAGGA

GACAGGGTCAGCGTCACCTGCAAGGCCAGTCAGAATGTGAATTCTAAT

GTAGCCTGGTATCAACAGAAACCAGGGCAATCTCCTAAAGCACTGATT

TACTCGGCTTCCTACCGGTACAGTGGAGTCCCTGATCGCTTCACAGGC

AGTGGATCTGGGACAGATTTCACTCTCACCATCACCAATGTGCAGTCT

GAAGACTTGGCAGAGTATTTCTGTCAGCAATGTAACAACTATCCATTC

ACGTTCGGCTCGGGGACAAAGTTGGAAATAAAA

Example 2: Construction of Chimeric Antibodies

Chimeric antibodies, comprising parent murine variable domains grafted onto human IgG1/κ wild-type constant regions were constructed by PCR cloning for SAP-E and SAP-K. Based on the consensus sequence, primers to amplify the murine variable domains were designed, incorporating restriction sites required to facilitate cloning into mammalian expression vectors. Through introduction of the restriction site in FR4 (Framework Region 4 (V-region sequence following CDR3 and preceding first constant domain)) the $V_H$ amino acid sequence in SAP-E was changed from TTLTVSS as shown in SEQ ID NO:7 to TLVTVSS and the $V_H$ amino acid sequence in SAP-K was changed from TTVTVSS as shown in SEQ ID NO:17 to TLVTVSS. In the SAP-K variable light chain an internal EcoRI site was present in CDRL1 and mutagenesis primers were designed to remove this undesired internal EcoRI site by changing one base pair—this did not change the amino acid sequence.

The full length heavy and light chain protein sequences of the SAP-E chimeric antibody (cSAP-E) are given in SEQ ID NO:21 and SEQ ID NO:22 respectively. The full length heavy and light chain protein sequences of the SAP-K chimeric antibody (cSAP-K) are given in SEQ ID NO:23 and SEQ ID NO:24 respectively.

SAP-E VH chimera nucleotide sequence
(SEQ ID NO: 45)
CAGGCTTCTCTACAGCAGTCTGGGACTGAGCTGGTGAGGTCTGGGGCC

TCAGTGAAGATGTCCTGCAAGGCTTCTGGCTTCACATTTGCCACTTAC

AATATGCACTGGATTAAGCAGACACCCGGACAGGGCCTGGAATGGATT

GGGTATATTTATCCTGGAGATGGTAATGCTAACTACAATCAGCAGTTC

AAGGGCAAGGCCACATTGACTGCAGACACATCCTCCAACACAGCCTAC

ATGCAGATCAGCAGCCTGACATCTGAAGACTCTGCGGTCTATTTCTGT

GCAAGAGGGGACTTTGATTACGACGGAGGGTACTACTTTGACTCCTGG

GGCCAGGGCACACTAGTGACCGTGTCCAGCGCCAGCACCAAGGGCCCC

AGCGTGTTCCCCCTGGCCCCCAGCAGCAAGAGCACCAGCGGCGGCACA

GCCGCCCTGGGCTGCCTGGTGAAGGACTACTTCCCCGAACCGGTGACC

GTGTCCTGGAACAGCGGAGCCCTGACCAGCGGCGTGCACACCTTCCCC

GCCGTGCTGCAGAGCAGCGGCCTGTACAGCCTGAGCAGCGTGGTGACC

GTGCCCAGCAGCAGCCTGGGCACCCAGACCTACATCTGTAACGTGAAC

CACAAGCCCAGCAACACCAAGGTGGACAAGAAGGTGGAGCCCAAGAGC

TGTGACAAGACCCACACCTGCCCCCCCTGCCCTGCCCCCGAGCTGCTG

GGAGGCCCCAGCGTGTTCCTGTTCCCCCCCAAGCCTAAGGACACCCTG

ATGATCAGCAGAACCCCCGAGGTGACCTGTGTGGTGGTGGATGTGAGC

CACGAGGACCCTGAGGTGAAGTTCAACTGGTACGTGGACGGCGTGGAG

GTGCACAATGCCAAGACCAAGCCCAGGGAGGAGCAGTACAACAGCACC

TACCGGGTGGTGTCCGTGCTGACCGTGCTGCACCAGGATTGGCTGAAC

GGCAAGGAGTACAAGTGTAAGGTGTCCAACAAGGCCCTGCCTGCCCCT

ATCGAGAAAACCATCAGCAAGGCCAAGGGCCAGCCCAGAGAGCCCCAG

GTGTACACCCTGCCCCCTAGCAGAGATGAGCTGACCAAGAACCAGGTG

TCCCTGACCTGCCTGGTGAAGGGCTTCTACCCCAGCGACATCGCCGTG

GAGTGGGAGAGCAACGGCCAGCCCGAGAACAACTACAAGACCACCCCC

CCTGTGCTGGACAGCGATGGCAGCTTCTTCCTGTACAGCAAGCTGACC

GTGGACAAGAGCAGATGGCAGCAGGGCAACGTGTTCAGCTGCTCCGTG

ATGCACGAGGCCCTGCACAATCACTACACCCAGAAGAGCCTGAGCCTG

TCCCCTGGCAAG

SAP-E VH chimera amino acid sequence
(SEQ ID NO: 21)
QASLQQSGTELVRSGASVKMSCKASGFTFATYNMHWIKQTPGQGLEWI

GYIYPGDGNANYNQQFKGKATLTADTSSNTAYMQISSLTSEDSAVYFC

ARGDFDYDGGYYFDSWGQGTLVTVSSASTKGPSVFPLAPSSKSTSGGT

AALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPELL

GGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSV

MHEALHNHYTQKSLSLSPGK

SAP-E VL chimera nucleotide sequence
(SEQ ID NO: 46)
GACATCCAGATGACTCAGTCTCCAGCCTCCCTATCTGCATCTGTGGGA

GAAACTGTCACCATCACATGTCGAGCAAGTGAGAATATTTACAGTTAT

TTAGCATGGTATCAGCAGAAACAGGGAAGATCCCCTCAGCTCCTGGTC

CATAATGCAAAAACCTTAGCAGAAGGTGTGCCATCAAGGGTCAGTGGC

AGTGGATCAGGCACACACTTTTCTCTGAAGATCAACGGCCTGCAGCCT

GAAGATTTTGGGAATTATTACTGTCAACATCATTATGGTGCTCCGCTC

ACGTTCGGTGCTGGGACCAAGCTGGAACTGAAACGTACGGTGGCCGCC

CCCAGCGTGTTCATCTTCCCCCCCAGCGATGAGCAGCTGAAGAGCGGC

ACCGCCAGCGTGGTGTGTCTGCTGAACAACTTCTACCCCCGGGAGGCC

AAGGTGCAGTGGAAGGTGGACAATGCCCTGCAGAGCGGCAACAGCCAG

GAGAGCGTGACCGAGCAGGACAGCAAGGACTCCACCTACAGCCTGAGC

AGCACCCTGACCCTGAGCAAGGCCGACTACGAGAAGCACAAGGTGTAC

GCCTGTGAGGTGACCCACCAGGGCCTGTCCAGCCCCGTGACCAAGAGC

TTCAACCGGGGCGAGTGC

SAP-E VL chimera amino acid sequence
(SEQ ID NO: 22)
DIQMTQSPASLSASVGETVTITCRASENIYSYLAWYQQKQGRSPQLLV

HNAKTLAEGVPSRVSGSGSGTHFSLKINGLQPEDFGNYYCQHHYGAPL

TFGAGTKLELKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

SAP-K VH chimera nucleotide sequence
(SEQ ID NO: 47)
CAGGTCCAACTGCAGCAGCCTGGGGCTGAGCTGATAAAGCCTGGGGCT

TCAGTGAAGTTGTCCTGCAAGGCTTCTGGCTACACTTTCACCAGCTAC

TGGATGCACTGGGTGAAGCAGAGGCCTGGACAAGGCCTTGAGTGGATT

GGAATGATTCATCCTAATAGTGTTAATACTAACTACAATGAGAAGTTC

```
                                                -continued
AAGAGTAAGGCCACACTGACTGTAGACAAATCCTCCAGCACAGCCTAC

ATGCAACTCAACAGCCTGACATCTGAGGACTCTGCGGTCTATTACTGT

GCAAGACGGAATGATTACTACTGGTACTTCGATGTCTGGGGCACAGGG

ACACTAGTGACCGTGTCCAGCGCCAGCACCAAGGGCCCCAGCGTGTTC

CCCCTGGCCCCCAGCAGCAAGAGCACCAGCGGCGGCACAGCCGCCCTG

GGCTGCCTGGTGAAGGACTACTTCCCCGAACCGGTGACCGTGTCCTGG

AACAGCGGAGCCCTGACCAGCGGCGTGCACACCTTCCCCGCCGTGCTG

CAGAGCAGCGGCCTGTACAGCCTGAGCAGCGTGGTGACCGTGCCCAGC

AGCAGCCTGGGCACCCAGACCTACATCTGTAACGTGAACCACAAGCCC

AGCAACACCAAGGTGGACAAGAAGGTGGAGCCCAAGAGCTGTGACAAG

ACCCACACCTGCCCCCCCTGCCCTGCCCCCGAGCTGCTGGGAGGCCCC

AGCGTGTTCCTGTTCCCCCCCAAGCCTAAGGACACCCTGATGATCAGC

AGAACCCCCGAGGTGACCTGTGTGGTGGTGGATGTGAGCCACGAGGAC

CCTGAGGTGAAGTTCAACTGGTACGTGGACGGCGTGGAGGTGCACAAT

GCCAAGACCAAGCCCAGGGAGGAGCAGTACAACAGCACCTACCGGGTG

GTGTCCGTGCTGACCGTGCTGCACCAGGATTGGCTGAACGGCAAGGAG

TACAAGTGTAAGGTGTCCAACAAGGCCCTGCCTGCCCCTATCGAGAAA

ACCATCAGCAAGGCCAAGGGCCAGCCCAGAGAGCCCCAGGTGTACACC

CTGCCCCCTAGCAGAGATGAGCTGACCAAGAACCAGGTGTCCCTGACC

TGCCTGGTGAAGGGCTTCTACCCCAGCGACATCGCCGTGGAGTGGGAG

AGCAACGGCCAGCCCGAGAACAACTACAAGACCACCCCCCCTGTGCTG

GACAGCGATGGCAGCTTCTTCCTGTACAGCAAGCTGACCGTGGACAAG

AGCAGATGGCAGCAGGGCAACGTGTTCAGCTGCTCCGTGATGCACGAG

GCCCTGCACAATCACTACACCCAGAAGAGCCTGAGCCTGTCCCTGGC

AAG

SAP-K VH chimera amino acid sequence
                                          (SEQ ID NO: 23)
QVQLQQPGAELIKPGASVKLSCKASGYTFTSYWMHWVKQRPGQGLEWI

GMIHPNSVNTNYNEKFKSKATLTVDKSSSTAYMQLNSLTSEDSAVYYC

ARRNDYWYFDVWGTGTLVTVSSASTKGPSVFPLAPSSKSTSGGTAAL

GCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHE

ALHNHYTQKSLSLSPGK

SAP-K VL chimera nucleotide sequence
                                          (SEQ ID NO: 48)
GACATTGTGATGACCCAGTCTCAAAAATTCATGTCCACATCAGTAGGA

GACAGGGTCAGCGTCACCTGCAAGGCCAGTCAGAATGTGAACTCTAAT

GTAGCCTGGTATCAACAGAAACCAGGGCAATCTCCTAAAGCACTGATT

TACTCGGCTTCCTACCGGTACAGTGGAGTCCCTGATCGCTTCACAGGC

AGTGGATCTGGGACAGATTTCACTCTCACCATCACCAATGTGCAGTCT

GAAGACTTGGCAGAGTATTTCTGTCAGCAATGTAACAACTATCCATTC

ACGTTCGGCTCGGGGACAAAGTTGGAAATAAAACGTACGGTGGCCGCC

CCCAGCGTGTTCATCTTCCCCCCCAGCGATGAGCAGCTGAAGAGCGGC

ACCGCCAGCGTGGTGTGTCTGCTGAACAACTTCTACCCCCGGGAGGCC

AAGGTGCAGTGGAAGGTGGACAATGCCCTGCAGAGCGGCAACAGCCAG

GAGAGCGTGACCGAGCAGGACAGCAAGGACTCCACCTACAGCCTGAGC

AGCACCCTGACCCTGAGCAAGGCCGACTACGAGAAGCACAAGGTGTAC

GCCTGTGAGGTGACCCACCAGGGCCTGTCCAGCCCCGTGACCAAGAGC

TTCAACCGGGGCGAGTGC

SAP-K VL chimera amino acid sequence
                                          (SEQ ID NO: 24)
DIVMTQSQKFMSTSVGDRVSVTCKASQNVNSNVAWYQQKPGQSPKALI

YSASYRYSGVPDRFTGSGSGTDFTLTITNVQSEDLAEYFCQQCNNYPF

TFGSGTKLEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC
```

Example 3: Humanisation Strategy

Humanised antibodies were generated by a process of grafting CDRH1, CDRH2, CDRH3, CDRL1, CDRL2 and CDRL3 from the murine antibody onto a suitable human framework sequence.

SAP-E Humanisation Strategy

SAP-E Heavy Chain Humanisation

For the SAP-E mouse variable heavy chain sequence a human germ line acceptor framework was selected (IGHV1-69, SEQ ID NO:25) which had 60% identity (including CDRs) with the mouse SAP-E variable heavy chain sequence (SEQ ID NO:7) together with the JH1 minigene (Kabat: AEYFQHWGQGTLVTVSS (SEQ ID NO:26)). The first six residues of the JH1 minigene residues fall within the CDR3 region and were replaced by the incoming CDR from the donor antibody.

Five humanised variants were generated on the basis of sequence comparison and possible impact on antibody function. Construct H0 was a straight graft of murine CDRs (using the Kabat definition) into the human acceptor framework selected above. Construct H1 has additional back-mutations at residues 27 and 30. Constructs H2 and H3 were based on H1 with additional back-mutations at residues 2 (H2), and 48 and 67 (H3). Construct H4 was based on H3 with additional back-mutations at residues 69, 73 and 91. See Table 3.

The sequences of the humanised variable heavy domains of H0, H1, H2, H3 and H4 are given below (SEQ ID NO:27, SEQ ID NO:28 SEQ ID NO:29, SEQ ID NO:30 and SEQ ID NO:31 respectively).

TABLE 3

Summary of SAP-E humanised VH variants generated

| Construct | Acceptor/template Framework | Back-mutations@ aa# (Kabat) | Total number of back-mutations | Human acceptor framework | Original mouse sequence |
|---|---|---|---|---|---|
| H0 (SEQ ID NO: 27) | IGHV1-69 (SEQ ID NO: 25) | — | — | NONE | — |
| H1 (SEQ ID NO: 28) | H0 | 27, 30 | 2 | G, S | F, A |
| H2 (SEQ ID NO: 29) | H1 | 2 | 3 | V | A |
| H3 (SEQ ID NO: 30) | H1 | 48, 67 | 4 | M, V | I, A |
| H4 (SEQ ID NO: 31) | H3 | 69, 73, 91 | 7 | I, K, Y | L, T, F |

SAP-E Light Chain Humanisation

For the SAP-E mouse variable light chain sequence a human germ line acceptor framework was selected (IGKV1-39, SEQ ID NO:32) which had 68% identity (including CDRs) with the mouse SAP-E variable light chain sequence (SEQ ID No:9) together with the J-region kappa 2 minigene (Kabat: YTFGQGTKLEIK, SEQ ID NO:33)) based on sequence similarity. The first two residues of the JK-2 minigene residues fall within the CDR3 region and were replaced by the incoming CDR from the donor antibody.

Three humanised variants were generated on the basis of sequence comparison and possible impact on antibody function. Construct L0 was a straight graft of murine CDRs (using the Kabat definition) into the human acceptor framework selected above. Construct L1 has a back-mutation at residue 49 and construct L2 has back mutations at positions 48 and 49. See Table 4.

The sequences of the humanised variable light domains of L0, L1 and L2 are given below (SEQ ID NO:34, SEQ ID NO:35 and SEQ ID NO:36 respectively).

SAP-K Humanisation Strategy

SAP-K Heavy Chain Humanisation

For the SAP-K mouse variable heavy chain sequence a human germ line acceptor framework was selected (IGHV1-69, SEQ ID NO:25) which had 65% identity (including CDRs) with the mouse SAP-K variable heavy chain sequence (SEQ ID NO:17) together with the JH1 minigene (Kabat: AEYFQHWGQGTLVTVSS (SEQ ID NO:26)). The first six residues of the JH1 minigene residues fall within the CDR3 region and were replaced by the incoming CDR from the donor antibody.

Four humanised variants were generated on the basis of sequence comparison and possible impact on antibody function. Construct H0 was a straight graft of murine CDRs (using the Kabat definition) into the human acceptor framework selected above. Construct H1 has additional back-mutations at residues 27 and 30. Construct H2 was based on H1 with additional back-mutations at residues 48 and 67. Construct H3 was based on H2 with additional back-mutations at residues 69 and 71. See Table 5.

The sequences of the humanised variable heavy domains of H0, H1, H2 and H3 are given below (SEQ ID NO:37, SEQ ID NO:38, SEQ ID NO:39 and SEQ ID NO:40 respectively).

TABLE 4

Summary of SAP-E humanised VL variants generated

| Construct | Acceptor/template Framework | Back-mutations@ aa# (Kabat) | Total number of back-mutations | Human acceptor framework | Original mouse sequence |
|---|---|---|---|---|---|
| L0 (SEQ ID NO: 34) | IGKV1-39 (SEQ ID NO: 32) | — | NONE | — | — |
| L1 (SEQ ID NO: 35) | L0 | 49 | 1 | Y | H |
| L2 (SEQ ID NO: 36) | L1 | 48, 49 | 2 | I, Y | V, H |

TABLE 5

Summary of SAP-K humanised VH variants generated

| Construct | Acceptor/template Framework | Back-mutations@ aa# (Kabat) | Total number of back-mutations | Human acceptor framework | Original mouse sequence |
|---|---|---|---|---|---|
| H0 (SEQ ID NO: 37) | IGHV1-69 (SEQ ID NO: 25) | — | NONE | — | — |
| H1 (SEQ ID NO: 38) | H0 | 27 30 | 2 | G S | Y T |
| H2 (SEQ ID NO: 39) | H1 | 48 67 | 4 | M V | I A |
| H3 (SEQ ID NO: 40) | H2 | 69 71 | 6 | I A | L V |

SAP-K Light Chain Humanisation

For the SAP-K mouse variable light chain sequence a human germ line acceptor framework was selected (IGKV1-39, SEQ ID NO:32) which had 63% identity (including CDRs) with the mouse SAP-K variable light chain sequence (SEQ ID NO:19) together with the J-region kappa 2 minigene (Kabat: YTFGQGTKLEIK, SEQ ID NO:33) based on sequence similarity. The first two residues of the JK-2 minigene residues fall within the CDR3 region and were replaced by the incoming CDR from the donor antibody.

Two humanised variants were generated on the basis of sequence comparison and possible impact on antibody function. Construct L0 was a straight graft of murine CDRs (using the Kabat definition) into the human acceptor framework selected above. Construct L1 has a back-mutation at residue 46.

The sequences of the humanised variable light domains of L0 and L1 are given below (SEQ ID NO:41 and SEQ ID NO:42 respectively).

TABLE 6

Summary of SAP-K humanised VL variants generated

| Construct | Acceptor/template Framework | Back-mutations@ aa# (Kabat) | Total number of back-mutations | Human acceptor framework | Original mouse sequence |
|---|---|---|---|---|---|
| L0 (SEQ ID NO: 41) | IGKV1-39 (SEQ ID NO: 32) | — | NONE | — | — |
| L1 (SEQ ID NO: 42) | L0 | 46 | 1 | L | A |

Construction of Humanised Antibody Vectors

The humanised variable region DNA sequences were sequence optimised. DNA fragments encoding the humanised variable heavy and variable light regions were constructed de novo using a PCR-based strategy and overlapping oligonucleotides. The PCR product was cloned into mammalian expression vectors containing the human gamma 1 constant region and the human kappa constant region respectively. This is the wild-type Fc region.

IGHV1-69 human variable heavy chain germline acceptor nucleotide sequence
(SEQ ID NO: 49)
CAGGTGCAGCTGGTGCAGTCTGGGGCTGAGGTGAAGAAGCCTGGGTCC

TCGGTGAAGGTCTCCTGCAAGGCTTCTGGAGGCACCTTCAGCAGCTAT

GCTATCAGCTGGGTGCGACAGGCCCCTGGACAAGGGCTTGAGTGGATG

GGAGGGATCATCCCTATCTTTGGTACAGCAAACTACGCACAGAAGTTC

CAGGGCAGAGTCACGATTACCGCGGACAAATCCACGAGCACAGCCTAC

ATGGAGCTGAGCAGCCTGAGATCTGAGGACACGGCCGTGTATTACTGT

GCGAGA

IGHV1-69 human variable heavy chain germline acceptor amino acid sequence
(SEQ ID NO: 25)
QVQLVQSGAEVKKPGSSVKVSCKASGGTFSSYAISWVRQAPGQGLEWM

GGIIPIFGTANYAQKFQGRVTITADKSTSTAYMELSSLRSEDTAVYYC

AR

IGKV1-39 human variable heavy chain germline acceptor nucleotide sequence
(SEQ ID NO: 50)
GACATCCAGATGACCCAGTCTCCATCCTCCCTGTCTGCATCTGTAGGA

GACAGAGTCACCATCACTTGCCGGGCAAGTCAGAGCATTAGCAGCTAT

TTAAATTGGTATCAGCAGAAACCAGGGAAAGCCCCTAAGCTCCTGATC

TATGCTGCATCCAGTTTGCAAAGTGGGGTCCCATCAAGGTTCAGTGGC

AGTGGATCTGGGACAGATTTCACTCTCACCATCAGCAGTCTGCAACCT

GAAGATTTTGCAACTTACTACTGTCAACAGAGTTACAGTACCCCT

IGKV1-39 human variable heavy chain germline acceptor amino acid sequence
(SEQ ID NO: 32)
DIQMTQSPSSLSASVGDRVTITCRASQSISSYLNWYQQKPGKAPKLLI

YAASSLQSGVPSRFSGSGSGTDFTLTISSLQPEDFATYYCQQSYSTP

JH1 minigene
(SEQ ID NO: 26)
AEYFQHWGQGTLVTVSS

Jκ2 minigene
(SEQ ID NO: 33)
YTFGQGTKLEIK

SAP-E humanised heavy chain V region variant H0
nucleotide sequence non-codon optimised
(SEQ ID NO: 51)
CAGGTGCAGCTGGTGCAGTCTGGGGCTGAGGTGAAGAAGCCTGGGTCC

TCGGTGAAGGTCTCCTGCAAGGCTTCTGGAGGCACCTTCAGCACTTAC

AATATGCACTGGGTGCGACAGGCCCCTGGACAAGGGCTTGAGTGGATG

GGATATATTTATCCTGGAGATGGTAATGCTAACTACAATCAGCAGTTC

AAGGGCAGAGTCACGATTACCGCGGACAAATCCACGAGCACAGCCTAC

ATGGAGCTGAGCAGCCTGAGATCTGAGGACACGGCCGTGTATTACTGT

GCGAGAGGGGACTTTGATTACGACGGAGGGTACTACTTTGACTCCTGG

GGCCAGGGCACCCTGGTCACCGTCTCCTCA

SAP-E humanised light chain V region variant L0
nucleotide sequence non-codon optimised
(SEQ ID NO: 52)
GACATCCAGATGACCCAGTCTCCATCCTCCCTGTCTGCATCTGTAGGA

GACAGAGTCACCATCACTTGCCGAGCAAGTGAGAATATTTACAGTTAT

TTAGCATGGTATCAGCAGAAACCAGGGAAAGCCCCTAAGCTCCTGATC

TATAATGCAAAAACCTTAGCAGAAGGGGTCCCATCAAGGTTCAGTGGC

AGTGGATCTGGGACAGATTTCACTCTCACCATCAGCAGTCTGCAACCT

GAAGATTTTGCAACTTACTACTGTCAACATCATTATGGTGCTCCGCTC

ACGTTTGGCCAGGGGACCAAGCTGGAGATCAAA

SAP-E humanised heavy chain V region variant H0
nucleotide sequence (codon optimised)
(SEQ ID NO: 53)
CAGGTGCAGCTGGTGCAGAGCGGCGCCGAGGTGAAGAAACCCGGCAGC

AGCGTGAAGGTGAGCTGCAAGGCTAGCGGGGGCACCTTCTCCACCTAC

AACATGCACTGGGTCAGGCAGGCACCCGGCCAGGGCCTGGAGTGGATG

GGCTATATCTACCCCGGCGACGGCAACGCCAACTACAACCAGCAGTTC

AAGGGCAGGGTGACCATCACCGCCGACAAGAGCACCAGCACCGCCTAC

ATGGAACTGAGCAGCCTGAGGAGCGAGGATACCGCCGTGTACTACTGC

GCCAGGGGCGACTTCGACTACGACGGCGGCTACTACTTCGACAGCTGG

GGACAGGGCACACTAGTGACCGTGTCCAGC

SAP-E humanised heavy chain V region variant H0
amino acid sequence
(SEQ ID NO: 27)
QVQLVQSGAEVKKPGSSVKVSCKASGGTFSTYNMHWVRQAPGQGLEWM

GYIYPGDGNANYNQQFKGRVTITADKSTSTAYMELSSLRSEDTAVYYC

ARGDFDYDGGYYFDSWGQGTLVTVSS

SAP-E humanised heavy chain V region variant H1
nucleotide sequence (codon optimised)
(SEQ ID NO: 54)
CAGGTGCAGCTGGTGCAGAGCGGCGCCGAGGTGAAGAAACCCGGCAGC

AGCGTGAAGGTGAGCTGCAAGGCTAGCGGGTTCACCTTCGCCACCTAC

AACATGCACTGGGTCAGGCAGGCACCCGGCCAGGGCCTGGAGTGGATG

GGCTATATCTACCCCGGCGACGGCAACGCCAACTACAACCAGCAGTTC

AAGGGCAGGGTGACCATCACCGCCGACAAGAGCACCAGCACCGCCTAC

ATGGAACTGAGCAGCCTGAGGAGCGAGGATACCGCCGTGTACTACTGC

GCCAGGGGCGACTTCGACTACGACGGCGGCTACTACTTCGACAGCTGG

GGACAGGGCACACTAGTGACCGTGTCCAGC

SAP-E humanised heavy chain V region variant H1
amino acid sequence
(SEQ ID NO: 28)
QVQLVQSGAEVKKPGSSVKVSCKASGFTFATYNMHWVRQAPGQGLEWM

GYIYPGDGNANYNQQFKGRVTITADKSTSTAYMELSSLRSEDTAVYYC

ARGDFDYDGGYYFDSWGQGTLVTVSS

SAP-E humanised heavy chain V region variant H2
nucleotide sequence (codon optimised)
(SEQ ID NO: 55)
CAGGCGCAGCTGGTGCAGAGCGGCGCCGAGGTGAAGAAACCCGGCAGC

AGCGTGAAGGTGAGCTGCAAGGCTAGCGGGTTCACCTTCGCCACCTAC

AACATGCACTGGGTCAGGCAGGCACCCGGCCAGGGCCTGGAGTGGATG

GGCTATATCTACCCCGGCGACGGCAACGCCAACTACAACCAGCAGTTC

AAGGGCAGGGTGACCATCACCGCCGACAAGAGCACCAGCACCGCCTAC

ATGGAACTGAGCAGCCTGAGGAGCGAGGATACCGCCGTGTACTACTGC

GCCAGGGGCGACTTCGACTACGACGGCGGCTACTACTTCGACAGCTGG

GGACAGGGCACACTAGTGACCGTGTCCAGC

SAP-E humanised heavy chain V region variant H2
amino acid sequence
SEQ ID NO: 29
QAQLVQSGAEVKKPGSSVKVSCKASGFTFATYNMHWVRQAPGQGLEWM

GYIYPGDGNANYNQQFKGRVTITADKSTSTAYMELSSLRSEDTAVYYC

ARGDFDYDGGYYFDSWGQGTLVTVSS

SAP-E humanised heavy chain V region variant H3
nucleotide sequence (codon optimised)
(SEQ ID NO: 56)
CAGGTGCAGCTGGTGCAGAGCGGCGCCGAGGTGAAGAAACCCGGCAGC

AGCGTGAAGGTGAGCTGCAAGGCTAGCGGGTTCACCTTCGCCACCTAC

AACATGCACTGGGTCAGGCAGGCACCCGGCCAGGGCCTGGAGTGGATC

GGCTATATCTACCCCGGCGACGGCAACGCCAACTACAACCAGCAGTTC

AAGGGCAGGGCCACCATCACCGCCGACAAGAGCACCAGCACCGCCTAC

ATGGAACTGAGCAGCCTGAGGAGCGAGGATACCGCCGTGTACTACTGC

GCCAGGGGCGACTTCGACTACGACGGCGGCTACTACTTCGACAGCTGG

GGACAGGGCACACTAGTGACCGTGTCCAGC

SAP-E humanised heavy chain V region variant H3
amino acid sequence
(SEQ ID NO: 30)
QVQLVQSGAEVKKPGSSVKVSCKASGFTFATYNMHWVRQAPGQGLEWI

GYIYPGDGNANYNQQFKGRATITADKSTSTAYMELSSLRSEDTAVYYC

ARGDFDYDGGYYFDSWGQGTLVTVSS

SAP-E humanised heavy chain V region variant H4
nucleotide sequence (codon optimised)
(SEQ ID NO: 57)
CAGGTGCAGCTGGTGCAGAGCGGCGCCGAGGTGAAGAAACCCGGCAGC

AGCGTGAAGGTGAGCTGCAAGGCTAGCGGGTTCACCTTCGCCACCTAC

AACATGCACTGGGTCAGGCAGGCACCCGGCCAGGGCCTGGAGTGGATC

GGCTATATCTACCCCGGCGACGGCAACGCCAACTACAACCAGCAGTTC

```
AAGGGCAGGGCCACCCTGACCGCCGACACCAGCACCAGCACCGCCTAC

ATGGAACTGAGCAGCCTGAGGAGCGAGGATACCGCCGTGTACTTCTGC

GCCAGGGGCGACTTCGACTACGACGGCGGCTACTACTTCGACAGCTGG

GGACAGGGCACACTAGTGACCGTGTCCAGC
```

SAP-E humanised heavy chain V region variant H4
amino acid sequence
(SEQ ID NO: 31)
QVQLVQSGAEVKKPGSSVKVSCKASGFTFATYNMHWVRQAPGQGLEWI

GYIYPGDGNANYNQQFKGRATLTADTSTSTAYMELSSLRSEDTAVYFC

ARGDFDYDGGYYFDSWGQGTLVTVSS

SAP-E humanised light chain V region variant L0
nucleotide sequence (codon optimised)
(SEQ ID NO: 58)
```
GACATCCAGATGACCCAGAGCCCCAGCTCACTGAGCGCCAGCGTGGGC

GACAGGGTGACCATTACCTGCAGGGCCTCCGAGAACATCTACAGCTAC

CTGGCCTGGTACCAGCAGAAGCCCGGCAAGGCCCCCAAGCTGCTGATC

TACAACGCCAAGACCCTCGCCGAGGGCGTCCCTAGCAGGTTCTCTGGA

AGCGGCAGCGGCACCGACTTCACCCTGACCATCAGCAGCCTGCAGCCC

GAGGACTTCGCCACCTATTACTGCCAGCACCACTACGGCGCCCCCCTG

ACCTTTGGCCAGGGCACCAAACTGGAGATCAAG
```

SAP-E humanised light chain V region variant L0
amino acid sequence
SEQ ID NO: 34
DIQMTQSPSSLSASVGDRVTITCRASENIYSYLAWYQQKPGKAPKLLI

YNAKTLAEGVPSRFSGSGSGTDFTLTISSLQPEDFATYYCQHHYGAPL

TFGQGTKLEIK

SAP-E humanised light chain V region variant L1
nucleotide sequence (codon optimised)
(SEQ ID NO: 59)
```
GACATCCAGATGACCCAGAGCCCCAGCTCACTGAGCGCCAGCGTGGGC

GACAGGGTGACCATTACCTGCAGGGCCTCCGAGAACATCTACAGCTAC

CTGGCCTGGTACCAGCAGAAGCCCGGCAAGGCCCCCAAGCTGCTGATC

CACAACGCCAAGACCCTCGCCGAGGGCGTCCCTAGCAGGTTCTCTGGA

AGCGGCAGCGGCACCGACTTCACCCTGACCATCAGCAGCCTGCAGCCC

GAGGACTTCGCCACCTATTACTGCCAGCACCACTACGGCGCCCCCCTG

ACCTTTGGCCAGGGCACCAAACTGGAGATCAAG
```

SAP-E humanised light chain V region variant L1
amino acid sequence
(SEQ ID NO: 35)
DIQMTQSPSSLSASVGDRVTITCRASENIYSYLAWYQQKPGKAPKLLI

HNAKTLAEGVPSRFSGSGSGTDFTLTISSLQPEDFATYYCQHHYGAPL

TFGQGTKLEIK

SAP-E humanised light chain V region variant L2
nucleotide sequence (codon optimised)
(SEQ ID NO: 60)
```
GACATCCAGATGACCCAGAGCCCCAGCTCACTGAGCGCCAGCGTGGGC

GACAGGGTGACCATTACCTGCAGGGCCTCCGAGAACATCTACAGCTAC

CTGGCCTGGTACCAGCAGAAGCCCGGCAAGGCCCCCAAGCTGCTGGTG

CACAACGCCAAGACCCTCGCCGAGGGCGTCCCTAGCAGGTTCTCTGGA

AGCGGCAGCGGCACCGACTTCACCCTGACCATCAGCAGCCTGCAGCCC

GAGGACTTCGCCACCTATTACTGCCAGCACCACTACGGCGCCCCCCTG

ACCTTTGGCCAGGGCACCAAACTGGAGATCAAG
```

SAP-E humanised light chain V region variant L2
amino acid sequence
(SEQ ID NO: 36)
DIQMTQSPSSLSASVGDRVTITCRASENIYSYLAWYQQKPGKAPKLLV

HNAKTLAEGVPSRFSGSGSGTDFTLTISSLQPEDFATYYCQHHYGAPL

TFGQGTKLEIK

SAP-E humanised heavy chain H1 full mature
nucleotide sequence (codon optimised)
(SEQ ID NO: 61)
```
CAGGTGCAGCTGGTGCAGAGCGGCGCCGAGGTGAAGAAACCCGGCAGC

AGCGTGAAGGTGAGCTGCAAGGCTAGCGGGTTCACCTTCGCCACCTAC

AACATGCACTGGGTCAGGCAGGCACCCGGCCAGGGCCTGGAGTGGATG

GGCTATATCTACCCCGGCGACGGCAACGCCAACTACAACCAGCAGTTC

AAGGGCAGGGTGACCATCACCGCCGACAAGAGCACCAGCACCGCCTAC

ATGGAACTGAGCAGCCTGAGGAGCGAGGATACCGCCGTGTACTACTGC

GCCAGGGGCGACTTCGACTACGACGGCGGCTACTACTTCGACAGCTGG

GGACAGGGCACACTAGTGACCGTGTCCAGCGCCAGCACCAAGGGCCCC

AGCGTGTTCCCCCTGGCCCCCAGCAGCAAGAGCACCAGCGGCGGCACA

GCCGCCCTGGGCTGCCTGGTGAAGGACTACTTCCCCGAACCGGTGACC

GTGTCCTGGAACAGCGGAGCCCTGACCAGCGGCGTGCACACCTTCCCC

GCCGTGCTGCAGAGCAGCGGCCTGTACAGCCTGAGCAGCGTGGTGACC

GTGCCCAGCAGCAGCCTGGGCACCCAGACCTACATCTGTAACGTGAAC

CACAAGCCCAGCAACACCAAGGTGGACAAGAAGGTGGAGCCCAAGAGC

TGTGACAAGACCCACACCTGCCCCCCCTGCCCTGCCCCCGAGCTGCTG

GGAGGCCCCAGCGTGTTCCTGTTCCCCCCCAAGCCTAAGGACACCCTG

ATGATCAGCAGAACCCCCGAGGTGACCTGTGTGGTGGTGGATGTGAGC

CACGAGGACCCTGAGGTGAAGTTCAACTGGTACGTGGACGGCGTGGAG

GTGCACAATGCCAAGACCAAGCCCAGGGAGGAGCAGTACAACAGCACC

TACCGGGTGGTGTCCGTGCTGACCGTGCTGCACCAGGATTGGCTGAAC

GGCAAGGAGTACAAGTGTAAGGTGTCCAACAAGGCCCTGCCTGCCCCT

ATCGAGAAAACCATCAGCAAGGCCAAGGGCCAGCCCAGAGAGCCCCAG

GTGTACACCCTGCCCCCTAGCAGAGATGAGCTGACCAAGAACCAGGTG

TCCCTGACCTGCCTGGTGAAGGGCTTCTACCCCAGCGACATCGCCGTG

GAGTGGGAGAGCAACGGCCAGCCCGAGAACAACTACAAGACCACCCCC

CCTGTGCTGGACAGCGATGGCAGCTTCTTCCTGTACAGCAAGCTGACC

GTGGACAAGAGCAGATGGCAGCAGGGCAACGTGTTCAGCTGCTCCGTG

ATGCACGAGGCCCTGCACAATCACTACACCCAGAAGAGCCTGAGCCTG

TCCCCTGGCAAG
```

SAP-E humanised heavy chain H1 full mature amino
acid sequence
(SEQ ID NO: 62)
QVQLVQSGAEVKKPGSSVKVSCKASGFTFATYNMHWVRQAPGQGLEWM
GYIYPGDGNANYNQQFKGRVTITADKSTSTAYMELSSLRSEDTAVYYC
ARGDFDYDGGYYFDSWGQGTLVTVSSASTKGPSVFPLAPSSKSTSGGT
AALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSV
MHEALHNHYTQKSLSLSPGK SAP-E humanised light chain L1 full mature
nucleotide sequence (codon optimised)
(SEQ ID NO: 63)
GACATCCAGATGACCCAGAGCCCCAGCTCACTGAGCGCCAGCGTGGGC
GACAGGGTGACCATTACCTGCAGGGCCTCCGAGAACATCTACAGCTAC
CTGGCCTGGTACCAGCAGAAGCCCGGCAAGGCCCCCAAGCTGCTGATC
CACAACGCCAAGACCCTCGCCGAGGGCGTCCCTAGCAGGTTCTCTGGA
AGCGGCAGCGGCACCGACTTCACCCTGACCATCAGCAGCCTGCAGCCC
GAGGACTTCGCCACCTATTACTGCCAGCACCACTACGGCGCCCCCCTG
ACCTTTGGCCAGGGCACCAAACTGGAGATCAAGCGTACGGTGGCCGCC
CCCAGCGTGTTCATCTTCCCCCCCAGCGATGAGCAGCTGAAGAGCGGC
ACCGCCAGCGTGGTGTGTCTGCTGAACAACTTCTACCCCCGGGAGGCC
AAGGTGCAGTGGAAGGTGGACAATGCCCTGCAGAGCGGCAACAGCCAG
GAGAGCGTGACCGAGCAGGACAGCAAGGACTCCACCTACAGCCTGAGC
AGCACCCTGACCCTGAGCAAGGCCGACTACGAGAAGCACAAGGTGTAC
GCCTGTGAGGTGACCCACCAGGGCCTGTCCAGCCCCGTGACCAAGAGC
TTCAACCGGGGCGAGTGC SAP-E humanised light chain L1 full mature amino
acid sequence
(SEQ ID NO: 64)
DIQMTQSPSSLSASVGDRVTITCRASENIYSYLAWYQQKPGKAPKLLI
HNAKTLAEGVPSRFSGSGSGTDFTLTISSLQPEDFATYYCQHHYGAPL
TFGQGTKLEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKSFNRGEC SAP-K humanised heavy chain V region variant H0
nucleotide sequence non-codon
optimised
(SEQ ID NO: 65)
CAGGTGCAGCTGGTGCAGTCTGGGGCTGAGGTGAAGAAGCCTGGGTCC
TCGGTGAAGGTCTCCTGCAAGGCTTCTGGAGGCACCTTCAGCAGCTAC
TGGATGCACTGGGTGCGACAGGCCCCTGGACAAGGGCTTGAGTGGATG
GGAATGATTCATCCTAATAGTGTTAATACTAACTACAATGAAGAGTTC
AAGAGTAGAGTCACGATTACCGCGGACAAATCCACGAGCACAGCCTAC
ATGGAGCTGAGCAGCCTGAGATCTGAGGACACGGCCGTGTATTACTGT
GCGAGACGGAATGATTACTACTGGTACTTCGATGTCTGGGGCCAGGGC
ACCCTGGTCACCGTCTCCTCA SAP-K humanised light chain V region variant L0
nucleotide sequence non-codon optimised
(SEQ ID NO: 66)
GACATCCAGATGACCCAGTCTCCATCCTCCCTGTCTGCATCTGTAGGA
GACAGAGTCACCATCACTTGCAAGGCCAGTCAGAATGTGAACTCTAAT
GTAGCCTGGTATCAGCAGAAACCAGGGAAAGCCCCTAAGCTCCTGATC
TATTCGGCTTCCTACCGGTACAGTGGGGTCCCATCAAGGTTCAGTGGC
AGTGGATCTGGGACAGATTTCACTCTCACCATCAGCAGTCTGCAACCT
GAAGATTTTGCAACTTACTACTGTCAGCAATGTAACAACTATCCATTC
ACGTTTGGCCAGGGGACCAAGCTGGAGATCAAA SAP-K humanised heavy chain V region variant H0
nucleotide sequence (codon optimised)
(SEQ IS NO: 67)
CAGGTGCAGCTGGTGCAGAGCGGCGCCGAAGTGAAGAAGCCCGGCAGC
AGCGTGAAAGTGAGCTGCAAGGCCAGCGGCGGAACCTTCAGCAGCTAC
TGGATGCACTGGGTGAGGCAGGCACCCGGCCAGGGCCTGGAGTGGATG
GGCATGATCCACCCCAACAGCGTGAACACCAACTACAACGAGAAGTTC
AAGAGCAGAGTGACCATCACCGCCGACAAGAGCACCAGCACCGCCTAT
ATGGAGCTGAGCTCTCTGAGGAGCGAGGATACCGCCGTGTACTACTGC
GCCAGGAGGAACGACTACTACTGGTACTTCGACGTCTGGGGCCAGGGC
ACACTAGTGACCGTGTCCAGC SAP-K humanised heavy chain V region variant H0
amino acid sequence
(SEQ ID NO: 37)
QVQLVQSGAEVKKPGSSVKVSCKASGGTFSSYWMHWVRQAPGQGLEWM
GMIHPNSVNTNYNEKFKSRVTITADKSTSTAYMELSSLRSEDTAVYYC
ARRNDYYWYFDVWGQGTLVTVSS SAP-K humanised heavy chain V region variant H1
nucleotide sequence (codon optimised)
(SEQ ID NO: 68)
CAGGTGCAGCTGGTGCAGAGCGGCGCCGAAGTGAAGAAGCCCGGCAGC
AGCGTGAAAGTGAGCTGCAAGGCCAGCGGCTACACCTTCACCAGCTAC
TGGATGCACTGGGTGAGGCAGGCACCCGGCCAGGGCCTGGAGTGGATG
GGCATGATCCACCCCAACAGCGTGAACACCAACTACAACGAGAAGTTC
AAGAGCAGAGTGACCATCACCGCCGACAAGAGCACCAGCACCGCCTAT
ATGGAGCTGAGCTCTCTGAGGAGCGAGGATACCGCCGTGTACTACTGC
GCCAGGAGGAACGACTACTACTGGTACTTCGACGTCTGGGGCCAGGGC
ACACTAGTGACCGTGTCCAGC SAP-K humanised heavy chain V region variant H1
amino acid sequence
(SEQ ID NO: 38)
QVQLVQSGAEVKKPGSSVKVSCKASGYTFTSYWMHWVRQAPGQGLEWM
GMIHPNSVNTNYNEKFKSRVTITADKSTSTAYMELSSLRSEDTAVYYC
ARRNDYYWYFDVWGQGTLVTVSS SAP-K humanised heavy chain V region variant H2
nucleotide sequence (codon optimised)
(SEQ ID NO: 69)
CAGGTGCAGCTGGTGCAGAGCGGCGCCGAAGTGAAGAAGCCCGGCAGC

AGCGTGAAAGTGAGCTGCAAGGCCAGCGGCTACACCTTCACCAGCTAC

TGGATGCACTGGGTGAGGCAGGCACCCGGCCAGGGCCTGGAGTGGATC

GGCATGATCCACCCCAACAGCGTGAACACCAACTACAACGAGAAGTTC

AAGAGCAGAGCCACCATCACCGCCGACAAGAGCACCAGCACCGCCTAT

ATGGAGCTGAGCTCTCTGAGGAGCGAGGATACCGCCGTGTACTACTGC

GCCAGGAGGAACGACTACTACTGGTACTTCGACGTCTGGGGCCAGGGC

ACACTAGTGACCGTGTCCAGC

SAP-K humanised heavy chain V region variant H2
amino acid sequence
(SEQ ID NO: 39)
QVQLVQSGAEVKKPGSSVKVSCKASGYTFTSYWMHWVRQAPGQGLEWI

GMIHPNSVNTNYNEKFKSRATITADKSTSTAYMELSSLRSEDTAVYYC

ARRNDYYWYFDVWGQGTLVTVSS

SAP-K humanised heavy chain V region variant H3
nucleotide sequence (codon optimised)
(SEQ ID NO: 70)
CAGGTGCAGCTGGTGCAGAGCGGCGCCGAAGTGAAGAAGCCCGGCAGC

AGCGTGAAAGTGAGCTGCAAGGCCAGCGGCTACACCTTCACCAGCTAC

TGGATGCACTGGGTGAGGCAGGCACCCGGCCAGGGCCTGGAGTGGATC

GGCATGATCCACCCCAACAGCGTGAACACCAACTACAACGAGAAGTTC

AAGAGCAGAGCCACCCTGACCGTGGACAAGAGCACCAGCACCGCCTAT

ATGGAGCTGAGCTCTCTGAGGAGCGAGGATACCGCCGTGTACTACTGC

GCCAGGAGGAACGACTACTACTGGTACTTCGACGTCTGGGGCCAGGGC

ACACTAGTGACCGTGTCCAGC

SAP-K humanised heavy chain V region variant H3
amino acid sequence
(SEQ ID NO: 40)
QVQLVQSGAEVKKPGSSVKVSCKASGYTFTSYWMHWVRQAPGQGLEWI

GMIHPNSVNTNYNEKFKSRATLTVDKSTSTAYMELSSLRSEDTAVYYC

ARRNDYYWYFDVWGQGTLVTVSS

SAP-K humanised light chain V region variant L0
nucleotide sequence (codon optimised)
SEQ ID NO: 71)
GACATCCAGATGACCCAGAGCCCCTCTTCACTGAGCGCTAGCGTGGGC

GACAGGGTGACCATCACCTGCAAGGCCAGCCAGAACGTGAACAGCAAC

GTGGCCTGGTACCAGCAGAAGCCCGGCAAAGCCCCCAAGCTCCTGATC

TACAGCGCCAGCTACAGATATAGCGGCGTGCCTAGCAGGTTTAGCGGC

AGCGGAAGCGGGACCGATTTCACCCTGACCATCAGCAGCCTGCAGCCC

GAGGACTTCGCCACTTACTACTGCCAGCAGTGCAACAACTACCCCTTC

ACCTTCGGCCAGGGCACCAAGCTGGAGATCAAG

SAP-K humanised light chain V region variant L0
amino acid sequence
(SEQ ID NO: 41)
DIQMTQSPSSLSASVGDRVTITCKASQNVNSNVAWYQQKPGKAPKLLI

YSASYRYSGVPSRFSGSGSGTDFTLTISSLQPEDFATYYCQQCNNYPF

TFGQGTKLEIK

SAP-K humanised light chain V region variant L1
nucleotide sequence (codon optimised)
(SEQ ID NO: 72)
GACATCCAGATGACCCAGAGCCCCTCTTCACTGAGCGCTAGCGTGGGC

GACAGGGTGACCATCACCTGCAAGGCCAGCCAGAACGTGAACAGCAAC

GTGGCCTGGTACCAGCAGAAGCCCGGCAAAGCCCCCAAGGCCCTGATC

TACAGCGCCAGCTACAGATATAGCGGCGTGCCTAGCAGGTTTAGCGGC

AGCGGAAGCGGGACCGATTTCACCCTGACCATCAGCAGCCTGCAGCCC

GAGGACTTCGCCACTTACTACTGCCAGCAGTGCAACAACTACCCCTTC

ACCTTCGGCCAGGGCACCAAGCTGGAGATCAAG

SAP-K humanised light chain V region variant L1
amino acid sequence
(SEQ ID NO: 42)
DIQMTQSPSSLSASVGDRVTITCKASQNVNSNVAWYQQKPGKAPKALI

YSASYRYSGVPSRFSGSGSGTDFTLTISSLQPEDFATYYCQQCNNYPF

TFGQGTKLEIK

SAP-K humanised H3 heavy chain nucleotide
sequence (codon optimised)
(SEQ ID NO: 75)
CAGGTGCAGCTGGTGCAGAGCGGCGCCGAAGTGAAGAAGCCCGGCAGC

AGCGTGAAAGTGAGCTGCAAGGCCAGCGGCTACACCTTCACCAGCTAC

TGGATGCACTGGGTGAGGCAGGCACCCGGCCAGGGCCTGGAGTGGATC

GGCATGATCCACCCCAACAGCGTGAACACCAACTACAACGAGAAGTTC

AAGAGCAGAGCCACCCTGACCGTGGACAAGAGCACCAGCACCGCCTAT

ATGGAGCTGAGCTCTCTGAGGAGCGAGGATACCGCCGTGTACTACTGC

GCCAGGAGGAACGACTACTACTGGTACTTCGACGTCTGGGGCCAGGGC

ACACTAGTGACCGTGTCCAGCGCCAGCACCAAGGGCCCCAGCGTGTTC

CCCCTGGCCCCCAGCAGCAAGAGCACCAGCGGCGGCACAGCCGCCCTG

GGCTGCCTGGTGAAGGACTACTTCCCCGAACCGGTGACCGTGTCCTGG

AACAGCGGAGCCCTGACCAGCGGCGTGCACACCTTCCCCGCCGTGCTG

CAGAGCAGCGGCCTGTACAGCCTGAGCAGCGTGGTGACCGTGCCCAGC

AGCAGCCTGGGCACCCAGACCTACATCTGTAACGTGAACCACAAGCCC

AGCAACACCAAGGTGGACAAGAAGGTGGAGCCCAAGAGCTGTGACAAG

ACCCACACCTGCCCCCCCTGCCCTGCCCCCGAGCTGCTGGGAGGCCCC

AGCGTGTTCCTGTTCCCCCCCAAGCCTAAGGACACCCTGATGATCAGC

AGAACCCCCGAGGTGACCTGTGTGGTGGTGGATGTGAGCCACGAGGAC

CCTGAGGTGAAGTTCAACTGGTACGTGGACGGCGTGGAGGTGCACAAT

GCCAAGACCAAGCCCAGGGAGGAGCAGTACAACAGCACCTACCGGGTG

GTGTCCGTGCTGACCGTGCTGCACCAGGATTGGCTGAACGGCAAGGAG

TACAAGTGTAAGGTGTCCAACAAGGCCCTGCCTGCCCCTATCGAGAAA

ACCATCAGCAAGGCCAAGGGCCAGCCCAGAGAGCCCCAGGTGTACACC

CTGCCCCCTAGCAGAGATGAGCTGACCAAGAACCAGGTGTCCCTGACC

TGCCTGGTGAAGGGCTTCTACCCCAGCGACATCGCCGTGGAGTGGGAG

AGCAACGGCCAGCCCGAGAACAACTACAAGACCACCCCCCCTGTGCTG

GACAGCGATGGCAGCTTCTTCCTGTACAGCAAGCTGACCGTGGACAAG

-continued

AGCAGATGGCAGCAGGGCAACGTGTTCAGCTGCTCCGTGATGCACGAG

GCCCTGCACAATCACTACACCCAGAAGAGCCTGAGCCTGTCCCCTGGC

AAG

SAP-K humanised H3 heavy chain amino acid
sequence
(SEQ ID NO: 76)
QVQLVQSGAEVKKPGSSVKVSCKASGYTFTSYWMHWVRQAPGQGLEWI

GMIHPNSVNTNYNEKFKSRATLTVDKSTSTAYMELSSLRSEDTAVYYC

ARRNDYYWYFDVWGQGTLVTVSSASTKGPSVFPLAPSSKSTSGGTAAL

GCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHE

ALHNHYTQKSLSLSPGK

SAP-K humanised L0 light chain nucleotide
sequence (codon optimised)
(SEQ ID NO: 77)
GACATCCAGATGACCCAGAGCCCCTCTTCACTGAGCGCTAGCGTGGGC

GACAGGGTGACCATCACCTGCAAGGCCAGCCAGAACGTGAACAGCAAC

GTGGCCTGGTACCAGCAGAAGCCCGGCAAAGCCCCCAAGCTCCTGATC

TACAGCGCCAGCTACAGATATAGCGGCGTGCCTAGCAGGTTTAGCGGC

AGCGGAAGCGGGACCGATTTCACCCTGACCATCAGCAGCCTGCAGCCC

GAGGACTTCGCCACTTACTACTGCCAGCAGTGCAACAACTACCCCTTC

ACCTTCGGCCAGGGCACCAAGCTGGAGATCAAGCGTACGGTGGCCGCC

CCCAGCGTGTTCATCTTCCCCCCCAGCGATGAGCAGCTGAAGAGCGGC

ACCGCCAGCGTGGTGTGTCTGCTGAACAACTTCTACCCCCGGGAGGCC

AAGGTGCAGTGGAAGGTGGACAATGCCCTGCAGAGCGGCAACAGCCAG

GAGAGCGTGACCGAGCAGGACAGCAAGGACTCCACCTACAGCCTGAGC

AGCACCCTGACCCTGAGCAAGGCCGACTACGAGAAGCACAAGGTGTAC

GCCTGTGAGGTGACCCACCAGGGCCTGTCCAGCCCCGTGACCAAGAGC

TTCAACCGGGGCGAGTGC

SAP-K humanised L0 light chain amino acid
sequence
(SEQ ID NO: 78)
DIQMTQSPSSLSASVGDRVTITCKASQNVNSNVAWYQQKPGKAPKLLI

YSASYRYSGVPSRFSGSGSGTDFTLTISSLQPEDFATYYCQQCNNYPF

TFGQGTKLEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

Leader sequence for immunoglobulin chains
(SEQ ID: 79)
MGWSCIILFLVATATGVHS

Example 4:—Antibody Expression

Recombinant Antibody Expression

Expression plasmids encoding the heavy and light chains respectively of chimeric or humanised antibodies were transiently co-transfected into HEK2936E cells by lipid transfection using Fectin 293. Cells were grown in Freestyle expression media 293 with 10% pluronic F68 and 50 mg/ml geneticin, 37 degrees C., 5% CO2 for 72-120 hrs, supernatant was harvested by centrifugation. In some instances the supernatant material was used as the test article in binding assays. In other instances, the supernatant material was filter sterilised and the antibody recovered by affinity chromatography using Protein A MAbSelect SuRE column followed by dialysis into PBS.

Hybridoma Antibody Expression

The hybridoma cells were grown in shake flasks in Ex620 medium supplemented with 4 mM glutamax and 10% low IgG FCS. The cells were passaged and weaned off serum until growing well in serum free medium. The cells were then used as a seed for a 10 L wavebag. The cells were grown in the wavebag at 22 rocks/min, 37 degrees C., 5% CO2 @ 0.1 L/min until viability dropped to 30%. The conditioned medium was collected by sterile filtration. Antibody was recovered by affinity chromatography using recombinant Protein A followed by dialysis into PBS.

Examples 5-7: Comparative Data Between Hybridomas and/or Chimeric mAbs and/or Humanised Mabs Example 5: Comparison of SAP-K and SAP-E Hybridomas in Human SAP Binding ELISA 1 µg/mL or 5 µg/mL human SAP was directly immobilised onto an ELISA plate and blocked with 1% BSA/TBS plus 0.05% TWEEN20. Anti-SAP antibodies from purified material were titrated across the plate. Bound antibody was detected by treatment with a horse-radish peroxidase (HRP)-conjugated rabbit-anti-mouse IgG antibody (Dako, P0260). The ELISA was developed using O-phenylenediamine dihydrochloride (OPD) peroxidase substrate (Sigma, P9187).

FIG. 1 shows the binding curves for murine antibodies SAP-E and SAP-K at a 1 µg/mL coating concentration of human SAP.

Figure 2:
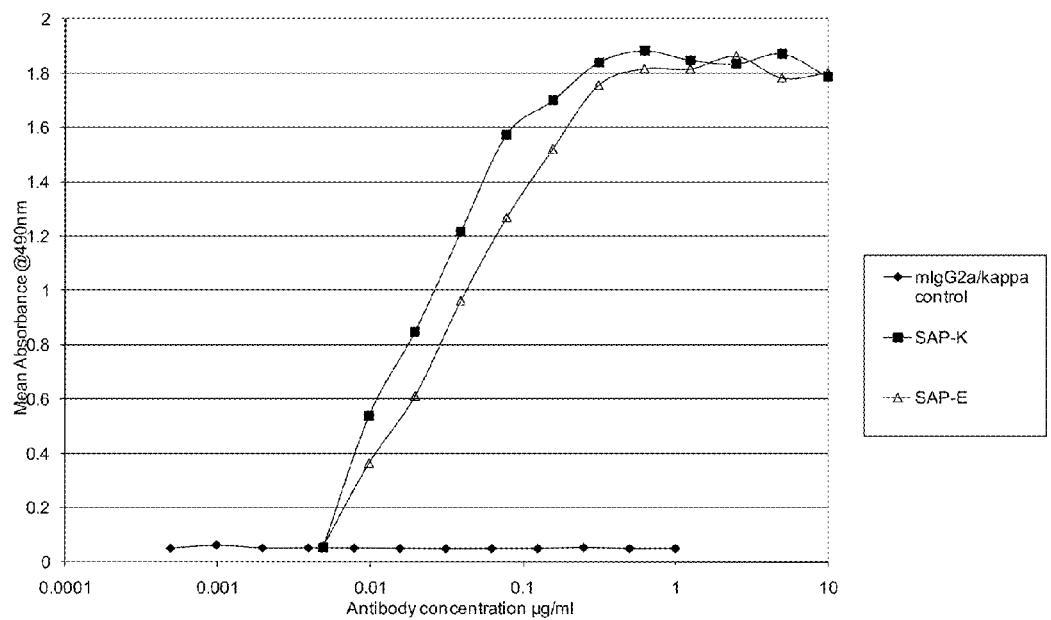
FIG. 2 shows the binding curves for murine antibodies SAP-E and SAP-K at a 5 µg/mL coating concentration of human SAP.

FIG. 2 shows the binding curves for murine antibodies SAP-E and SAP-K at a 5 µg/mL coating concentration of human SAP.

At the 5 µg/mL coating concentration, SAP-K and SAP-E showed similar binding to the immobilised human SAP, whereas at the 1 µg/mL lower density coating SAP-K showed greater binding than the SAP-E. All subsequent human SAP binding ELISAs using this format used the lower density 1 µg/mL coating concentration to distinguish between the binding properties of the two antibodies.

Example 6: Comparison of SAP-K and SAP-E Chimeric/Humanised mAbs in Human SAP Binding ELISA 1 µg/mL human SAP was directly immobilised onto an ELISA plate and blocked with 1% BSA/TBS plus 0.05% TWEEN20. Anti-SAP antibodies from the test supernatants or purified material were titrated across the plate. Bound antibody was detected by treatment with goat anti-human Kappa Light Chains peroxidase conjugate (Sigma, A7164). The ELISA was developed using O-phenylenediamine dihydrochloride (OPD) peroxidase substrate (Sigma, P9187).

Figure 3:
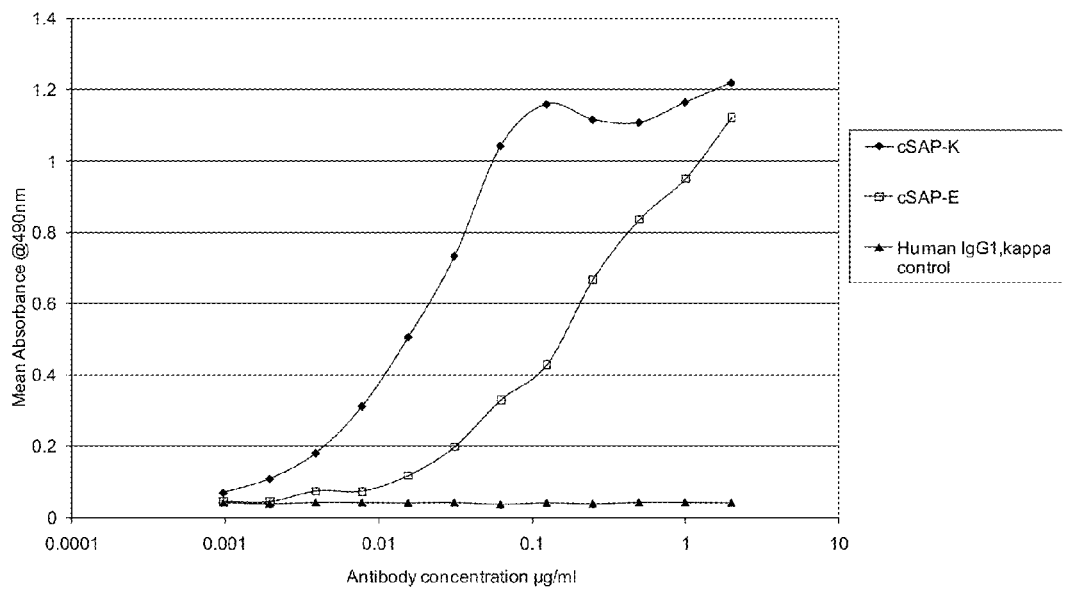
FIG. 3 shows the binding curves for chimeric antibodies cSAP-E and cSAP-K. The profile of the curves for the chimeric antibodies is the same as that of the equivalent hybridomas.

FIG. 3 shows the binding curves for chimeric antibodies cSAP-E and cSAP-K. The profile of the curves for the chimeric antibodies is the same as that of the equivalent hybridomas.

Figure 4:
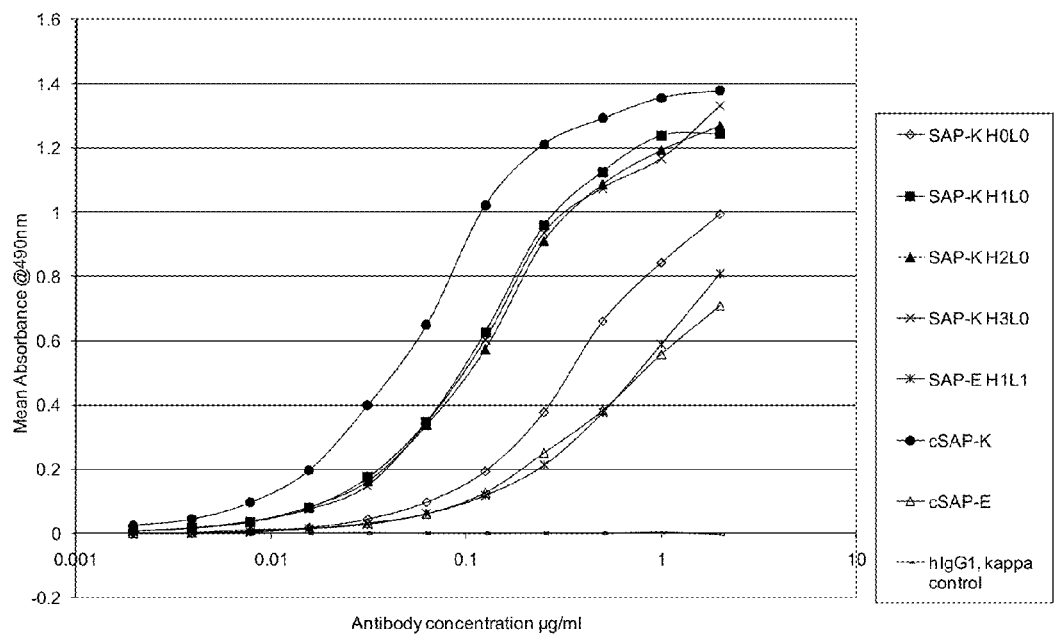
FIG. 4 shows the binding curves for SAP-K H0L0, SAP-K H1L0, SAP-K H2L0 and SAP-K H3L0 compared to the SAP-K chimera and the SAP-E H1L1 compared to the SAP-E chimera. An irrelevant human IgG1 kappa antibody was also tested as a negative control.
Figure 5:
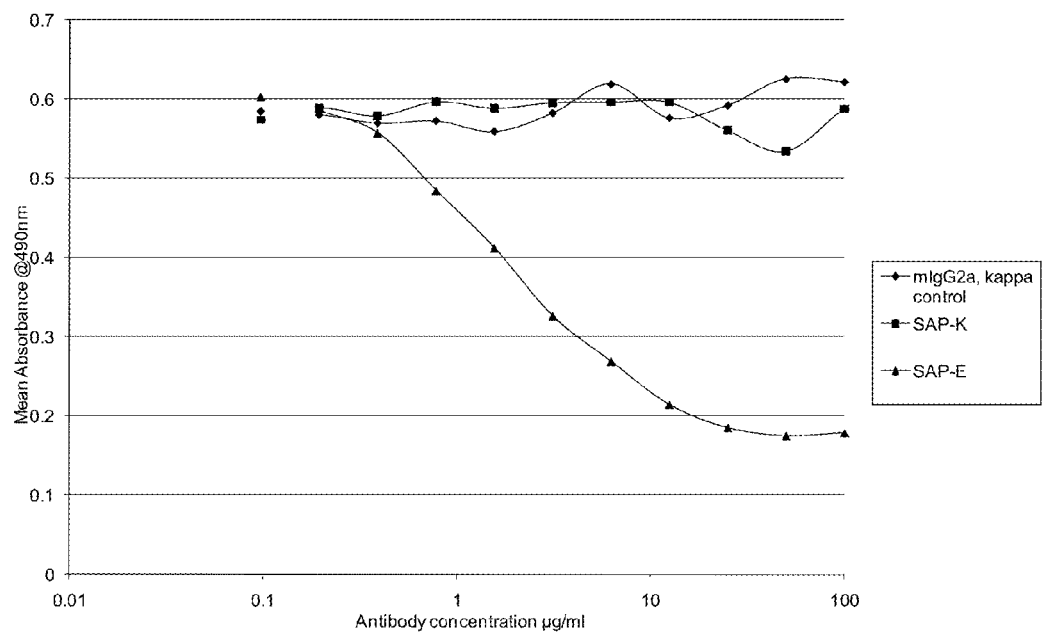
FIG. 5 shows purified SAP-K and SAP-E murine monoclonal antibodies in a competition ELISA with the SAP-E chimera.
Figure 6:
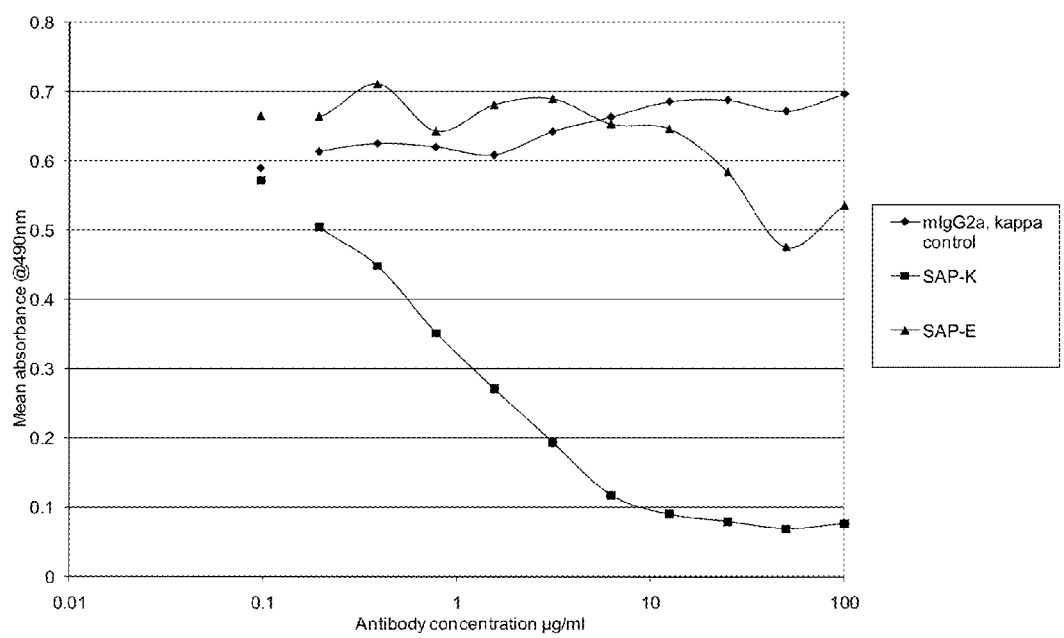
FIG. 6 shows purified SAP-K and SAP-E murine monoclonal antibodies in a competition ELISA with the SAP-K chimera.

FIG. 4 shows the binding curves for SAP-K H0L0, SAP-K H1L0, SAP-K H2L0 and SAP-K H3L0 compared to the SAP-K chimera and the SAP-E H1L1 compared to the SAP-E chimera. An irrelevant human IgG1 kappa antibody was also tested as a negative control. The data shows that humanisation of the SAP-K antibody resulted in a loss of human SAP binding activity of approximately 2-fold compared to the parental SAP-K chimera, whilst the humanised SAP-E antibody retained binding activity compared to the parental SAP-E chimera.

Example 7—Competition ELISA

ELISA plates were coated with human SAP at either 1 μg/mL (for competition with SAP-K chimera) or 5 μg/mL (for competition with SAP-E chimera) and blocked with 1% BSA/PBS. A constant concentration of chimeric anti-SAP mAb was mixed with serial diluted (1:1) amounts of mouse anti-SAP mAbs. Plates were washed and the amount of chimeric antibody bound to the immobilised human SAP was detected using goat anti-human Kappa Light chain peroxidase conjugate (Sigma, A7164). The ELISA was developed using O-phenylenediamine dihydrochloride (OPD) peroxidase substrate (Sigma, P9187).

FIG. 5 shows purified SAP-K and SAP-E murine monoclonal antibodies in the competition ELISA with the SAP-E chimera.

FIG. 6 shows purified SAP-K and SAP-E murine monoclonal antibodies in the competition ELISA with the SAP-K chimera.

In both FIGS. 5 and 6 no competition is observed between the SAP-E and SAP-K antibodies showing that the two antibodies bind to distinct epitopes on the human SAP molecule.

Example 8: Determination of Kinetics of Binding

Biacore Analysis of Binding of Humanised Anti-SAP Antibody Variants to Purified Human and Purified Cynomologus Monkey SAP.

Human and cynomologus monkey SAP were immobilised on a Biacore C1 chip by primary amine coupling in accordance with the manufacturer's instructions. Humanised anti-SAP antibody contained in culture supernatants and purified chimeric antibodies at 512 nM were passed over both human and cynomologus monkey SAP surfaces and binding sensograms obtained. All runs were double referenced with a buffer injection for purified sample or media for the supernatant samples over the human and cyno SAP surfaces. Analysis was carried out at 25° C. using HBS-EP buffer. Regeneration of surface was done in the presence of 3M MgCl2 and did not affect the ability of antibodies to rebind to human SAP in a subsequent cycle. Data were analysed using the 1 to 1 dissociation model within the Biacore T100 evaluation software.

The data generated in Tables 6a and 6b show off-rates (kd) of the humanised SAP-E and SAP-K antibody supernatants respectively. The values were based on a single curve and used for ranking purposes between the different constructs for binding to human SAP. Humanised SAP-E antibodies showed better off-rates than the humanised SAP-K antibodies for binding human SAP. A number of the SAP-K humanised antibody variants showed binding to cynomologus monkey SAP (N.B. the SAP-K chimera bound cynomologus monkey SAP) whilst none of the humanised SAP-E antibody variants bound cynomologus monkey SAP (N.B. the SAP-E chimera likewise did not bind cynomologous monkey SAP). Humanised SAP-E variants which contained either the straight graft humanised heavy chain (H0) or the straight graft humanised light chain (L0) or a combination of both showed the poorest off-rates. The SAP-E humanised L1 light chain was the best light chain variant and combination of the L1 with the H1 heavy chain variant gave a humanised antibody with an acceptable off-rate whilst keeping the number of back mutations to a minimum. Off-rate ranking of the humanised SAP-K variants showed the L0 straight graft to be the best humanised light chain variant and the H0 straight graft to be the poorest humanised heavy chain variant.

TABLE 6a

| SAP-E Variant | Kd for human SAP ($s^{-1}$) |
|---|---|
| SAP-E chimera | 3.83E−03 |
| SAP-E H1L1 | 4.80E−03 |
| SAP-E H4L1 | 5.43E−03 |
| SAP-E H1L2 | 5.51E−03 |
| SAP-E H3L1 | 5.76E−03 |
| SAP-E H4L2 | 5.80E−03 |
| SAP-E H2L1 | 6.09E−03 |
| SAP-E H3L2 | 6.31E−03 |
| SAP-E H2L2 | 6.52E−03 |
| SAP-E H1L0 | 8.09E−03 |
| SAP-E H3L0 | 9.10E−03 |
| SAP-E H2L0 | 9.79E−03 |
| SAP-E H4L0 | 9.81E−03 |
| SAP-E H0L1 | 4.02E−02 |
| SAP-E H0L2 | 4.29E−02 |
| SAP-E H0L0 | 5.35E−02 |

TABLE 6b

| N.B. Kd is for human SAP | | |
|---|---|---|
| | kd ($s^{-1}$) | Binding to cyno SAP |
| SAP-K chimera | 6.64E−03 | Yes |
| SAP-K H1L0 | 1.71E−02 | poor |
| SAP-K H3L0 | 1.84E−02 | Yes |
| SAP-K H2L0 | 2.04E−02 | Yes |
| SAP-K H3L1 | 2.36E−02 | yes |
| SAP-K H0L0 | 2.63E−02 | no |
| SAP-K H1L1 | 2.96E−02 | poor |
| SAP-K H2L1 | 3.21E−02 | poor |
| SAP-K H0L1 | 4.79E−02 | no |

Biacore Analysis of Binding of Anti-SAP Antibodies to Purified Human SAP Directly Immobilised on a Solid Phase Support Human SAP was immobilised on a Biacore CM3 chip by primary amine coupling in accordance with the manufacturer's instructions. Anti SAP antibodies were passed over this surface at 512, 128, 32, 8, 2, 0.5 nM and binding sensorgrams obtained. All runs were double referenced with a buffer injection over the human SAP surface. Analysis was carried out at 25° C. using HBS-EP buffer. Regeneration of surface was done by allowing buffer to flow over the surface for several minutes and did not affect the ability of human SAP to rebind antibodies in a subsequent cycle. Data were analysed from the 128-0.5 nM runs using the bivalent analyte model inherent to the Biacore T100 evaluation software.

The data generated and compiled in table 7 were meant for comparison between the constructs and show that SAP-K antibodies have a better association rate in this assay while SAP-E antibodies show better dissociation rates. Furthermore, humanization had not altered the binding kinetics of SAP-E antibody whilst for SAP-K a loss in association and dissociation rate was observed following humanisation.

TABLE 7

|  | Ka (M−1 · s$^{-1}$) | Kd (s$^{-1}$) | KD (nM) |
| --- | --- | --- | --- |
| SAP-K chimera | 4.06E+5 | 7.59E−03 | 18.7 |
| SAP-K H0L0 | 6.08E+4 | 4.49E−02 | 739 |
| SAP-K H1L0 | 1.15E+5 | 1.78E−02 | 155 |
| SAP-K H2L0 | 1.15E+5 | 2.20E−02 | 191 |
| SAP-K H3L0 | 1.50E+5 | 1.92E−02 | 128 |
| SAP-E chimera | 2.64E+4 | 2.18E−03 | 82.6 |
| SAP-E H1L1 | 2.64E+4 | 2.07E−03 | 78.3 |

Biacore Analysis of Binding of Anti-SAP Antibodies to Purified Human SAP Captured on Immobilised O-Phosphoethanolamine O-phosphoethanolamine was immobilised on a Biacore CM5 chip by primary amine coupling in accordance with the manufacturer's instructions. Human SAP was then captured on the surface in the presence of calcium chloride, in order to replicate in the Biacore system in vitro, the precise orientation of SAP molecules bound to amyloid fibrils in vivo. Anti SAP antibodies were then passed over this surface at 256, 64, 16, 4, 1 nM and a binding sensorgrams obtained. Analysis was carried out at 25° C. using 4% BSA, 10 mM Tris, 140 mM NaCl, 2 mM CaCl$_2$, 0.05% surfactant P20, 0.02% NaN$_3$, pH 8.0 as running buffer. Regeneration was achieved using two pulses of Tris-EDTA (10 mM Tris, 140 mM NaCl, 10 mM EDTA, pH 8.0) which removed the bound human SAP but did not significantly affect subsequent binding of SAP to the immobilised phosphoethanolamine. Data generated were double referenced with a buffer injection over the human SAP surface and analyzed using the bivalent analyte model in the Biacore T100 evaluation software.

The data generated, as shown in Table 8, are intended only for comparison between the constructs. They do not constitute accurate kinetic values, due to possible modification of binding by the avidity effect inherent in the assay format. Avidity is more likely to have affected antibody dissociation rates, leading to lower calculated KD values. Furthermore, for all the SAP-E antibodies, the dissociation rate (kd) obtained is outside the limit of the Biacore measurement range. Nevertheless, the results indicate tight binding of the anti-SAP antibodies to human SAP immobilised by interaction of the SAP with a solid phase ligand, just as it is in amyloid deposits in vivo, which is the therapeutic target of the present invention.

TABLE 8

|  | ka (M$^{-1}$ · s$^{-1}$) | kd (s$^{-1}$) | KD (nM) |
| --- | --- | --- | --- |
| SAP-K chimera | 3.32E+5 | 2.97E−4 | 0.895 |
| SAP-E chimera | 2.03E+4 | 9.12E−7 | 4.49E−11 |
| Mouse SAP-K | 3.00E+5 | 2.19E−4 | 0.730 |
| Mouse SAP-E | 3.15E+4 | 1.51E−8 | 4.79E−13 |
| SAP-K H3L0 | 1.36E+5 | 5.01E−3 | 36.8 |
| SAP-E H1L1 | 1.94E+4 | 1.58E−7 | 8.14E−12 |

Example 9: Amino Acid Scan at Position 91 of SAP-K L0 Humanised Light Chain

Site-directed saturation mutagenesis was used to generate a panel of variants where the cysteine residue at position 91 (Kabat numbering) was potentially substituted with all other 19 amino acids in a single reaction by using a mutagenesis primer encoding NNK at this position (where N codes for adenosine or cytidine or guanosine or thymidine and K codes for guanisine or thymidine). From Biacore off-rate ranking carried out on antibody supernatant for the variants generated, four were selected for scale up in the HEK2936E cells and purification. Biacore kinetic analysis using the O-phosphoethanolamine method as detailed in Example 7 showed that the variant with alanine at position 91 (SEQ ID NO:43) had an improved affinity compared to the wild-type; KD values of 0.436 nM and 36.8 nM were measured respectively. N.B. all variants were tested in the same experiment used to produce the results shown in table 7.

Other variants, for example glycine, serine and valine improved binding with respect to H3L0, but to a lesser extent than alanine. In addition, the fact that these four variants had better binding properties than L0 was also observed in a binding ELISA and a Biacore off-rate ranking experiment when the light chains were paired with H1.

SAP-K humanised light chain V region variant L0
91A nucleotide sequence (codon optimised)
(SEQ ID NO: 73)
GACATCCAGATGACCCAGAGCCCCTCTTCACTGAGCGCTAGCGTGGGC

GACAGGGTGACCATCACCTGCAAGGCCAGCCAGAACGTGAACAGCAAC

GTGGCCTGGTACCAGCAGAAGCCCGGCAAAGCCCCCAAGCTCCTGATC

TACAGCGCCAGCTACAGATATAGCGGCGTGCCTAGCAGGTTTAGCGGC

AGCGGAAGCGGGACCGATTTCACCCTGACCATCAGCAGCCTGCAGCCC

GAGGACTTCGCCACTTACTACTGCCAGCAGGCGAACAACTACCCCTTC

ACCTTCGGCCAGGGCACCAAGCTGGAGATCAAG

SAP-K humanised light chain V region variant L0
91A amino acid sequence
(SEQ ID NO: 74)
DIQMTQSPSSLSASVGDRVTITCKASQNVNSNVAWYQQKPGKAPKLLI

YSASYRYSGVPSRFSGSGSGTDFTLTISSLQPEDFATYYCQQANNYPF

TFGQGTKLEIK

Example 10: Complement Dependence of Amyloid Clearance by Anti-SAP Antibody

The role of complement in amyloid clearance by anti-SAP antibody was investigated by comparing the efficiency of the treatment between mice with complement deficiency and normal, complement sufficient, animals. Targeted deletion of the gene for C1q blocks activation of the classical complement pathway, which is initiated by binding of C1q to antibody-antigen complexes, but C$_3$ activation, the pivotal functional step responsible for chemotaxis and opsonisation, the major biological functions of complement, can still proceed via the alternative and lectin pathways as well as by direct C3 cleavage by non-complement serine proteinases. Targeted deletion of the gene for C3 completely abrogates these functions.

Induction of AA Amyloidosis

AA amyloidosis was induced and confirmed in two groups of complement deficient mice: C3 knockouts (n=14) and C1q knockouts (n=12), and in 15 wild-type mice. All mice were pure line C57BL/6. Each mouse received a single dose of amyloid enhancing factor, an extract of amyloidotic tissue containing amyloid fibrils (Baltz et al, (1986) Plenum Press, New York, pp. 1 15-121), by intravenous injection followed 4 days later by 10 daily subcutaneous injections of 10% w/v casein in solution in 0.1M NaHCO$_3$ administered over a 12 day period (Botto et al, (1997) *Nature Med.*, 3: 855-859). Casein elicits persistent acute inflammation and a sustained increase in serum amyloid A protein (SAA) production leading to AA amyloid deposition in all animals. Seven days after the last casein injection, KI was introduced into the drinking water of all mice and 3 days later each mouse received an intravenous injection of a standard dose of $^{125}$I-labelled human SAP (Hawkins et al, (1990) *J. Clin. Invest.*, 86: 1862-1 869 and Hawkins et al, (1988) *J. Exp. Med.*, 167: 903-913). All mice underwent whole body counting 24 h and 48 h after the tracer injection to determine retention of radioactivity, a precise index of whole body amyloid load. Ten days after the $^{125}$I-SAP tracer injection, all mice were 'loaded' with human SAP by a single intraperitoneal injection of 10 mg per mouse of isolated pure human SAP. Human SAP injected into amyloidotic mice localises in the amyloid deposits and persists there with a half life of about 3-4 days whilst any human SAP not bound to amyloid is cleared from the circulation with a half life of about 3-4 hours (Hawkins et al, (1988) *J. Exp. Med.*, 167: 903-913 and Pepys et al, (2002) *Nature*, 41 7: 254-259).

Immunohistochemical staining with anti-human SAP antibody in spleen of an amyloidotic mouse after injection of isolated pure human SAP shows that there is strong positive staining of all the amyloid deposits in their typical marginal zone distribution. This bound human SAP is the target of the therapeutic anti-SAP antibody according to the present invention.

Anti-SAP Treatment

Three days after the human SAP injection, when human SAP was no longer detectable in the circulation, all mice except two in each of the complement knockout groups received a single intraperitoneal injection of 1 ml of the whole IgG fraction (batch no. 2866) of monospecific sheep anti-human SAP antiserum at 50 mg/ml in solution in phosphate buffered saline (PBS), containing 7 mg/ml of actual anti-SAP antibody. The antiserum was produced by The Binding Site Ltd, Birmingham, UK, using human SAP (rigorously purified to 100% in the University College London Centre for Amyloidosis and Acute Phase Proteins) and proprietary immunisation procedures. All animals were then killed 15 days after anti-SAP administration for histological estimation of amyloid load by alkaline alcoholic Congo red staining (Puchtler, H., Sweat, F. and Levine, M. (1962) On the binding of Congo red by amyloid. *J. Histochem. Cytochem.*, 10: 355-364). Congo red sections of spleen and liver of all animals were independently examined by one or more expert observers, blinded to the treatment each mouse had received, and scored for the amount of amyloid present as previously reported (Botto et al, (1997) *Nature Med.*, 3: 855-859). The scores of 1-5 represent an approximately log base 10 ranking scale from 1, corresponding to one or two tiny specks of amyloid among several sections of a particular organ, to 5, corresponding to abundant widespread deposits comprising about 10,000 times more amyloid than grade 1 (Botto et al, (1997) *Nature Med.*, 3: 855-859). The scores of the different observers were always highly concordant although some observers also used intermediate integer. 5 scores. The arithmetic mean of the scores of all observers for each organ in each animal were used for statistical analysis.

Results

In marked contrast to the effective clearance of amyloid deposits in the complement sufficient wild-type mice, there was still abundant amyloid present in both groups of complement deficient animals although it tended to have a more fragmented appearance than in the two control complement deficient mice of each type. The median, range, spleen amyloid scores were: wild type, 1.17, 0.0-1.5, n=15; C3 knockout, 1.92, 1.17-4.33, n=12; C1q knockout, 1.25, 1.17-3.5, n=10 (Kruskal-Wallis non-parametric ANOVA, P<0.001). The differences between the wild type controls and both complement deficient groups were significant, P<0.001 for the C3 knockouts and P=0.036 (with Bonferroni correction for multiple comparisons) for the C1q knockouts, but the difference between the C3 and C1q knockouts was not significant, P=0.314 (Mann-Whitney U tests).

Discussion

In mice lacking either C1q or C3, anti-SAP treatment did not clear amyloid deposits as effectively as in complement sufficient wild-type mice. The therapeutic efficacy of anti-SAP is thus very substantially complement dependent and is not mediated by IgG antibody binding alone which could, in theory, engage phagocytic cells via their Fc(γ) receptors. Nevertheless the more fragmented appearance of the persistent amyloid deposits in the complement deficient mice suggested at least some effect of antibody alone. Also the trend to more clearance in C1q deficient compared to C3 deficient animals suggested that C3 activation is critical and that some complement activation may be taking place in the absence of C1q.

Example 11: Requirement for Intact IgG Anti-SAP Antibody

Complement activation by IgG antibody requires the whole intact molecule, including the Fc region, and proceeds via the classical pathway initiated by binding of C1q. However, in some antibody-antigen systems, complement activation via the alternative pathway can be mediated by the F(ab)$_2$ fragment. In order to confirm the complement dependence of amyloid clearing by anti-SAP antibody and to investigate the potential requirement for the Fc region of the antibody, the effect was tested of F(ab)$_2$ anti-SAP antibody which was produced by pepsin cleavage at pH 4.0 of the IgG fraction of the sheep polyclonal anti-human SAP antiserum (batch 2866) and purified by standard methods.

Induction and Treatment of AA Amyloidosis

AA amyloidosis was induced and confirmed in wild-type C57BL/6 mice as detailed in Example 10 above. After loading the amyloid deposits with human SAP also as detailed in Example 10, groups of mice were treated with whole IgG fraction of the sheep polyclonal anti-human SAP antiserum, with buffer vehicle alone or with the F(ab)$_2$ fragment of the IgG fraction. The dose of anti-SAP antibody activity injected was 7.28 mg per mouse receiving F(ab)$_2$ and 7 mg (50 mg of total IgG as usual) per mouse receiving whole IgG. All mice were killed 14 days later for estimation of amyloid load by Congo red staining.

Results

Clearance of amyloid deposits was almost complete in mice receiving IgG anti-SAP antibody compared to the massive amyloid deposits in the control mice receiving vehicle alone. The mice receiving F(ab)$_2$ had less amyloid than untreated controls, but still substantially more than the mice treated with whole IgG anti-SAP antibody (Table 9).

TABLE 9

Reduced efficacy of F(ab)$_2$ anti-SAP compared to intact IgG antibody in clearing amyloid deposits.

| Group | Amyloid score median, range | |
|---|---|---|
| (treatment, group size) | Spleen | Liver |
| 1 (no antibody, n = 10) | 4.0, 4.0-4.33 | 3.5, 2.67-4.67 |
| 2 (IgG anti-SAP antibody, n = 8) | 1.0, 1.0-3.67* | 1.25, 1.0-1.5 |
| 3 (F(ab)$_2$ anti-SAP antibody, n = 5) | 2.17, 1.33-3.0 | 1.67, 1.33-1.67 |

Kruskal-Wallis test: spleen, P < 0.001; liver P < 0.001
Mann-Whitney tests**: 1 vs 2, spleen & liver both, P < 0.001; 1 vs 3, spleen & liver both, P = 0.001; 2 vs 3, spleen, P = 0.284; liver, P = 0.019
*Single outlier in group 2 with heavy spleen amyloid despite IgG anti-SAP treatment. Excluding this animal gives a highly significant difference between efficacy of IgG and F(ab)$_2$ anti-SAP antibody treatment.
**Due to the multiple comparisons, a P value of 0.01 or less is required for significance Discussion The molar dose of F(ab)$_2$ anti-SAP antibody used in this study was about one third greater than that of IgG antibody, due to the smaller molecular weight of the F(ab)$_2$ fragment compared to whole IgG. For optimal effect on amyloid clearance the Fc is required. This is not because of direct involvement of cellular recognition by Fc(γ) receptors since the whole IgG was even less effective in complement deficient mice than was F(ab)$_2$ in complement sufficient mice. It is likely that the high dose of F(ab)$_2$ that was administered was able to activate some complement via the alternative pathway.

Example 12: Requirement for Macrophages

The histological and histochemical studies described in US 2009/0191196 show that the cells which infiltrate, surround and phagocytose the amyloid deposits in mice treated with anti-SAP antibody are macrophages. In order to confirm that macrophages are indeed responsible for the clearance of the amyloid, the effect of treatment with the whole IgG fraction of the sheep polyclonal anti-human SAP antiserum (batch 2866) was tested in mice in which all macrophage activity had been inhibited by administration of liposomal clodronate. The reagents, experimental protocol and effects on macrophage function of liposomal clodronate are well established and extensively documented (Van Rooijen et al, (2002) *J. Liposome Research. Vol.* 12. Pp, 81-94).
Induction and Treatment of AA Amyloidosis After induction and confirmation of AA amyloidosis in wild-type mice, using the protocol detailed in Example 10 above, all animals received a single intraperitoneal dose of 10 mg of isolated pure human SAP to load their deposits with human SAP. The test group then received 0.3 ml of liposomal clodronate intraperitoneally immediately and on days 2, 7 and 14 thereafter. One control group and the test group received a single intraperitoneal dose of 50 mg of the IgG fraction of sheep anti-human SAP antiserum on day 3 after the human SAP injection. A second control group received no anti-SAP and no other additional treatment. All mice were killed for estimation of amyloid load by Congo red staining 14 days after administration of the anti-SAP to the test and antibody control groups.
Results Treatment with anti-SAP produced almost complete clearance of amyloid deposits compared to the group which received no antibody. In contrast, in mice which received the liposomal clodronate in a regime known to completely ablate macrophage function, there was no clearance of amyloid deposits (Table 10).

TABLE 10

Macrophage depletion inhibits clearance of amyloid deposits by anti-SAP antibody.

| Group | Amyloid score median, range | |
|---|---|---|
| (treatment, group size) | Spleen | Liver |
| 1 (clodronate plus anti-SAP, n = 13) | 4.83, 2.0-5.0 | 3.17, 2.0-3.5 |
| 2 (anti-SAP only, n = 12) | 1.33, 0.67-3.5 | 1.0, 0.67-2.5 |
| 3 (none, n = 12) | 4.0, 3.5-4.5 | 2.83, 1.0-3.17 |

Kruskal-Wallis test: spleen, P < 0.001; liver P < 0.001
Mann-Whitney tests with Bonferroni correction: 1 vs 2: spleen & liver both, P < 0.003; 1 vs 3: spleen, P = 0.078; liver, P = 0.411; 2 vs 3, spleen & liver both, P < 0.003.

Discussion

The result in this particular experiment confirmed that macrophage function is required for clearance of amyloid deposits by anti-human SAP antibody.

Example 13: Efficacy of Mouse Monoclonal Anti-Human SAP Antibody, SAP-E, in Clearing Mouse Systemic AA Amyloid Deposits The capacity of various monoclonal antibodies to mediate clearance of murine AA amyloid deposits containing human SAP was sought in comparison with the standard sheep polyclonal anti-human SAP antibody as a positive control.
Induction of AA Amyloidosis and Treatment SAP knockout C57BL/6 mice transgenic for human SAP were created by crossing pure line C57BL/6 animals in which the mouse SAP gene has been deleted (Botto et al, (1997) *Nature Med.,* 3: 855-859) with C57BL/6 mice bearing a human SAP transgene (Yamamura et al, (1993) *Mol. Reprod. Dev.,* 36: 248-250 and Gillmore et al, (2004) *Immunology,* 112: 255-264). These mice thus lack mouse SAP but express human SAP at concentrations significantly greater than those seen in man. Systemic AA amyloidosis was induced in the human SAP transgenic mouse SAP knockout mice as described in Example 10, and 9 days after the final injection of casein into the mice, the presence and extent of amyloid deposition were confirmed as usual by whole body counting of amyloid after injection of a tracer dose of $^{125}$I-labelled human SAP. All mice had substantial and comparable amounts of amyloid, and were allocated into closely matched groups to receive the different treatments. One week after the tracer injection, each mouse received a single dose of 5 mg CPHPC by intraperitoneal injection, to deplete their circulating human SAP, followed 5 h later via the same route by either the standard sheep polyclonal anti-human SAP IgG fraction (batch 2866, 1 ml at 50 mg/ml total protein containing 7 mg/ml anti-human SAP antibody) or 5 mg of one of nine different isolated pure monoclonal anti-human SAP antibodies (Table 11). All mice were killed 21 days after the antibody injection and amyloid load was determined by Congo red histology of their spleens.

TABLE 11

The presence of amyloid in spleen of mice with systemic AA amyloidosis after treatment with CPHPC and various anti-human SAP antibodies.

| Antibody treatment | Antibody isotype | Amyloid score median, range |
|---|---|---|
| none | | 3, 3-5 |
| polyclonal | NA | 1, 1-1 |
| monoclonal SAP-A | IgG1 | 3, 2-4 |

TABLE 11-continued

The presence of amyloid in spleen of mice with systemic AA amyloidosis after treatment with CPHPC and various anti-human SAP antibodies.

| Antibody treatment | Antibody isotype | Amyloid score median, range |
|---|---|---|
| monoclonal SAP-B | IgG2a | 3, 2-4 |
| monoclonal SAP-C | IgG1 | 4, 2-4 |
| monoclonal SAP-D (n = 1) | IgG1 | 4 |
| monoclonal SAP-E | IgG2a | 1, 1-1 |
| monoclonal SAP-F (n = 1) | IgG1 | 2 |
| monoclonal SAP-G | IgG1 | 3, 2-4 |

Among the monoclonal antibodies tested, only SAP-E produced clearance of the amyloid deposits but its effect was the same as the highly reproducible and dramatic action of the sheep polyclonal antibody. Importantly SAP-E is of the mouse IgG2a isotype which is known to activate mouse complement while all the other monoclonals except SAP-B were mouse IgG1 isotype which is not complement activating. Although SAP-B is a mouse IgG2a isotype, its binding to SAP in vitro was notably less than that of SAP-E and evidently was not sufficient in vivo to be effective.

Discussion

These results demonstrate that a sufficiently avid, complement activating, IgG2a mouse monoclonal anti-human SAP antibody mediates amyloid clearance in vivo as effectively as sheep polyclonal anti-human SAP antibody.

Example 14: Comparative Characterisation of Monoclonal Mouse Anti-Human SAP Antibodies, SAP-K and SAP-E, In Vitro SAP-K was selected from among the 6 different, most avidly binding, mouse IgG2a monoclonals, derived by standard techniques from immunization with purified human SAP and a conventional fusion to produce hybridomas which were cloned by routine methods. Among these IgG2a antibodies, SAP-K showed the greatest binding to immobilised human SAP. This was the case regardless of whether the human SAP had been directly immobilised on plastic surfaces by non-specific adherence or by covalent attachment, or by the specific calcium dependent binding of SAP to immobilised ligands, whether amyloid fibrils or the small molecule ligand, phosphoethanolamine. SAP-K also bound well to directly immobilised SAP in the presence or absence of calcium, and if the SAP had previously been complexed with CPHPC and then covalently 'fixed' in the decameric SAP-CPHPC complex (Pepys, M. B. et al (2002) Targeted pharmacological depletion of serum amyloid P component for treatment of human amyloidosis. *Nature,* 417: 254-259; Kolstoe, S. E. et al (2009) Molecular dissection of Alzheimer's disease neuropathology by depletion of serum amyloid P component. *Proc. Natl. Acad. Sci. USA,* 106: 7619-7623). SAP-E also bound well to human SAP in all these different configurations. However the two antibodies differ significantly in that much more SAP-K than SAP-E became bound when human SAP was only sparsely available, for example when plates were exposed to just 1 µg/ml of human SAP for coating, whereas when there was more abundant immobilised SAP, for example when the coating solution contained 100 µg/ml of SAP, then there was more binding of SAP-E than SAP-K. This difference suggest that SAP-E binds optimally when more than one SAP molecule lies closely associated with another whilst SAP-K binds avidly to single isolated SAP molecules. This mechanism is supported by the finding that when human SAP was immobilised by capture on plates coated with polyclonal sheep anti-human SAP (batch 2866), which provides pairs of SAP molecules held closely together in the two arms of each sheep IgG antibody molecule, SAP-E bound better than SAP-K at all levels of human SAP input (FIG. 7).

Figure 7:
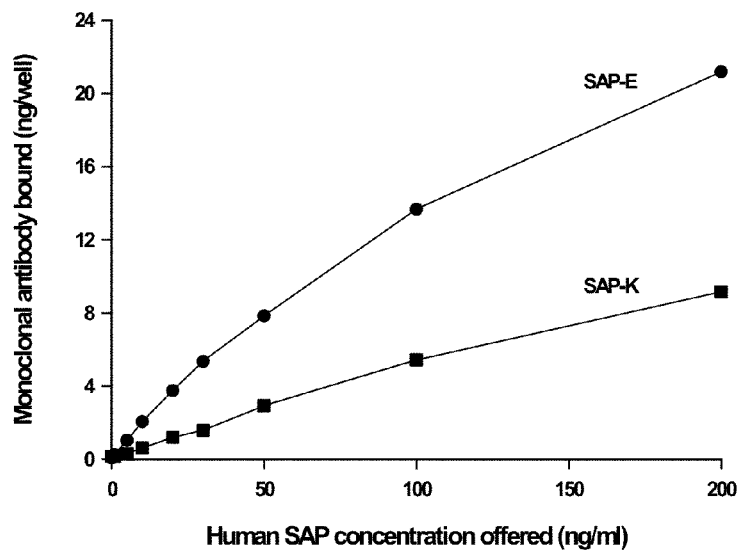
FIG. 7 shows an immunoradiometric assay for binding of monoclonal mouse antibodies SAP-E and SAP-K to human SAP captured by immobilised sheep polyclonal anti-human SAP antibody.

FIG. 7 shows immunoradiometric assay for binding of monoclonal mouse antibodies to human SAP captured by immobilised sheep polyclonal anti-human SAP antibody. Substantially more SAP-E than SAP-K bound at all concentrations of human SAP offered. Each point is the mean of 3 replicates.

Very importantly, both SAP-E and SAP-K bound apparently equally well to native human SAP, shown by the similar immunoprecipitation of both antibodies in double immunodiffusion in agarose gel against both isolated pure human SAP and whole human serum. The similar binding of these two mouse monoclonal antibodies was reflected in the similar parameters measured in the Biacore instrument (BIAcoreX, Pharmacia Biosensor AB, Uppsala, Sweden) using human SAP covalently immobilised on the chip (Table 12).

TABLE 12

Affinity of monoclonal antibodies for human SAP determined by Biacore

| | $k_a$ (M$^{-1}$ sec$^{-1}$) | $k_d$ (sec$^{-1}$) | $K_D$ (M) |
|---|---|---|---|
| SAP-E | $2 \pm 5 \times 10^4$ | $6 \pm 4 \times 10^{-5}$ | $5 \pm 4 \times 10^{-9}$ |
| SAP-K | $3.18 \pm 5 \times 10^4$ | $1.7 \pm 0.9 \times 10^{-5}$ | $1 \pm 1.7 \times 10^{-9}$ |

Values shown are mean and SD of 3 replicate measurements

In contrast, although both antibodies bound to native human SAP in western blotting after agarose gel electrophoresis in physiological buffers, only SAP-E bound to human SAP in western blotting from reduced SDS-PAGE. SAP-E thus recognises denatured human SAP while SAP-K only recognises native human SAP and must be binding to a conformational epitope.

Figure 8:
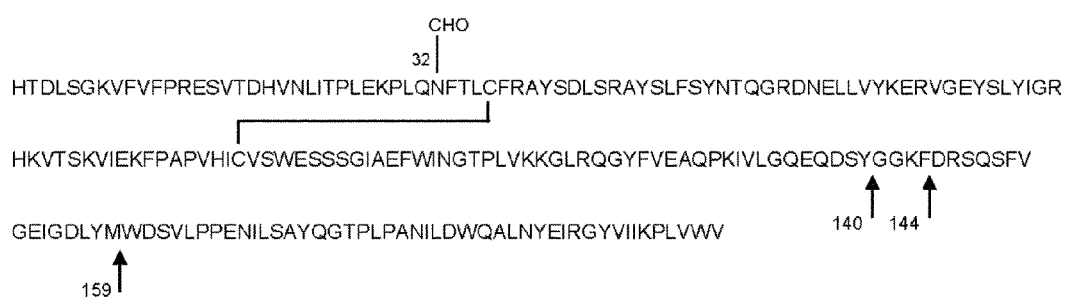
FIG. 8 shows epitope mapping for monoclonal anti-human SAP antibody SAP-E.
Figure 8:
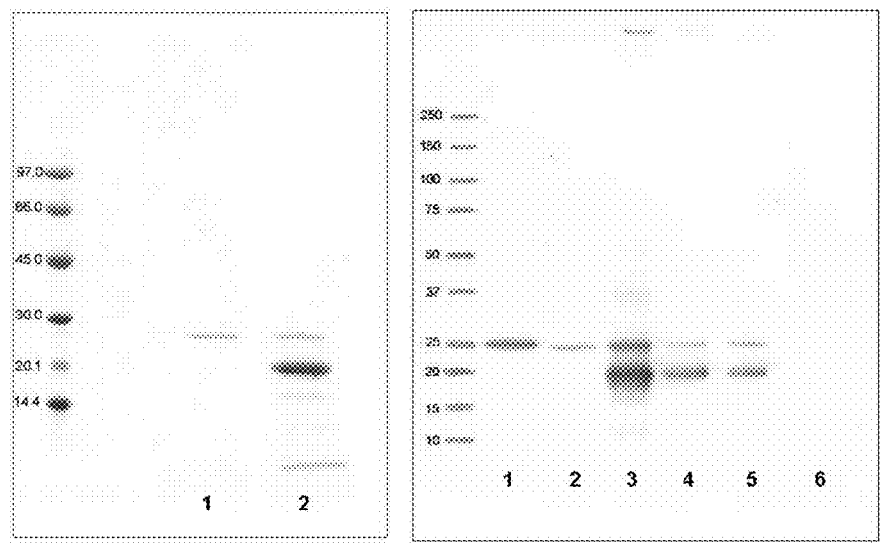
Figure 8:
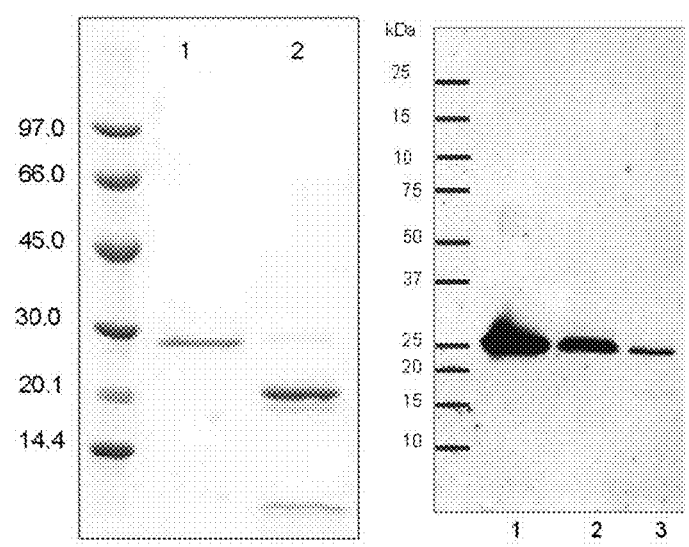
Figure 8:
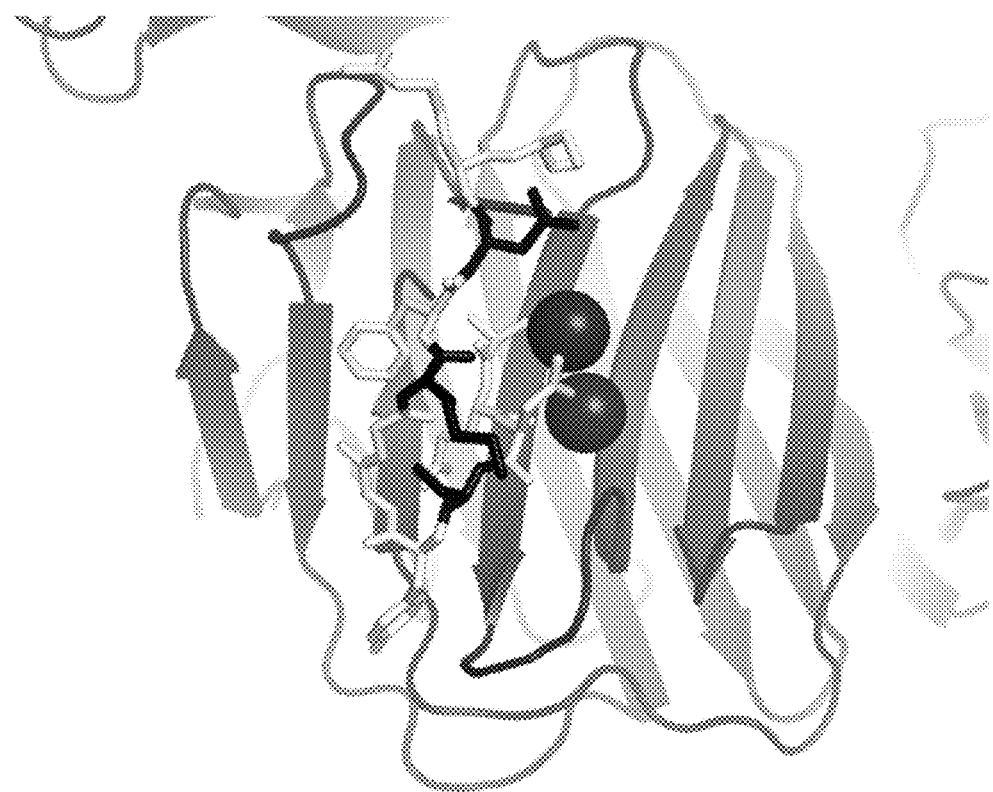

CNBr digestion of human SAP results in cleavage between 159M and 160W resulting in a new peptide where position 159 has been converted from methionine to homoserine lactone (termed 150-158-homoserine lactone). In western blotting from SDS-PAGE, SAP-E bound to the N-terminal 1-158-homoserine lactone polypeptide released by CNBr cleavage of SAP at residue Met159, but scarcely reacted with the 1-140 fragment released by chymotrypsin digestion in the absence of calcium (FIG. 8). The epitope recognised by SAP-E must therefore be in the region 140-158 which evidently comprises some denaturation resistant secondary structure since SAP-E binding is not potently inhibited by the peptides 136-147, 138-149, 140-151 and 112-119 in solution. This is consistent with the kinetic stability and resistance to denaturation of SAP (Manning, M. and Colón, W. (2004) *Biochemistry,* 43: 11248-11254).

FIG. 8 shows epitope mapping for monoclonal anti-human SAP antibody, SAP-E. A, complete amino acid sequence of human SAP showing the points at which it is cleaved by CNBr in 70% TFA (residue 159M) and by chymotrypsin, without reduction/carbamidomethylation, in ammonium bicarbonate in the absence of calcium, (residues 140Y and 144F). B, SDS-PAGE analysis of SAP cleaved with CNBr. Left panel: Coomassie blue stain; lane 1, untreated control SAP; lane 2, SAP after CNBr cleavage, showing trace residual uncleaved intact protomer and the expected fragments at approximately 20 kD (residues 1-158-homoserine-lactone) and 5 kD (160-204) respectively. These were precisely confirmed by mass spectrometry. Right panel: Western blot with SAP-5 showing intense staining of intact untreated SAP in lanes 1 (100 ng loaded) and 2 (10 ng), and also residual intact SAP and the larger residue 1-158-homoserine-lactone fragment in CNBr cleaved SAP in lanes 3 (600 ng), 4 (130 ng) and 5 (64 ng). Lane 6 contained isolated pure human CRP with which the SAP-5 did not react at all. C, SDS-PAGE analysis of SAP digested with chymotrypsin. Left panel: Coomassie blue stain; lane 1, untreated control SAP; lane 2, SAP after chymotrypsin digestion, showing the expected major fragments corresponding to residues 1-140 and 145-204. These were precisely confirmed by mass spectrometry. Right panel: Western blot with SAP-E showing intense staining of intact untreated SAP in lanes 1 (500 ng loaded) and 2 (100 ng), and also residual intact SAP in lanes 3 and 4 which contained the chymotrypsin digested SAP at different loadings. Very weak binding of SAP-E to the residue 1-140 fragment is seen only in lane 3 which was most heavily loaded. Lanes 5 (500 ng) and 6 (100 ng) contained isolated pure human CRP with which the SAP-E did not react at all. D, Sequence comparison between human SAP (h) and mouse SAP (m) for residues 136-147. Top panel, differences indicated above by residues shown in black in the murine sequence. Bottom panel, position of this extended loop with 140Y at its apex shown in white in the 3D subunit structure of human SAP. The different residues in the murine sequence are shown in black. The grey spheres represent the calcium atoms bound in the ligand binding pocket.

The conformational epitope recognised by SAP-K was identified by CLIPS® technology epitope mapping (Pepscan Presto BV) as the exposed peripheral loop, residues 121-131, at the circumference of the disc like pentameric native SAP molecule.

Figure 9:
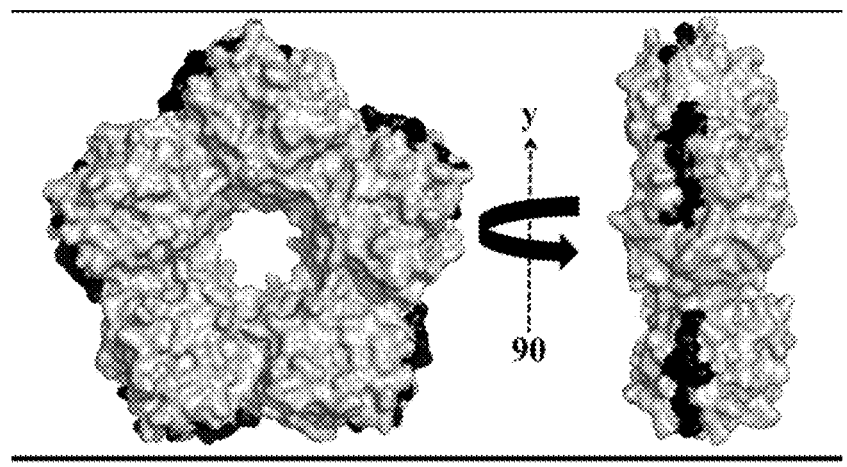
FIG. 9 shows the location of the epitopes on human SAP recognised by SAP-K (A, highlighted in black) and SAP-E (B, shown in white).
Figure 9:
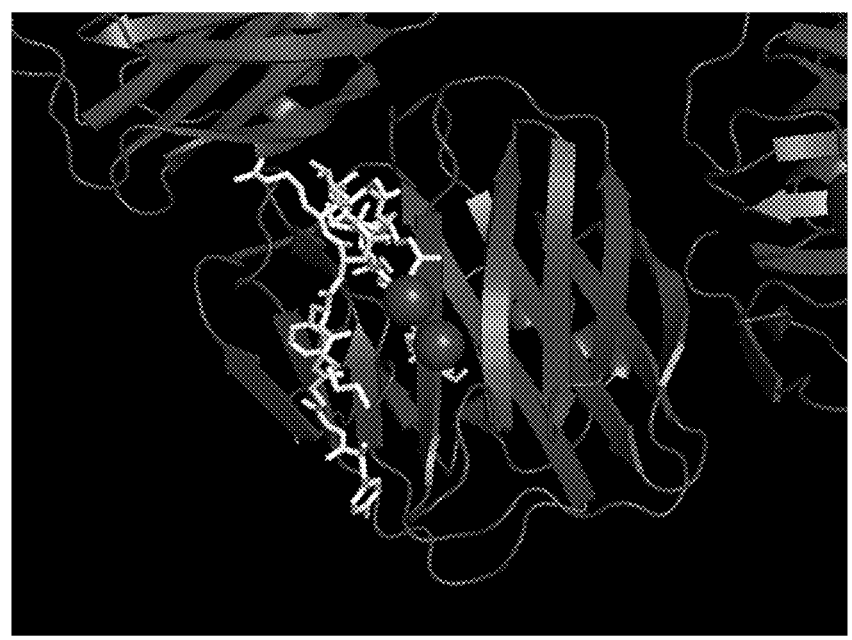

FIG. 9 shows the location of the epitopes on human SAP recognised by SAP-K (A, highlighted in black, as determined by CLIPS® technology) and SAP-E (B, shown in white, 140-158 as determined by binding results with the CNBr cleavage product of SAP and the fragment released by chymotrypsin digestion in the absence of calcium).

Example 15: Efficacy of SAP-K Mouse Monoclonal Anti-Human SAP Antibody in Clearing Amyloid Deposits In Vivo in the Mouse AA Amyloidosis Model The potency of SAP-K was compared with the action of the standard sheep polyclonal antibody in clearing established systemic AA amyloid deposits in mice.

Induction of AA Amyloidosis and Treatment

AA amyloidosis was induced and confirmed in wild-type C57BL/6 mice as detailed in Example 10 above. After loading the amyloid deposits with human SAP also detailed in Example 10, groups of mice were treated with 50 mg per mouse of total IgG as the whole IgG fraction (batch 2866) of the sheep polyclonal anti-human SAP antiserum providing a dose of 7 mg of actual anti-SAP antibody, isolated purified SAP-K at a dose of 5 mg per mouse, isolated purified SAP-K at a dose of 1 mg per mouse, and, as a negative control, isolated purified monoclonal mouse IgG2a antibody specific for an unrelated human antigen and unreactive with either human SAP or any murine antigen. All mice were killed 17 days later for estimation of amyloid load by Congo red staining.

Results

The mice treated with 5 mg of SAP-K showed the same remarkable clearance of splenic and hepatic amyloid deposits as seen with the 7 mg dose of sheep polyclonal antibody. Only trace specks of amyloid remained in the spleens of the treated mice and none at all was detected in many of the livers, contrasting sharply with the extensive splenic and hepatic amyloid deposits in all animals which received the irrelevant control mouse IgG2a antibody (Table 13). At the lower doses of 1 mg, 0.5 mg and 0.1 mg (data not shown for 0.5 mg and 0.1 mg) of SAP-K per mouse, there was no significant effect.

TABLE 13

Effect of monoclonal mouse IgG2a anti-human SAP antibody SAP-K on visceral amyloid deposits in mice with systemic AA amyloidosis.

| Group (treatment, group size) | Amyloid score median, range | |
|---|---|---|
| | Spleen | Liver |
| 1 (negative control mouse IgG2a, n = 8) | 4.08, 1.5-4.50 | 2.42, 2.0-2.67 |
| 2 (7 mg sheep polyclonal IgG anti-human SAP antibody, n = 5) | 1.17, 1.0-1.5 | 1.0, 0.67-1.17 |
| 3 (1 mg monoclonal mouse IgG2a anti-human SAP antibody, SAP-K, n = 10) | 3.5, 2.83-4.5 | 1.83, 1.0-2.83 |
| 4 (5 mg monoclonal mouse IgG2a anti-human SAP antibody, SAP-K, n = 10) | 1.25, 1.0-2.0 | 1.0, 1.0-1.33 |

Kruskal-Wallis test: spleen, P < 0.001; liver P, 0.001
Mann-Whitney tests*: 1 vs 2, spleen, P = 0.002; liver, P = 0.002; 1 vs 3, spleen, P = 0.173; liver, P = 0.083; 1 vs 4, spleen, P < 0.001; liver, P < 0.001; 2 vs 3, spleen, P = 0.0.001; liver, P = 0.019; 2 vs 4, spleen, P = 0.513; liver, P = 0.768; 3 vs 4, spleen, P < 0.001; liver, P = 0.004. *Due to the multiple comparisons, a P value of 0.01 or less is required for significance.

Discussion

These results demonstrate the efficacy in clearing amyloid deposits in vivo of a monoclonal anti-human SAP antibody, of the complement activating mouse IgG2a isotype, which specifically recognizes a conformational epitope. Thus monoclonal anti-human SAP antibodies for use according to the present invention can be directed at either predominantly sequence epitopes, such as antibody SAP-E, or at entirely conformational epitopes, such as SAP-K.

Example 16: Comparison of Efficacy of SAP-E and SAP-K in Clearing Systemic AA Amyloid Deposits in Mice, and Estimation of Plasma Anti-SAP Antibody Concentrations Induction of AA Amyloidosis and Treatment AA amyloidosis was induced and confirmed in wild-type C57BL/6 mice as detailed in Example 10 above. After loading the amyloid deposits with human SAP also detailed in Example 10, groups of mice were treated with 3 mg and 1 mg per mouse of the two different antibodies. A control group, in which amyloid was also induced, received just PBS instead of antibody and two further groups were given the known effective dose of 5 mg/mouse of each antibody. All mice were bled for assay of circulating anti-SAP antibody at days 1, 5 and 15 after dosing with antibody, and all were killed on day 21 for estimation of amyloid load by Congo red staining. All sera were assayed for anti-SAP activity using a robust immunoradiometric assay standardised with purified SAP-E and SAP-K respectively, spiked at known concentrations into normal mouse serum.

Results

Amyloid load was scored by four independent expert observers all blinded to the identity of each tissue examined. The scores of all observers were, as usual highly concordant and for statistical analysis, the total scores of all observers for both spleen and liver for each mouse were summed. Both antibodies were efficacious, as previously demonstrated, and there was a clear dose dependent effect but SAP-E was apparently more potent than SAP-K at the lower doses.

TABLE 14

Comparison of potency between SAP-E and SAP-K in clearing visceral AA amyloid deposits

| Group (treatment, no. of mice) | Spleen plus liver amyloid score median, range |
|---|---|
| C (negative control, PBS only) | 6.81, 4.25-8.0 |
| K5 (SAP-K 5 mg, n = 5) | 2.25, 2.25-2.5 |
| K3 (SAP-K 3 mg, n = 10) | 2.81, 2.0-4.25 |
| K1 (SAP-K 1 mg, n = 10) | 5.63, 4.0-6.5 |
| E5 (SAP-E 5 mg, n = 5) | 2.0, 1.5-2.38 |
| E3 (SAP-E 3 mg, n = 10) | 2.5, 2.0-5.0 |
| E1 (SAP-E 1 mg, n = 10) | 3.38, 2.5-5.63 |

Kruskal-Wallis test: $P < 0.001$
Mann-Whitney tests*: K5 vs E5, P = 0.095; K3 vs E3, P = 0.684; K1 vs E1, P = 0.001; K5 vs K3, P = 0.594; K5 vs K1, P = 0.001; K3 vs K1, P < 0.001; E5 vs E3, P = 0.008; E5 vs E1, P = 0.001; E3 vs E1, P = 0.004; K5 vs C, P = 0.001; E5 vs C, P = 0.001; K3 vs C, P < 0.001; E3 vs C, P < 0.001; K1 vs C,P = 0.043; E1 vs C, P < 0.001. *Due to the multiple comparisons, a P value of 0.01 or less is required for significance.

The concentrations of circulating anti-SAP antibody activity were strongly and consistently dose dependent after the single dose administered to all animals, apart from a single outlying individual in each of the lower dose groups. After the 1 mg per mouse dose, nothing above background was generally detectable even at day 1 in most mice. In contrast, after the 5 mg dose abundant antibody was still present at 15 days, and after 3 mg most mice had circulating antibody at day 5 but few after 15 days (Table 15). There was no significant difference between the patterns for SAP-E and SAP-K.

TABLE 15

Serum concentration of anti-SAP antibody after single intraperitoneal doses.

| Group (dose of anti-SAP antibody) | anti-SAP concentration after dosing median, range (μg/ml)* | | |
|---|---|---|---|
| | 1 day | 5 days | 15 days |
| K5 (SAP-K 5 mg) | 950, 840-1200 | 400, 300-480 | 45, 25-90 |
| E5 (SAP-E 5 mg) | 1000, 800-1500 | 600, 360-700 | 80, 15-113 |
| K3 (SAP-K 3 mg) | 240, 50-600 | 40, 8-280 | 8, 6-30 |
| E3 (SAP-E 3 mg) | 275, 4-480 | 48, 0-240 | 4, 2-68 |
| K1 (SAP-K 1 mg) | 7, 7-90 | 6, 5-38 | 4, 2-9 |
| E1 (SAP-E 1 mg) | 7, 6-280 | 7, 6-120 | 5, 3-12 |
| C (PBS only) | 5, 5-7 | 5, 5-13 | 5, 5-16 |

*Apparent anti-SAP antibody concentrations below 17 μg/ml are background for the assay and represent no genuine activity.

Discussion

In direct head to head comparison there was consistent evidence that SAP-E was slightly but significantly more potent than SAP-K. After administration of 1 mg per mouse no circulating anti-SAP antibody activity was detectable one day later, having evidently all localised to human SAP within the amyloid deposits. After the 3 mg dose abundant anti-SAP was present in the circulation at day 1 and was still present at day 5. After 5 mg per mouse there was still a significant concentration of anti-SAP in the blood after 15 days. These observations suggest that repeated small doses of anti-SAP antibody may be sufficient to trigger amyloid clearance.

Example 17: Comparison of Efficacy of Low Dose SAP-E and SAP-K in Clearing Systemic AA Amyloid Deposits in Mice Induction of AA Amyloidosis and Treatment AA amyloidosis was induced and confirmed in wild-type C57BL/6 mice as detailed in Example 10 above. After loading the amyloid deposits with human SAP as also detailed in Example 10, groups of mice (n=10 each) were treated with single doses of either 0.5 mg and 1 mg per mouse of the two different antibodies, or 6 repeated doses of 0.15 mg, given at 3 or 4 day intervals. A control group (n=9), in which amyloid was also induced, received just PBS instead of antibody and two further groups (n=3 each) were given the known effective dose of 5 mg/mouse of each antibody. All were killed on day 29 for estimation of amyloid load by Congo red staining.

Results

The low doses, including the repeated very low dose, showed significant efficacy in reducing amyloid load, especially in the liver. SAP-E was again apparently more potent than SAP-K.

TABLE 16

Comparison of potency between low doses of SAP-E and SAP-K in clearing visceral AA amyloid deposits

| | Amyloid score, (median, range) | |
|---|---|---|
| Group | Spleen | Liver |
| C, negative control PBS only | 4.5, 4.0-4.75 | 3.25, 2.0-4.0 |
| E1, SAP-E 1 mg | 1.25, 1.0-4.25 | 1.0, 0.5-1.25 |
| E0.5, SAP-E 0.5 mg | 4.75, 1.0-5.0 | 1.0, 0.5-3.5 |
| Erep, SAP-E 6 × 0.15 mg | 3.5, 2.0-4.5 | 0.5, 0.0-3.25 |
| K1, SAP-K 1 mg | 4.13, 1.0-5.0 | 1.0, 0.0-4.0 |
| K0.5, SAP-K 0.5 mg | 4.25, 1.75-4.5 | 1.13, 0.0-2.75 |
| Krep, SAP-K 6 × 0.15 mg | 4.38, 1.5-4.75 | 1.0, 0.0-2.25 |

Kruskal-Wallis test: spleen, P < 0.001; liver, P = 0.001
Mann-Whitney tests*: E1 vs C: spleen, P < 0.001; liver P < 0.001; E0.5 vs C: spleen, P = 0.604; liver P = 0.004; Erep vs C: spleen, P0.002; liver, P < 0.001; K1 vs C: spleen, P = 0.065; liver, P = 0.001; K0.5 vs C: spleen, P = 0.022; liver, P = 0.001; Krep vs C: spleen, P = 0.079; liver, P < 0.001; E1 vs E0.5: spleen, P = 0.005; liver P = 0.143; E1 vs Erep: spleen, P = 0.043; liver, P = 0.280; E0.5 vs Erep: spleen, P = 0.019; liver, P = 0.043; K1 vs K0.5: no significant differences; K1 vs Krep: no significant differences; K0.5 vs Krep: no significant differences; E1 vs K1: spleen, P = 0.015; liver, P = 0.353; E0.5 vs K0.5: no significant differences; Erep vs Krep: no significant differences. *Due to the multiple comparisons, a P value of 0.01 or less is required for significance.

Discussion

The significantly greater potency of SAP-E than SAP-K appears to be reproducible. The efficacy of even very low doses when administered repeatedly and the suggestion of greater effects on liver than spleen amyloid deposits are of interest and potential clinical significance.

Example 18: Activation of Complement by Humanised Monoclonal Anti-Human SAP Antibodies In Vitro Complement activation is essential for efficacy of amyloid clearing by anti-human SAP antibodies according to the present invention. The capacity of the humanised monoclonal antibodies, SAP-E H1L1 and SAP-K H3L0, to activate C3 in human and mouse serum was compared in vitro by adding different amounts of the isolated pure antibodies to either whole human serum containing a SAP concentration of 30 mg/l, or to whole mouse serum which had been spiked with isolated pure human SAP to this same concentration. In both cases the serum was fresh and complement sufficient and experimental conditions were optimal for complement activation with complement fixation test buffer (CFT) as the diluent.

The following mixtures were made (Table 17):

| Tube no. | Serum | Monoclonal anti-SAP antibody | Final concentrations (μg/ml) Anti-SAP | Human SAP |
|---|---|---|---|---|
| M1 | Mouse + human SAP | SAP-E H1L1 | 15 | 30 |
| M2 | Mouse + human SAP | SAP-E H1L1 | 30 | 30 |
| M3 | Mouse + human SAP | SAP-E H1L1 | 60 | 30 |
| M4 | Mouse + human SAP | SAP-E H1L1 | 120 | 30 |
| M5 | Mouse + human SAP | SAP-K H3L0 | 15 | 30 |
| M6 | Mouse + human SAP | SAP-K H3L0 | 30 | 30 |
| M7 | Mouse + human SAP | SAP-K H3L0 | 60 | 30 |
| M8 | Mouse + human SAP | SAP-K H3L0 | 120 | 30 |
| M9 | Mouse + human SAP | None | 0 | 30 |
| H1 | Human | SAP-E H1L1 | 15 | 30 |
| H2 | Human | SAP-E H1L1 | 30 | 30 |
| H3 | Human | SAP-E H1L1 | 60 | 30 |
| H4 | Human | SAP-E H1L1 | 120 | 30 |
| H5 | Human | SAP-K H3L0 | 15 | 30 |
| H6 | Human | SAP-K H3L0 | 30 | 30 |
| H7 | Human | SAP-K H3L0 | 60 | 30 |
| H8 | Human | SAP-K H3L0 | 120 | 30 |
| H9 | Human | None | 0 | 30 |

All tubes were incubated at 37° C. for 2 hours to enable complement activation to proceed. Since slow spontaneous activation always occurs in serum, two additional controls were provided, replicates of M9 and H9, designated M10 and H10, which were not incubated but were frozen at −80° C. immediately after mixing and then thawed just before assaying for C3 cleavage. Comparison between M/H9 and M/H10 enables distinction between spontaneous C3 cleavage and any additional activation produced by the anti-SAP antibody, as well as any effect of addition of human SAP alone t mouse serum.

C3 cleavage in human serum was assayed by two dimensional electroimmunophoresis using monospecific antibody against human C3. This method is of low sensitivity for mouse C3 cleavage because the different electrophoretic mobilities of mouse C3 are more difficult to distinguish reliably than is the case with human $C_3$. Mouse C3 cleavage was therefore assayed by agarose gel electrophoresis followed by immunoblotting with monospecific anti-mouse C3 antibody.

Results

Figure 10:
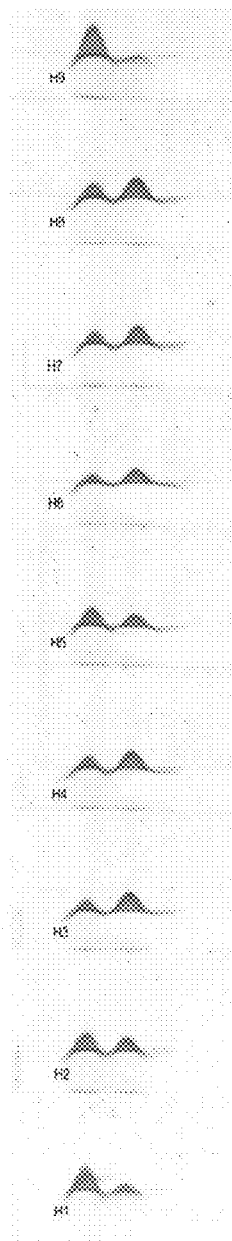
FIG. 10 shows C3 activation by humanised monoclonal anti-human SAP antibodies in whole human serum.

Both humanised antibodies efficiently activated human complement, evidenced by major dose dependent cleavage of C3, producing reduction in the size of the slower mobility native C3 immunoprecipitation peak and increase in the size of the faster cleaved C3c peak (FIG. 10).

FIG. 10 shows C3 activation by humanised monoclonal anti-human SAP antibodies in whole human serum.

Figure 11:
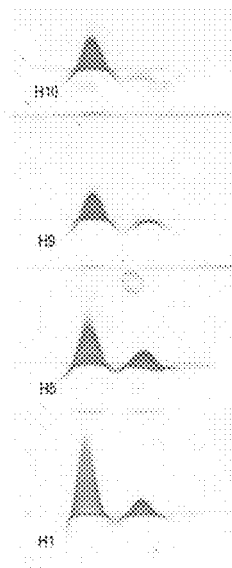
FIG. 11 shows C3 activation by low dose humanised monoclonal anti-human SAP antibodies in whole human serum.

In an assay including the control for baseline C3 cleavage in sample H10, it is clear that even the lowest dose of both anti-SAP antibodies produces more C3 cleavage than seen in the no antibody, spontaneous cleavage, control (FIG. 11).

FIG. 11 shows C3 activation by low dose humanised monoclonal anti-human SAP antibodies in whole human serum.

Very similar results were obtained for cleavage of mouse C3 in whole mouse serum supplemented with human SAP. Both antibodies showed dose dependent cleavage of native mouse C3 leading to decreased intensity of the slow mobility native C3 band and increased intensity of the faster mobility activated form. Also even the lowest dose of each antibody produced more C3 cleavage than was seen in the no antibody, spontaneous cleavage, control (FIG. 12).

Figure 12:
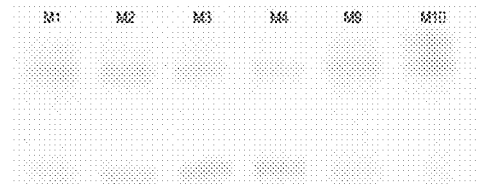
FIG. 12 shows C3 activation by humanised monoclonal anti-human SAP antibodies in whole mouse serum supplemented with pure human SAP.
Figure 12:
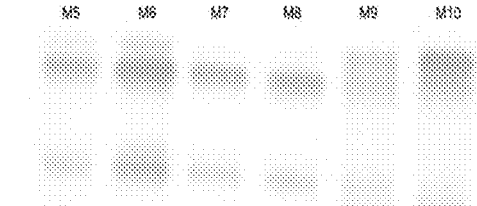
Figure 12:
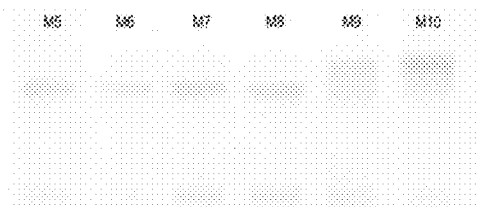

FIG. 12 shows C3 activation by humanised monoclonal anti-human SAP antibodies in whole mouse serum supplemented with pure human SAP.

Discussion

Both humanised monoclonal anti-human SAP antibodies efficiently activate complement in the presence of human SAP and are thus suitable candidates for use in treatment of systemic amyloidosis, and any other disease caused by extracellular amyloid deposits in the tissues, according to the present invention.

| SEQUENCE CONCORDANCE | |
|---|---|
| SEQ ID NO | Sequence description |
| 1 | SAP-E CDRH1 amino acid sequence |
| 2 | SAP-E CDRH2 amino acid sequence |
| 3 | SAP-E CDRH3 amino acid sequence |
| 4 | SAP-E CDRL1 amino acid sequence |
| 5 | SAP-E CDRL2 amino acid sequence |
| 6 | SAP-E CDRL3 amino acid sequence |
| 7 | SAP-E $V_H$ amino acid sequence |
| 8 | SAP-E $V_H$ DNA sequence |
| 9 | SAP-E $V_L$ amino acid sequence |
| 10 | SAP-E $V_L$ DNA sequence |
| 11 | SAP-K CDRH1 amino acid sequence |
| 12 | SAP-K CDRH2 amino acid sequence |
| 13 | SAP-K CDRH3 amino acid sequence |
| 14 | SAP-K CDRL1 amino acid sequence |

-continued

| SEQUENCE CONCORDANCE | |
|---|---|
| SEQ ID NO | Sequence description |
| 15 | SAP-K CDRL2 amino acid sequence |
| 16 | SAP-K CDRL3 amino acid sequence |
| 17 | SAP-K $V_H$ amino acid sequence |
| 18 | SAP-K $V_H$ DNA sequence |
| 19 | SAP-K $V_L$ amino acid sequence |
| 20 | SAP-K $V_L$ DNA sequence |
| 21 | SAP-E $V_H$ chimera amino acid sequence |
| 22 | SAP-E $V_L$ chimera amino acid sequence |
| 23 | SAP-K $V_H$ chimera amino acid sequence |
| 24 | SAP-K $V_L$ chimera amino acid sequence |
| 25 | IGHV1-69 human variable heavy chain germline acceptor amino acid sequence |
| 26 | JH1 minigene |
| 27 | SAP-E humanised $V_H$ variant H0 amino acid sequence |
| 28 | SAP-E humanised $V_H$ variant H1 amino acid sequence |
| 29 | SAP-E humanised $V_H$ variant H2 amino acid sequence |
| 30 | SAP-E humanised $V_H$ variant H3 amino acid sequence |
| 31 | SAP-E humanised $V_H$ variant H4 amino acid sequence |
| 32 | IGKV1-39 human variable light chain germline acceptor amino acid sequence |
| 33 | JK2 minigene |
| 34 | SAP-E humanised $V_L$ variant L0 amino acid sequence |
| 35 | SAP-E humanised $V_L$ variant L1 amino acid sequence |
| 36 | SAP-E humanised $V_L$ variant L2 amino acid sequence |
| 37 | SAP-K humanised $V_H$ variant H0 amino acid sequence |
| 38 | SAP-K humanised $V_H$ variant H1 amino acid sequence |
| 39 | SAP-K humanised $V_H$ variant H2 amino acid sequence |
| 40 | SAP-K humanised $V_H$ variant H3 amino acid sequence |
| 41 | SAP-K humanised $V_L$ variant L0 amino acid sequence |
| 42 | SAP-K humanised $V_L$ variant L1 amino acid sequence |
| 43 | *Homo sapiens* SAP amino acid sequence |
| 44 | *Mus musculus* SAP amino acid sequence |
| 45 | SAP-E VH chimera nucleotide sequence |
| 46 | SAP-E VL chimera nucleotide sequence |
| 47 | SAP-K VH chimera nucleotide sequence |
| 48 | SAP-K VL chimera nucleotide sequence |
| 49 | IGHV1-69 human variable heavy chain germline acceptor nucleotide sequence |
| 50 | IGHV1-39 human variable heavy chain germline acceptor nucleotide sequence |
| 51 | SAP-E humanised heavy chain V region variant H0 nucleotide sequence non-codon optimised |
| 52 | SAP-E humanised light chain V region variant L0 nucleotide sequence non-codon optimised |
| 53 | SAP-E humanised heavy chain V region variant H0 nucleotide sequence (codon optimised) |
| 54 | SAP-E humanised heavy chain V region variant H1 nucleotide sequence (codon optimised) |
| 55 | SAP-E humanised heavy chain V region variant H2 nucleotide sequence (codon optimised) |
| 56 | SAP-E humanised heavy chain V region variant H3 nucleotide sequence (codon optimised) |
| 57 | SAP-E humanised heavy chain V region variant H4 nucleotide sequence (codon optimised) |
| 58 | SAP-E humanised light chain V region variant L0 nucleotide sequence (codon optimised) |
| 59 | SAP-E humanised light chain V region variant L1 nucleotide sequence (codon optimised) |
| 60 | SAP-E humanised light chain V region variant L2 nucleotide sequence (codon optimised) |
| 61 | SAP-E humanised heavy chain H1 full mature nucleotide sequence (codon optimised) |
| 62 | SAP-E humanised heavy chain H1 full mature amino acid sequence |
| 63 | SAP-E humanised light chain L1 full mature nucleotide sequence (codon optimised) |
| 64 | SAP-E humanised light chain L1 full mature amino acid sequence |
| 65 | SAP-K humanised heavy chain V region variant H0 nucleotide sequence non-codon optimised |
| 66 | SAP-K humanised light chain V region variant L0 nucleotide sequence non-codon optimised |

SEQUENCE CONCORDANCE

| SEQ ID NO | Sequence description |
|---|---|
| 67 | SAP-K humanised heavy chain V region variant H0 nucleotide sequence (codon optimised) |
| 68 | SAP-K humanised heavy chain V region variant H1 nucleotide sequence (codon optimised) |
| 69 | SAP-K humanised heavy chain V region variant H2 nucleotide sequence (codon optimised) |
| 70 | SAP-K humanised heavy chain V region variant H3 nucleotide sequence (codon optimised) |
| 71 | SAP-K humanised light chain V region variant L0 nucleotide sequence (codon optimised) |
| 72 | SAP-K humanised light chain V region variant L1 nucleotide sequence (codon optimised) |
| 73 | SAP-K humanised light chain V region variant L0 91A nucleotide sequence (codon optimised) |
| 74 | SAP-K humanised light chain V region variant L0 91A amino acid sequence |
| 75 | SAP-K humanised H3 heavy chain nucleotide sequence (codon optimised) |
| 76 | SAP-K humanised H3 heavy chain amino acid sequence |
| 77 | SAP-K humanised L0 light chain nucleotide sequence (codon optimised) |
| 78 | SAP-K humanised L0 light chain amino acid sequence |
| 79 | Signal sequence for immunoglobulin chains |

The invention claimed is:

1. A method of treating a human afflicted with a disease associated with amyloid deposition, which method comprises the step of administering to said human a therapeutically effective amount of a serum amyloid P component (SAP) depleting compound and a humanised antibody, wherein the humanised antibody comprises SEQ ID NO:1 (CDRH1), SEQ ID NO:2 (CDRH2), SEQ ID NO:3 (CDRH3), SEQ ID NO:4 (CDRL1), SEQ ID NO:5 (CDRL2), and SEQ ID NO:6 (CDRL3), which binds to serum amyloid P component (SAP).

2. The method according to claim 1, wherein the SAP depleting compound is to be administered first.

3. A method according to claim 1, wherein the humanised antibody is to be administered when substantially all of the SAP circulating in the human has been cleared.

4. A method according to claim 1, wherein the disease is selected from the group consisting of: systemic amyloidosis, local amyloidosis, type 2 diabetes, dialysis-related amyloidosis, monoclonal immunoglobulin chain (AL) amyloidosis and cerebral amyloid angiopathy.

5. A method according to claim 1, wherein the SAP depleting compound is a D-proline derivative or a glycerol cyclic pyruvate derivative.

6. A method according to claim 5, wherein the D-proline derivative is CPHPC or a diester thereof.

7. A method of treating a human afflicted with a disease associated with amyloid deposition, which method comprises the step of administering to said human a therapeutically effective amount of a humanised antibody, comprising SEQ ID NO:1 (CDRH1), SEQ ID NO:2 (CDRH2), SEQ ID NO:3 (CDRH3), SEQ ID NO:4 (CDRL1), SEQ ID NO:5 (CDRL2), and SEQ ID NO:6 (CDRL3), which binds to serum amyloid P component (SAP).

8. A method according to claim 7, wherein the disease is selected from the group consisting of: systemic amyloidosis, local amyloidosis, type 2 diabetes, dialysis-related amyloidosis, monoclonal immunoglobulin chain (AL) amyloidosis and cerebral amyloid angiopathy.

9. A method of treating a human afflicted with a disease associated with amyloid deposition, which method comprises the step of administering to said human a therapeutically effective amount of a humanised antibody, comprising a heavy chain variable region as shown in SEQ ID NO: 28; and a light chain variable region as shown in SEQ ID NO:35.

10. A method according to claim 9, wherein the disease is selected from the group consisting of: systemic amyloidosis, local amyloidosis, type 2 diabetes, dialysis-related amyloidosis, monoclonal immunoglobulin chain (AL) amyloidosis and cerebral amyloid angiopathy.

11. A method of treating a human afflicted with a disease associated with amyloid deposition, which method comprises the step of administering to said human a therapeutically effective amount of a humanised antibody, comprising a heavy chain as shown in SEQ ID NO:62; and a light chain as shown in SEQ ID NO:64.

12. A method according to claim 11, wherein the disease is selected from the group consisting of: systemic amyloidosis, local amyloidosis, type 2 diabetes, dialysis-related amyloidosis, monoclonal immunoglobulin chain (AL) amyloidosis and cerebral amyloid angiopathy.

* * * * *

SEQUENCE LISTING

```
<160> NUMBER OF SEQ ID NOS: 79

<210> SEQ ID NO 1
<211> LENGTH: 5
<212> TYPE: PRT
<213> ORGANISM: Mus musculus
<220> FEATURE:
<223> OTHER INFORMATION: SAP-E CDRH1 amino acid

<400> SEQUENCE: 1

Thr Tyr Asn Met His
1               5

<210> SEQ ID NO 2
<211> LENGTH: 17
<212> TYPE: PRT
<213> ORGANISM: Mus musculus
<220> FEATURE:
<223> OTHER INFORMATION: SAP-E CDRH2 amino acid

<400> SEQUENCE: 2

Tyr Ile Tyr Pro Gly Asp Gly Asn Ala Asn Tyr Asn Gln Gln Phe Lys
1               5                   10                  15

Gly

<210> SEQ ID NO 3
<211> LENGTH: 13
<212> TYPE: PRT
<213> ORGANISM: Mus musculus
<220> FEATURE:
<223> OTHER INFORMATION: SAP-E CDRH3 amino acid

<400> SEQUENCE: 3

Gly Asp Phe Asp Tyr Asp Gly Gly Tyr Tyr Phe Asp Ser
1               5                   10

<210> SEQ ID NO 4
<211> LENGTH: 11
```

```
<212> TYPE: PRT
<213> ORGANISM: Mus musculus
<220> FEATURE:
<223> OTHER INFORMATION: SAP-E CDRL1 amino acid

<400> SEQUENCE: 4

Arg Ala Ser Glu Asn Ile Tyr Ser Tyr Leu Ala
1               5                   10

<210> SEQ ID NO 5
<211> LENGTH: 7
<212> TYPE: PRT
<213> ORGANISM: Mus musculus
<220> FEATURE:
<223> OTHER INFORMATION: SAP-E CDRL2 amino acid

<400> SEQUENCE: 5

Asn Ala Lys Thr Leu Ala Glu
1               5

<210> SEQ ID NO 6
<211> LENGTH: 9
<212> TYPE: PRT
<213> ORGANISM: Mus musculus
<220> FEATURE:
<223> OTHER INFORMATION: SAP-E CDRL3 amino acid

<400> SEQUENCE: 6

Gln His His Tyr Gly Ala Pro Leu Thr
1               5

<210> SEQ ID NO 7
<211> LENGTH: 120
<212> TYPE: PRT
<213> ORGANISM: Mus musculus
<220> FEATURE:
<223> OTHER INFORMATION: SAP-E VH amino acid

<400> SEQUENCE: 7

Gln Ala Ser Leu Gln Gln Ser Gly Thr Glu Leu Val Arg Ser Gly Ala
1               5                   10                  15

Ser Val Lys Met Ser Cys Lys Ala Ser Gly Phe Thr Phe Ala Thr Tyr
            20                  25                  30

Asn Met His Trp Ile Lys Gln Thr Pro Gly Gln Gly Leu Glu Trp Ile
        35                  40                  45

Gly Tyr Ile Tyr Pro Gly Asp Gly Asn Ala Asn Tyr Asn Gln Gln Phe
    50                  55                  60

Lys Gly Lys Ala Thr Leu Thr Ala Asp Thr Ser Ser Asn Thr Ala Tyr
65                  70                  75                  80

Met Gln Ile Ser Ser Leu Thr Ser Glu Asp Ser Ala Val Tyr Phe Cys
                85                  90                  95

Arg Asp Phe Asp Tyr Asp Gly Gly Tyr Tyr Phe Asp Ser Trp Gly Gln
            100                 105                 110

Gly Thr Thr Leu Thr Val Ser Ser
        115                 120

<210> SEQ ID NO 8
<211> LENGTH: 366
<212> TYPE: DNA
<213> ORGANISM: Mus musculus
<220> FEATURE:
<223> OTHER INFORMATION: SAP-E VH DNA

<400> SEQUENCE: 8
```

```
caggcttctc tacagcagtc tgggactgag ctggtgaggt ctggggcctc agtgaagatg    60
tcctgcaagg cttctggctt cacatttgcc acttacaata tgcactggat taagcagaca   120
cccggacagg gcctggaatg gattgggtat atttatcctg agatggtaa tgctaactac    180 aatcagcagt tcaagggcaa ggccacattg actgcagaca catcctccaa cacagcctac   240
atgcagatca gcagcctgac atctgaagac tctgcggtct atttctgtgc aagaggggac   300
tttgattacg acggagggta ctactttgac tcctggggcc agggcaccac tctcacagtc   360
tcctca                                                              366
```

<210> SEQ ID NO 9
<211> LENGTH: 107
<212> TYPE: PRT
<213> ORGANISM: Mus musculus
<220> FEATURE:
<223> OTHER INFORMATION: SAP-E VL amino acid

<400> SEQUENCE: 9

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Arg Ser Pro Gln Leu Leu Val
        35                  40                  45

His Asn Ala Lys Thr Leu Ala Glu Gly Val Pro Ser Arg Val Ser Gly
    50                  55                  60

Ser Gly Ser Gly Thr His Phe Ser Leu Lys Ile Asn Gly Leu Gln Pro
65                  70                  75                  80

Glu Asp Phe Gly Asn Tyr Tyr Cys Gln His His Tyr Gly Ala Pro Leu
                85                  90                  95

Thr Phe Gly Ala Gly Thr Lys Leu Glu Leu Lys
            100                 105

<210> SEQ ID NO 10
<211> LENGTH: 321
<212> TYPE: DNA
<213> ORGANISM: Mus musculus
<220> FEATURE:
<223> OTHER INFORMATION: SAP-E VL DNA

<400> SEQUENCE: 10

```
gacatccaga tgactcagtc tccagcctcc ctatctgcat ctgtgggaga aactgtcacc    60
atcacatgtc gagcaagtga gaatatttac agttatttag catggtatca gcagaaacag   120
ggaagatccc ctcagctcct ggtccataat gcaaaaacct agcagaagg tgtgccatca    180 agggtcagtg gcagtggatc aggcacacac ttttctctga agatcaacgg cctgcagcct   240
gaagattttg ggaattatta ctgtcaacat cattatggtg ctccgctcac gttcggtgct   300
gggaccaagc tggaactgaa a                                             321
```

<210> SEQ ID NO 11
<211> LENGTH: 5
<212> TYPE: PRT
<213> ORGANISM: Mus musculus
<220> FEATURE:
<223> OTHER INFORMATION: SAP-K CDRH1 amino acid

<400> SEQUENCE: 11

Ser Tyr Trp Met His

```
<210> SEQ ID NO 12
<211> LENGTH: 17
<212> TYPE: PRT
<213> ORGANISM: Mus musculus
<220> FEATURE:
<223> OTHER INFORMATION: SAP-K CDRH2 amino acid

<400> SEQUENCE: 12

Met Ile His Pro Asn Ser Val Asn Thr Asn Tyr Asn Glu Lys Phe Lys
1               5                   10                  15

Ser

<210> SEQ ID NO 13
<211> LENGTH: 10
<212> TYPE: PRT
<213> ORGANISM: Mus musculus
<220> FEATURE:
<223> OTHER INFORMATION: SAP-K CDRH3 amino acid

<400> SEQUENCE: 13

Arg Asn Asp Tyr Tyr Trp Tyr Phe Asp Val
1               5                   10

<210> SEQ ID NO 14
<211> LENGTH: 11
<212> TYPE: PRT
<213> ORGANISM: Mus musculus
<220> FEATURE:
<223> OTHER INFORMATION: SAP-K CDRL1 amino acid

<400> SEQUENCE: 14

Lys Ala Ser Gln Asn Val Asn Ser Asn Val Ala
1               5                   10

<210> SEQ ID NO 15
<211> LENGTH: 7
<212> TYPE: PRT
<213> ORGANISM: Mus musculus
<220> FEATURE:
<223> OTHER INFORMATION: SAP-K CDRL2 amino acid

<400> SEQUENCE: 15

Ser Ala Ser Tyr Arg Tyr Ser
1               5

<210> SEQ ID NO 16
<211> LENGTH: 9
<212> TYPE: PRT
<213> ORGANISM: Mus musculus
<220> FEATURE:
<223> OTHER INFORMATION: SAP-K CDRL3 amino acid

<400> SEQUENCE: 16

Gln Gln Cys Asn Asn Tyr Pro Phe Thr
1               5

<210> SEQ ID NO 17
<211> LENGTH: 119
<212> TYPE: PRT
<213> ORGANISM: Mus musculus
<220> FEATURE:
<223> OTHER INFORMATION: SAP-K VH amino acid

<400> SEQUENCE: 17
```

Gln Val Gln Leu Gln Gln Pro Gly Ala Glu Leu Ile Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Val Asn Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Asn Asp Tyr Tyr Trp Tyr Phe Asp Val Trp Gly Thr Gly
            100                 105                 110

Thr Thr Val Thr Val Ser Ser
            115

<210> SEQ ID NO 18
<211> LENGTH: 357
<212> TYPE: DNA
<213> ORGANISM: Mus musculus
<220> FEATURE:
<223> OTHER INFORMATION: SAP-K VH DNA

<400> SEQUENCE: 18
caggtccaac tgcagcagcc tggggctgag ctgataaagc ctggggcttc agtgaagttg     60
tcctgcaagg cttctggcta cactttcacc agctactgga tgcactgggt gaagcagagg    120
cctggacaag gccttgagtg gattggaatg attcatccta atagtgttaa tactaactac    180
aatgagaagt tcaagagtaa ggccacactg actgtagaca atcctccag cacagcctac     240 atgcaactca acagcctgac atctgaggac tctgcggtct attactgtgc aagacggaat    300
gattactact ggtacttcga tgtctggggc acagggacca cggtcaccgt ctcctca       357

<210> SEQ ID NO 19
<211> LENGTH: 107
<212> TYPE: PRT
<213> ORGANISM: Mus musculus
<220> FEATURE:
<223> OTHER INFORMATION: SAP-K VL amino acid

<400> SEQUENCE: 19

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asn Ser Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Cys Asn Asn Tyr Pro Phe
                85                  90                  95

Thr Phe Gly Ser Gly Thr Lys Leu Glu Ile Lys
            100                 105

<210> SEQ ID NO 20

<211> LENGTH: 321
<212> TYPE: DNA
<213> ORGANISM: Mus musculus
<220> FEATURE:
<223> OTHER INFORMATION: SAP-K VL DNA

<400> SEQUENCE: 20

```
gacattgtga tgacccagtc tcaaaaattc atgtccacat cagtaggaga cagggtcagc    60
gtcacctgca aggccagtca gaatgtgaat tctaatgtag cctggtatca acagaaacca   120
gggcaatctc ctaaagcact gatttactcg gcttcctacc ggtacagtgg agtccctgat   180
cgcttcacag gcagtggatc tgggacagat tcactctca ccatcaccaa tgtgcagtct   240
gaagacttgg cagagtattt ctgtcagcaa tgtaacaact atccattcac gttcggctcg   300
gggacaaagt tggaaataaa a                                              321
```

<210> SEQ ID NO 21
<211> LENGTH: 444
<212> TYPE: PRT
<213> ORGANISM: Artificial
<220> FEATURE:
<223> OTHER INFORMATION: SAP-E VH chimera amino acid

<400> SEQUENCE: 21

```
Gln Ala Ser Leu Gln Gln Ser Gly Thr Glu Leu Val Arg Ser Gly Ala
1               5                   10                  15

Ser Val Lys Met Ser Cys Lys Ala Ser Gly Phe Thr Phe Ala Thr Tyr
            20                  25                  30

Asn Met His Trp Ile Lys Gln Thr Pro Gly Gln Gly Leu Glu Trp Ile
        35                  40                  45

Gly Tyr Ile Tyr Pro Gly Asp Gly Asn Ala Asn Tyr Asn Gln Gln Phe
    50                  55                  60

Lys Gly Lys Ala Thr Leu Thr Ala Asp Thr Ser Ser Asn Thr Ala Tyr
65                  70                  75                  80

Met Gln Ile Ser Ser Leu Thr Ser Glu Asp Ser Ala Val Tyr Phe Cys
                85                  90                  95

Arg Asp Phe Asp Tyr Asp Gly Gly Tyr Tyr Phe Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
```

```
                260               265               270
Glu Val Lys Phe Asn Trp Tyr Val Asp Gly Val Glu Val His Asn Ala
            275               280               285
Lys Thr Lys Pro Arg Glu Glu Gln Tyr Asn Ser Tyr Val Val Ser Val
        290               295               300
Leu Thr Val Leu His Gln Asp Trp Leu Asn Gly Lys Glu Tyr Lys Cys
305               310               315               320
Lys Val Ser Asn Lys Ala Leu Pro Ala Pro Ile Glu Lys Thr Ile Ser
                325               330               335
Lys Ala Lys Gly Gln Pro Arg Glu Pro Gln Val Tyr Thr Leu Pro Pro
            340               345               350
Ser Arg Asp Glu Leu Thr Lys Asn Gln Val Ser Leu Thr Cys Leu Val
        355               360               365
Lys Gly Phe Tyr Pro Ser Asp Ile Ala Val Glu Trp Glu Ser Asn Gly
    370               375               380
Gln Pro Glu Asn Asn Tyr Lys Thr Thr Pro Pro Val Leu Asp Ser Asp
385               390               395               400
Gly Ser Phe Phe Lys Lys Leu Thr Val Asp Lys Ser Arg Trp Gln Gln
                405               410               415
Gly Asn Val Phe Ser Cys Ser Val Met His Glu Ala Leu His Asn His
            420               425               430
Tyr Thr Gln Lys Ser Leu Ser Leu Ser Pro Gly Lys
        435               440

<210> SEQ ID NO 22
<211> LENGTH: 214
<212> TYPE: PRT
<213> ORGANISM: Artificial Sequence
<220> FEATURE:
<223> OTHER INFORMATION: SAP-E VL chimera amino acid sequence

<400> SEQUENCE: 22

Asp Ile Gln Met Thr Gln Ser Pro Ala Ser Leu Ser Ala Ser Val Gly
1               5                  10                  15
Glu Thr Val Thr Ile Thr Cys Arg Ala Ser Glu Asn Ile Tyr Ser Tyr
            20                  25                  30
Leu Ala Trp Tyr Gln Gln Lys Gln Gly Arg Ser Pro Gln Leu Leu Val
        35                  40                  45
His Asn Ala Lys Thr Leu Ala Glu Gly Val Pro Ser Arg Val Ser Gly
    50                  55                  60
Ser Gly Ser Gly Thr His Phe Ser Leu Lys Ile Asn Gly Leu Gln Pro
65                  70                  75                  80
Glu Asp Phe Gly Asn Tyr Tyr Cys Gln His His Tyr Gly Ala Pro Leu
                85                  90                  95
Thr Phe Gly Ala Gly Thr Lys Leu Glu Leu Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
```

```
                180              185                190
Ala Cys Glu Val Thr His Gln Gly Leu Ser Ser Pro Val Thr Lys Ser
            195                200                205

Phe Asn Arg Gly Glu Cys
    210

<210> SEQ ID NO 23
<211> LENGTH: 443
<212> TYPE: PRT
<213> ORGANISM: Artificial Sequence
<220> FEATURE:
<223> OTHER INFORMATION: SAP-K VH chimera amino acid sequence

<400> SEQUENCE: 23

Gln Val Gln Leu Gln Gln Pro Gly Ala Glu Leu Ile Lys Pro Gly Ala
1               5                  10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Val Asn Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Asn Asp Tyr Tyr Trp Tyr Phe Asp Val Trp Gly Thr Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Tyr Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
```

```
                325                 330                 335
Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Lys Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 24
<211> LENGTH: 214
<212> TYPE: PRT
<213> ORGANISM: Artificial Sequence
<220> FEATURE:
<223> OTHER INFORMATION: SAP-K VL chimera amino acid sequence

<400> SEQUENCE: 24

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asn Ser Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Cys Asn Asn Tyr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 98
<212> TYPE: PRT
```

<213> ORGANISM: Homo sapiens
<220> FEATURE:
<223> OTHER INFORMATION: IGHV1-69 human variable heavy chain germline
      acceptor amino acid sequence

<400> SEQUENCE: 25

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 26
<211> LENGTH: 17
<212> TYPE: PRT
<213> ORGANISM: Homo sapiens
<220> FEATURE:
<223> OTHER INFORMATION: JH1 minigene

<400> SEQUENCE: 26

Ala Glu Tyr Phe Gln His Trp Gly Gln Gly Thr Leu Val Thr Val Ser
1               5                   10                  15

Ser

<210> SEQ ID NO 27
<211> LENGTH: 120
<212> TYPE: PRT
<213> ORGANISM: Artificial Sequence
<220> FEATURE:
<223> OTHER INFORMATION: SAP-E humanised VH variant H0 amino acid       sequence

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
                20                  25                  30

Asn Met His Trp Val Arg Gln Ala Pro Gly Gln Gly Leu Glu Trp Met
            35                  40                  45

Gly Tyr Ile Tyr Pro Gly Asp Gly Asn Ala Asn Tyr Asn Gln Gln Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Arg Asp Phe Asp Tyr Asp Gly Tyr Tyr Phe Asp Ser Trp Gly Gln
                100                 105                 110

Gly Thr Leu Val Thr Val Ser Ser
            115                 120

<210> SEQ ID NO 28
<211> LENGTH: 120

```
<212> TYPE: PRT
<213> ORGANISM: Artificial Sequence
<220> FEATURE:
<223> OTHER INFORMATION: SAP-E humanised VH variant H1 amino acid        sequence

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ala Thr Tyr
            20                  25                  30

Asn Met His Trp Val Arg Gln Ala Pro Gly Gln Gly Leu Glu Trp Met
        35                  40                  45

Gly Tyr Ile Tyr Pro Gly Asp Gly Asn Ala Asn Tyr Asn Gln Gln Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Arg Asp Phe Asp Tyr Asp Gly Gly Tyr Tyr Phe Asp Ser Trp Gly Gln
            100                 105                 110

Gly Thr Leu Val Thr Val Ser Ser
        115                 120

<210> SEQ ID NO 29
<211> LENGTH: 120
<212> TYPE: PRT
<213> ORGANISM: Artificial Sequence
<220> FEATURE:
<223> OTHER INFORMATION: SAP-E humanised VH variant H2 amino acid        sequence

<400> SEQUENCE: 29

Gln Ala Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ala Thr Tyr
            20                  25                  30

Asn Met His Trp Val Arg Gln Ala Pro Gly Gln Gly Leu Glu Trp Met
        35                  40                  45

Gly Tyr Ile Tyr Pro Gly Asp Gly Asn Ala Asn Tyr Asn Gln Gln Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Arg Asp Phe Asp Tyr Asp Gly Gly Tyr Tyr Phe Asp Ser Trp Gly Gln
            100                 105                 110

Gly Thr Leu Val Thr Val Ser Ser
        115                 120

<210> SEQ ID NO 30
<211> LENGTH: 120
<212> TYPE: PRT
<213> ORGANISM: Artificial Sequence
<220> FEATURE:
<223> OTHER INFORMATION: SAP-E humanised VH variant H3 amino acid sequence

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ala Thr Tyr
```

```
                20                  25                  30
Asn Met His Trp Val Arg Gln Ala Pro Gly Gln Gly Leu Glu Trp Ile
            35                  40                  45
Gly Tyr Ile Tyr Pro Gly Asp Gly Asn Ala Asn Tyr Asn Gln Gln Phe
        50                  55                  60
Lys Gly Arg Ala Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Arg Asp Phe Asp Tyr Asp Gly Gly Tyr Tyr Phe Asp Ser Trp Gly Gln
            100                 105                 110
Gly Thr Leu Val Thr Val Ser Ser
            115                 120
```

<210> SEQ ID NO 31
<211> LENGTH: 120
<212> TYPE: PRT
<213> ORGANISM: Artificial Sequence
<220> FEATURE:
<223> OTHER INFORMATION: SAP-E humanised VH variant H4 amino acid sequence

<400> SEQUENCE: 31

```
Gln Val Gln Leu Val Gln Ser Gly Ala Glu Val Lys Lys Pro Gly Ser
1               5                   10                  15
Ser Val Lys Val Ser Cys Lys Ala Ser Gly Phe Thr Phe Ala Thr Tyr
                20                  25                  30
Asn Met His Trp Val Arg Gln Ala Pro Gly Gln Gly Leu Glu Trp Ile
            35                  40                  45
Gly Tyr Ile Tyr Pro Gly Asp Gly Asn Ala Asn Tyr Asn Gln Gln Phe
        50                  55                  60
Lys Gly Arg Ala Thr Leu Thr Ala Asp Thr Ser Thr Ser Thr Ala Tyr
65                  70                  75                  80
Met Glu Leu Ser Ser Leu Arg Ser Glu Asp Thr Ala Val Tyr Phe Cys
                85                  90                  95
Arg Asp Phe Asp Tyr Asp Gly Gly Tyr Tyr Phe Asp Ser Trp Gly Gln
            100                 105                 110
Gly Thr Leu Val Thr Val Ser Ser
            115                 120
```

<210> SEQ ID NO 32
<211> LENGTH: 95
<212> TYPE: PRT
<213> ORGANISM: Homo sapiens
<220> FEATURE:
<223> OTHER INFORMATION: IGKV1-39 human variable light chain germline
      acceptor amino acid sequence

<400> SEQUENCE: 32

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
                20                  25                  30
Leu Asn Trp Tyr Gln Gln Lys Pro Gly Lys Ala Pro Lys Leu Leu Ile
            35                  40                  45
Tyr Ala Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Tyr Ser Thr Pro
                85                  90                  95
```

```
<210> SEQ ID NO 33
<211> LENGTH: 12
<212> TYPE: PRT
<213> ORGANISM: Homo sapiens
<220> FEATURE:
<223> OTHER INFORMATION: JK2 minigene

<400> SEQUENCE: 33

Tyr Thr Phe Gly Gln Gly Thr Lys Leu Glu Ile Lys
1               5                   10
```

```
<210> SEQ ID NO 34
<211> LENGTH: 107
<212> TYPE: PRT
<213> ORGANISM: Artificial Sequence
<220> FEATURE:
<223> OTHER INFORMATION: SAP-E humanised VL variant L0 amino acid sequence

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
                20                  25                  30

Leu Ala Trp Tyr Gln Gln Lys Pro Gly Lys Ala Pro Lys Leu Leu Ile
            35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Ala Pro Leu
                85                  90                  95

Thr Phe Gly Gln Gly Thr Lys Leu Glu Ile Lys
            100                 105
```

```
<210> SEQ ID NO 35
<211> LENGTH: 107
<212> TYPE: PRT
<213> ORGANISM: Artificial Sequence
<220> FEATURE:
<223> OTHER INFORMATION: SAP-E humanised VL variant L1 amino acid sequence

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
                20                  25                  30

Leu Ala Trp Tyr Gln Gln Lys Pro Gly Lys Ala Pro Lys Leu Leu Ile
            35                  40                  45

His Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Ala Pro Leu
                85                  90                  95

Thr Phe Gly Gln Gly Thr Lys Leu Glu Ile Lys
            100                 105
```

<210> SEQ ID NO 36
<211> LENGTH: 107
<212> TYPE: PRT
<213> ORGANISM: Artificial Sequence
<220> FEATURE:
<223> OTHER INFORMATION: SAP-E humanised VL variant L2 amino acid sequence

<400> SEQUENCE: 36

```
Asp Ile Gln Met Thr Gln Ser Pro Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

His Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Gly Ala Pro Leu
                85                  90                  95

Thr Phe Gly Gln Gly Thr Lys Leu Glu Ile Lys
            100                 105
```

<210> SEQ ID NO 37
<211> LENGTH: 119
<212> TYPE: PRT
<213> ORGANISM: Artificial Sequence
<220> FEATURE:
<223> OTHER INFORMATION: SAP-K humanised VH variant H0 amino acid sequence

<400> SEQUENCE: 37

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Trp Met His Trp Val Arg Gln Ala Pro Gly Gln Gly Leu Glu Trp Met
        35                  40                  45

Gly Met Ile His Pro Asn Ser Val Asn Thr Asn Tyr Asn Glu Lys Phe
    50                  55                  60

Lys Ser Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asn Asp Tyr Tyr Trp Tyr Phe Asp Val Trp Gly Gln Gly
            100                 105                 110

Thr Leu Val Thr Val Ser Ser
        115
```

<210> SEQ ID NO 38
<211> LENGTH: 119
<212> TYPE: PRT
<213> ORGANISM: Artificial Sequence
<220> FEATURE:
<223> OTHER INFORMATION: SAP-K humanised VH variant H1 amino acid sequence

<400> SEQUENCE: 38

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
```

```
                20                  25                  30
Trp Met His Trp Val Arg Gln Ala Pro Gly Gln Gly Leu Glu Trp Met
            35                  40                  45

Gly Met Ile His Pro Asn Ser Val Asn Thr Asn Tyr Asn Glu Lys Phe
        50                  55                  60

Lys Ser Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asn Asp Tyr Tyr Trp Tyr Phe Asp Val Trp Gly Gln Gly
            100                 105                 110

Thr Leu Val Thr Val Ser Ser
            115

<210> SEQ ID NO 39
<211> LENGTH: 119
<212> TYPE: PRT
<213> ORGANISM: Artificial Sequence
<220> FEATURE:
<223> OTHER INFORMATION: SAP-K humanised VH variant H2 amino acid sequence

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Met Ile His Pro Asn Ser Val Asn Thr Asn Tyr Asn Glu Lys Phe
        50                  55                  60

Lys Ser Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asn Asp Tyr Tyr Trp Tyr Phe Asp Val Trp Gly Gln Gly
            100                 105                 110

Thr Leu Val Thr Val Ser Ser
            115

<210> SEQ ID NO 40
<211> LENGTH: 119
<212> TYPE: PRT
<213> ORGANISM: Artificial Sequence
<220> FEATURE:
<223> OTHER INFORMATION: SAP-K humanised VH variant H3 amino acid sequence

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Met Ile His Pro Asn Ser Val Asn Thr Asn Tyr Asn Glu Lys Phe
        50                  55                  60

Lys Ser Arg Ala Thr Leu Thr Val Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Arg Asn Asp Tyr Tyr Trp Tyr Phe Asp Val Trp Gly Gln Gly
            100                 105                 110

Thr Leu Val Thr Val Ser Ser
        115

<210> SEQ ID NO 41
<211> LENGTH: 107
<212> TYPE: PRT
<213> ORGANISM: Artificial Sequence
<220> FEATURE:
<223> OTHER INFORMATION: SAP-K humanised VL variant L0 amino acid sequence

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asn Ser Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Cys Asn Asn Tyr Pro Phe
                85                  90                  95

Thr Phe Gly Gln Gly Thr Lys Leu Glu Ile Lys
            100                 105

<210> SEQ ID NO 42
<211> LENGTH: 107
<212> TYPE: PRT
<213> ORGANISM: Artificial Sequence
<220> FEATURE:
<223> OTHER INFORMATION: SAP-K humanised VL variant L1 amino acid sequence

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asn Ser Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Cys Asn Asn Tyr Pro Phe
                85                  90                  95

Thr Phe Gly Gln Gly Thr Lys Leu Glu Ile Lys
            100                 105

<210> SEQ ID NO 43
<211> LENGTH: 204
<212> TYPE: PRT
<213> ORGANISM: Homo sapiens
<220> FEATURE:
<223> OTHER INFORMATION: Homo sapiens SAP amino acid sequence
```

```
<400> SEQUENCE: 43

His Thr Asp Leu Ser Gly Lys Val Phe Val Phe Pro Arg Glu Ser Val
1               5                   10                  15

Thr Asp His Val Asn Leu Ile Thr Pro Leu Glu Lys Pro Leu Gln Asn
                20                  25                  30

Phe Thr Leu Cys Phe Arg Ala Tyr Ser Asp Leu Ser Arg Ala Tyr Ser
            35                  40                  45

Leu Phe Ser Tyr Asn Thr Gln Gly Arg Asp Asn Glu Leu Leu Val Tyr
        50                  55                  60

Lys Glu Arg Val Gly Glu Tyr Ser Leu Tyr Ile Gly Arg His Lys Val
65                  70                  75                  80

Thr Ser Lys Val Ile Glu Lys Phe Pro Ala Pro Val His Ile Cys Val
                85                  90                  95

Ser Trp Glu Ser Ser Gly Ile Ala Glu Phe Trp Ile Asn Gly Thr
            100                 105                 110

Pro Leu Val Lys Lys Gly Leu Arg Gln Gly Tyr Phe Val Glu Ala Gln
        115                 120                 125

Pro Lys Ile Val Leu Gly Gln Glu Gln Asp Ser Tyr Gly Gly Lys Phe
    130                 135                 140

Asp Arg Ser Gln Ser Phe Val Gly Glu Ile Gly Asp Leu Tyr Met Trp
145                 150                 155                 160

Asp Ser Val Leu Pro Pro Glu Asn Ile Leu Ser Ala Tyr Gln Gly Thr
                165                 170                 175

Pro Leu Pro Ala Asn Ile Leu Asp Trp Gln Ala Leu Asn Tyr Glu Ile
            180                 185                 190

Arg Gly Tyr Val Ile Ile Lys Pro Leu Val Trp Val
        195                 200

<210> SEQ ID NO 44
<211> LENGTH: 203
<212> TYPE: PRT
<213> ORGANISM: Mus musculus
<220> FEATURE:
<223> OTHER INFORMATION: Mus musculus SAP amino acid sequence

<400> SEQUENCE: 44

Gln Thr Asp Leu Lys Arg Lys Val Phe Val Phe Pro Arg Glu Ser Glu
1               5                   10                  15

Thr Asp His Val Lys Leu Ile Pro His Leu Glu Lys Pro Leu Gln Asn
                20                  25                  30

Phe Thr Leu Cys Phe Arg Thr Tyr Ser Asp Leu Ser Arg Ser Gln Ser
            35                  40                  45

Leu Phe Ser Tyr Ser Val Lys Gly Arg Asp Asn Glu Leu Leu Ile Tyr
        50                  55                  60

Lys Glu Lys Val Gly Glu Tyr Ser Leu Tyr Ile Gly Gln Ser Lys Val
65                  70                  75                  80

Thr Val Arg Gly Met Glu Glu Tyr Leu Ser Pro Val His Leu Cys Thr
                85                  90                  95

Thr Trp Glu Ser Ser Gly Ile Val Glu Phe Trp Val Asn Gly Lys
            100                 105                 110

Pro Trp Val Lys Lys Ser Leu Gln Arg Glu Tyr Thr Val Lys Ala Pro
        115                 120                 125

Pro Ser Ile Val Leu Gly Gln Glu Gln Asp Asn Tyr Gly Gly Gly Phe
    130                 135                 140

Gln Arg Ser Gln Ser Phe Val Gly Glu Phe Ser Asp Leu Tyr Met Trp
```

```
            145                 150                 155                 160
Asp Tyr Val Leu Thr Pro Gln Asp Ile Leu Phe Val Tyr Arg Asp Ser
                    165                 170                 175
Pro Val Asn Pro Asn Ile Leu Asn Trp Gln Ala Leu Asn Tyr Glu Ile
                    180                 185                 190

Asn Gly Tyr Val Val Ile Arg Pro Arg Val Trp
                    195                 200

<210> SEQ ID NO 45
<211> LENGTH: 1356
<212> TYPE: DNA
<213> ORGANISM: Artificial Sequence
<220> FEATURE:
<223> OTHER INFORMATION: SAP-E VH chimera nucleotide sequence

<400> SEQUENCE: 45
caggcttctc tacagcagtc tgggactgag ctggtgaggt ctggggcctc agtgaagatg      60
tcctgcaagg cttctggctt cacatttgcc acttacaata tgcactggat taagcagaca     120
cccggacagg gcctggaatg gattgggtat atttatcctg agatggtaa tgctaactac     180 aatcagcagt tcaagggcaa ggccacattg actgcagaca catcctccaa cacagcctac    240
atgcagatca gcagcctgac atctgaagac tctgcggtct atttctgtgc aagaggggac    300
tttgattacg acgagggta ctactttgac tcctggggcc agggcacact agtgaccgtg     360
tccagcgcca gcaccaaggg cccagcgtg ttcccctgg ccccagcag caagagcacc       420 agcggcggca cagccgccct gggctgcctg gtgaaggact acttcccga accggtgacc    480 gtgtcctgga cagcggagc cctgaccagc ggcgtgcaca ccttcccgc cgtgctgcag     540 agcagcggcc tgtacagcct gagcagcgtg gtgaccgtgc ccagcagcag cctgggcacc   600
cagacctaca tctgtaacgt gaaccacaag cccagcaaca ccaaggtgga caagaaggtg   660
gagcccaaga gctgtgacaa gaccacacc tgccccccct gccctgcccc cgagctgctg    720
ggaggcccca gcgtgttcct gttcccccc aagcctaagg acaccctgat gatcagcaga    780
acccccgagg tgacctgtgt ggtggtggat gtgagccacg aggaccctga ggtgaagttc    840
aactggtacg tggacggcgt ggaggtgcac aatgccaaga ccaagcccag ggaggagcag    900
tacaacagca cctaccgggt ggtgtccgtg ctgaccgtgc tgcaccagga ttggctgaac   960
ggcaaggagt acaagtgtaa ggtgtccaac aaggccctgc ctgccccctat cgagaaaacc   1020 atcagcaagg ccaagggcca gcccagagag ccccaggtgt acaccctgcc cctagcaga    1080 gatgagctga ccaagaacca ggtgtccctg acctgcctgg tgaagggctt ctaccccagc   1140
gacatcgccg tggagtggga gagcaacggc cagcccgaga caactacaa gaccacccc    1200 cctgtgctgg acagcgatgg cagcttcttc ctgtacagca agctgaccgt ggacaagagc   1260
agatggcagc agggcaacgt gttcagctgc tccgtgatgc acgaggccct gcacaatcac   1320
tacacccaga gagcctgag cctgtcccct ggcaag                               1356

<210> SEQ ID NO 46
<211> LENGTH: 642
<212> TYPE: DNA
<213> ORGANISM: Artificial Sequence
<220> FEATURE:
<223> OTHER INFORMATION: SAP-E VL chimera nucleotide sequence

<400> SEQUENCE: 46
gacatccaga tgactcagtc tccagcctcc ctatctgcat ctgtgggaga aactgtcacc      60
```

```
atcacatgtc gagcaagtga gaatatttac agttatttag catggtatca gcagaaacag    120
ggaagatccc ctcagctcct ggtccataat gcaaaaacct tagcagaagg tgtgccatca    180
agggtcagtg gcagtggatc aggcacacac ttttctctga agatcaacgg cctgcagcct    240
gaagattttg ggaattatta ctgtcaacat cattatggtg ctccgctcac gttcggtgct    300
gggaccaagc tggaactgaa acgtacggtg gccgccccca gcgtgttcat cttcccccca    360
agcgatgagc agctgaagag cggcaccgcc agcgtggtgt gtctgctgaa caacttctac    420
ccccgggagg ccaaggtgca gtggaaggtg acaatgccc tgcagagcgg caacagccag     480
gagagcgtga ccgagcagga cagcaaggac tccacctaca gcctgagcag caccctgacc    540
ctgagcaagg ccgactacga aagcacaag gtgtacgcct gtgaggtgac ccaccagggc     600
ctgtccagcc ccgtgaccaa gagcttcaac cggggcgagt gc                       642

<210> SEQ ID NO 47
<211> LENGTH: 1347
<212> TYPE: DNA
<213> ORGANISM: Artificial Sequence
<220> FEATURE:
<223> OTHER INFORMATION: SAP-K VH chimera nucleotide sequence

<400> SEQUENCE: 47
caggtccaac tgcagcagcc tggggctgag ctgataaagc ctggggcttc agtgaagttg     60
tcctgcaagg cttctggcta cactttcacc agctactgga tgcactgggt gaagcagagg    120
cctggacaag gccttgagtg gattggaatg attcatccta atagtgttaa tactaactac    180
aatgagaagt tcaagagtaa ggccacactg actgtagaca atcctccag cacagcctac     240 atgcaactca cagcctgac atctgaggac tctgcggtct attactgtgc aagacggaat     300
gattactact ggtacttcga tgtctggggc acagggacac tagtgaccgt gtccagcgcc    360
agcaccaagg gcccagcgt gttccccctg gcccccagca gcaagagcac cagcggcggc     420
acagccgccc tgggctgcct ggtgaaggac tacttccccg aaccggtgac cgtgtcctgg    480
aacagcggag ccctgaccag cggcgtgcac accttccccg ccgtgctgca gagcagcggc    540
ctgtacagcc tgagcagcgt ggtgaccgtg cccagcagca gctgggcac ccagacctac     600 atctgtaacg tgaaccacaa gcccagcaac accaaggtgg acaagaaggt ggagcccaag    660
agctgtgaca gacccacac ctgccccccc tgccctgccc ccgagctgct gggaggcccc      720
agcgtgttcc tgttcccccc caagcctaag gacaccctga tgatcagcag aaccccgag     780 gtgacctgtg tggtggtgga tgtgagccac gaggaccctg aggtgaagtt caactggtac    840
gtggacggcg tggaggtgca caatgccaag accaagccca gggaggagca gtacaacagc    900
acctaccggg tggtgtccgt gctgaccgtg ctgcaccagg attggctgaa cggcaaggag    960
tacaagtgta aggtgtccaa caaggccctg cctgcccta tcgagaaaac catcagcaag     1020
gccaagggcc agcccagaga gccccaggtg tacaccctgc ccctagcag agatgagctg    1080 accaagaacc aggtgtccct gacctgcctg gtgaagggct tctacccag cgacatcgcc     1140 gtggagtggg agagcaacgg ccagcccgag aacaactaca gaccaccccc cctgtgctg     1200 gacagcgatg gcagcttctt cctgtacagc aagctgaccg tggacaagag cagatggcag    1260
cagggcaacg tgttcagctg ctccgtgatg cacgaggccc tgcacaatca ctacacccag    1320
aagagcctga gcctgtcccc tggcaag                                       1347

<210> SEQ ID NO 48
<211> LENGTH: 642
```

<212> TYPE: DNA
<213> ORGANISM: Artificial Sequence
<220> FEATURE:
<223> OTHER INFORMATION: SAP-K VL chimera nucleotide sequence

<400> SEQUENCE: 48

```
gacattgtga tgacccagtc tcaaaaattc atgtccacat cagtaggaga cagggtcagc      60
gtcacctgca aggccagtca gaatgtgaac tctaatgtag cctggtatca acagaaacca     120
gggcaatctc ctaaagcact gatttactcg gcttcctacc ggtacagtgg agtccctgat     180
cgcttcacag gcagtggatc tgggacagat ttcactctca ccatcaccaa tgtgcagtct     240
gaagacttgg cagagtattt ctgtcagcaa tgtaacaact atccattcac gttcggctcg     300
gggacaaagt tggaaataaa acgtacggtg gccgccccca gcgtgttcat cttccccccc     360
agcgatgagc agctgaagag cggcaccgcc agcgtggtgt gtctgctgaa caacttctac     420
ccccgggagg ccaaggtgca gtggaaggtg gacaatgccc tgcagagcgg caacagccag     480
gagagcgtga ccgagcagga cagcaaggac tccacctaca gcctgagcag cacccctgacc   540
ctgagcaagg ccgactacga gaagcacaag gtgtacgcct gtgaggtgac ccaccagggc     600
ctgtccagcc ccgtgaccaa gagcttcaac cggggcgagt gc                       642
```

<210> SEQ ID NO 49
<211> LENGTH: 294
<212> TYPE: DNA
<213> ORGANISM: Homo sapiens
<220> FEATURE:
<223> OTHER INFORMATION: IGHV1-69 human variable heavy chain germline
      acceptor nucleotide sequence

<400> SEQUENCE: 49

```
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc    120
cctggacaag gcttgagtg gatgggaggg atcatcccta tctttggtac agcaaactac     180
gcacagaagt tccagggcag agtcacgatt accgcggaca atccacgag cacagcctac     240
atggagctga gcagcctgag atctgaggac acggccgtgt attactgtgc gaga           294
```

<210> SEQ ID NO 50
<211> LENGTH: 285
<212> TYPE: DNA
<213> ORGANISM: Homo sapiens
<220> FEATURE:
<223> OTHER INFORMATION: IGHV1-39 human variable heavy chain germline
      acceptor nucleotide sequence

<400> SEQUENCE: 50

```
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccatca     180
aggttcagtg gcagtggatc tgggacagat ttcactctca ccatcagcag tctgcaacct    240
gaagattttg caacttacta ctgtcaacag agttacagta cccct                     285
```

<210> SEQ ID NO 51
<211> LENGTH: 366
<212> TYPE: DNA
<213> ORGANISM: Artificial Sequence
<220> FEATURE:
<223> OTHER INFORMATION: SAP-E humanised heavy chain V region variant H0
      nucleotide sequence non-codon optimised

<400> SEQUENCE: 51

```
caggtgcagc tggtgcagtc tggggctgag gtgaagaagc ctgggtcctc ggtgaaggtc      60
tcctgcaagg cttctggagg caccttcagc acttacaata tgcactgggt gcgacaggcc     120
cctggacaag gcttgagtg gatgggatat atttatcctg agatggtaa tgctaactac       180
aatcagcagt tcaagggcag agtcacgatt accgcggaca atccacgag cacagcctac      240
atggagctga gcagcctgag atctgaggac acggccgtgt attactgtgc gagagggac      300
tttgattacg acggaggta ctactttgac tcctggggcc agggcaccct ggtcaccgtc      360
tcctca                                                                366
```

<210> SEQ ID NO 52
<211> LENGTH: 321
<212> TYPE: DNA
<213> ORGANISM: Artificial Sequence
<220> FEATURE:
<223> OTHER INFORMATION: SAP-E humanised light chain V region variant L0 nucleotide sequence non-codon optimised

<400> SEQUENCE: 52

```
gacatccaga tgacccagtc tccatcctcc ctgtctgcat ctgtaggaga cagagtcacc      60
atcacttgcc gagcaagtga gaatatttac agttatttag catggtatca gcagaaacca    120
gggaaagccc ctaagctcct gatctataat gcaaaaacct agcagaagg ggtcccatca     180
aggttcagtg gcagtggatc tgggacagat ttcactctca ccatcagcag tctgcaacct    240
gaagattttg caacttacta ctgtcaacat cattatggtg ctccgctcac gtttggccag    300
gggaccaagc tggagatcaa a                                               321
```

<210> SEQ ID NO 53
<211> LENGTH: 366
<212> TYPE: DNA
<213> ORGANISM: Artificial Sequence
<220> FEATURE:
<223> OTHER INFORMATION: SAP-E humanised heavy chain V region variant H0 nucleotide sequence (codon optimised)

<400> SEQUENCE: 53

```
caggtgcagc tggtgcagag cggcgccgag gtgaagaaac ccggcagcag cgtgaaggtg      60
agctgcaagg ctagcggggg caccttctcc acctacaaca tgcactgggt caggcaggca    120
cccggccagg gcctggagtg gatgggctat atctacccg gcgacggcaa cgccaactac      180
aaccagcagt tcaagggcag ggtgaccatc accgccgaca gagcaccag caccgcctac     240
atggaactga gcagcctgag gagcgaggat accgccgtgt actactgcgc caggggcgac    300
ttcgactacg acggcggcta ctacttcgac agctggggac agggcacact agtgaccgtg    360
tccagc                                                                366
```

<210> SEQ ID NO 54
<211> LENGTH: 366
<212> TYPE: DNA
<213> ORGANISM: Artificial Sequence
<220> FEATURE:
<223> OTHER INFORMATION: SAP-E humanised heavy chain V region variant H1 nucleotide sequence (codon optimised)

<400> SEQUENCE: 54

```
caggtgcagc tggtgcagag cggcgccgag gtgaagaaac ccggcagcag cgtgaaggtg      60
agctgcaagg ctagcggggt cacctttgcc acctacaaca tgcactgggt caggcaggca    120
```

```
cccggccagg gcctggagtg gatgggctat atctaccccg cgacggcaa cgccaactac    180 aaccagcagt tcaagggcag ggtgaccatc accgccgaca gagcaccag caccgcctac    240 atggaactga gcagcctgag gagcgaggat accgccgtgt actactgcgc caggggcgac    300
ttcgactacg acggcggcta ctacttcgac agctggggac agggcacact agtgaccgtg    360
tccagc                                                               366

<210> SEQ ID NO 55
<211> LENGTH: 366
<212> TYPE: DNA
<213> ORGANISM: Artificial Sequence
<220> FEATURE:
<223> OTHER INFORMATION: SAP-E humanised heavy chain V region variant H2
      nucleotide sequence (codon optimised)

<400> SEQUENCE: 55
caggcgcagc tggtgcagag cggcgccgag gtgaagaaac ccggcagcag cgtgaaggtg    60
agctgcaagg ctagcgggtt caccttcgcc acctacaaca tgcactgggt caggcaggca    120
cccggccagg gcctggagtg gatgggctat atctaccccg cgacggcaa cgccaactac    180 aaccagcagt tcaagggcag ggtgaccatc accgccgaca gagcaccag caccgcctac    240 atggaactga gcagcctgag gagcgaggat accgccgtgt actactgcgc caggggcgac    300
ttcgactacg acggcggcta ctacttcgac agctggggac agggcacact agtgaccgtg    360
tccagc                                                               366

<210> SEQ ID NO 56
<211> LENGTH: 366
<212> TYPE: DNA
<213> ORGANISM: Artificial Sequence
<220> FEATURE:
<223> OTHER INFORMATION: SAP-E humanised heavy chain V region variant H3
      nucleotide sequence (codon optimised)

<400> SEQUENCE: 56
caggtgcagc tggtgcagag cggcgccgag gtgaagaaac ccggcagcag cgtgaaggtg    60
agctgcaagg ctagcgggtt caccttcgcc acctacaaca tgcactgggt caggcaggca    120
cccggccagg gcctggagtg gatcggctat atctaccccg cgacggcaa cgccaactac    180 aaccagcagt tcaagggcag ggccaccatc accgccgaca gagcaccag caccgcctac    240 atggaactga gcagcctgag gagcgaggat accgccgtgt actactgcgc caggggcgac    300
ttcgactacg acggcggcta ctacttcgac agctggggac agggcacact agtgaccgtg    360
tccagc                                                               366

<210> SEQ ID NO 57
<211> LENGTH: 366
<212> TYPE: DNA
<213> ORGANISM: Artificial Sequence
<220> FEATURE:
<223> OTHER INFORMATION: SAP-E humanised heavy chain V region variant H4
      nucleotide sequence (codon optimised)

<400> SEQUENCE: 57
caggtgcagc tggtgcagag cggcgccgag gtgaagaaac ccggcagcag cgtgaaggtg    60
agctgcaagg ctagcgggtt caccttcgcc acctacaaca tgcactgggt caggcaggca    120
cccggccagg gcctggagtg gatcggctat atctaccccg cgacggcaa cgccaactac    180 aaccagcagt tcaagggcag ggccaccctg accgccgaca ccagcaccag caccgcctac    240
```

```
atggaactga gcagcctgag gagcgaggat accgccgtgt acttctgcgc caggggcgac      300
ttcgactacg acggcggcta ctacttcgac agctggggac agggcacact agtgaccgtg      360
tccagc                                                                 366
```

<210> SEQ ID NO 58
<211> LENGTH: 321
<212> TYPE: DNA
<213> ORGANISM: Artificial Sequence
<220> FEATURE:
<223> OTHER INFORMATION: SAP-E humanised light chain V region variant L0
      nucleotide sequence (codon optimised)

<400> SEQUENCE: 58

```
gacatccaga tgacccagag ccccagctca ctgagcgcca gcgtgggcga cagggtgacc       60
attacctgca gggcctccga gaacatctac agctacctgg cctggtacca gcagaagccc      120
ggcaaggccc ccaagctgct gatctacaac gccaagaccc tcgccgaggg cgtccctagc      180
aggttctctg gaagcggcag cggcaccgac ttcaccctga ccatcagcag cctgcagccc      240
gaggacttcg ccacctatta ctgccagcac cactacggcg ccccccctga ctttggccag      300
ggcaccaaac tggagatcaa g                                                321
```

<210> SEQ ID NO 59
<211> LENGTH: 321
<212> TYPE: DNA
<213> ORGANISM: Artificial Sequence
<220> FEATURE:
<223> OTHER INFORMATION: SAP-E humanised light chain V region variant L1
      nucleotide sequence (codon optimised)

<400> SEQUENCE: 59

```
gacatccaga tgacccagag ccccagctca ctgagcgcca gcgtgggcga cagggtgacc       60
attacctgca gggcctccga gaacatctac agctacctgg cctggtacca gcagaagccc      120
ggcaaggccc ccaagctgct gatccacaac gccaagaccc tcgccgaggg cgtccctagc      180
aggttctctg gaagcggcag cggcaccgac ttcaccctga ccatcagcag cctgcagccc      240
gaggacttcg ccacctatta ctgccagcac cactacggcg ccccccctga ctttggccag      300
ggcaccaaac tggagatcaa g                                                321
```

<210> SEQ ID NO 60
<211> LENGTH: 321
<212> TYPE: DNA
<213> ORGANISM: Artificial Sequence
<220> FEATURE:
<223> OTHER INFORMATION: SAP-E humanised light chain V region variant L2
      nucleotide sequence (codon optimised)

<400> SEQUENCE: 60

```
gacatccaga tgacccagag ccccagctca ctgagcgcca gcgtgggcga cagggtgacc       60
attacctgca gggcctccga gaacatctac agctacctgg cctggtacca gcagaagccc      120
ggcaaggccc ccaagctgct ggtgcacaac gccaagaccc tcgccgaggg cgtccctagc      180
aggttctctg gaagcggcag cggcaccgac ttcaccctga ccatcagcag cctgcagccc      240
gaggacttcg ccacctatta ctgccagcac cactacggcg ccccccctga ctttggccag      300
ggcaccaaac tggagatcaa g                                                321
```

<210> SEQ ID NO 61
<211> LENGTH: 1356

<212> TYPE: DNA
<213> ORGANISM: Artificial Sequence
<220> FEATURE:
<223> OTHER INFORMATION: SAP-E humanised heavy chain H1 full mature
      nucleotide sequence (codon optimised)

<400> SEQUENCE: 61

```
caggtgcagc tggtgcagag cggcgccgag gtgaagaaac ccggcagcag cgtgaaggtg     60
agctgcaagg ctagcgggtt caccttcgcc acctacaaca tgcactgggt caggcaggca    120
cccggccagg gcctggagtg gatgggctat atctacccccg cgacggcaa cgccaactac    180
aaccagcagt tcaagggcag ggtgaccatc accgccgaca gagcaccag caccgcctac    240
atggaactga gcagcctgag gagcgaggat accgccgtgt actactgcgc caggggcgac    300
ttcgactacg acggcggcta ctacttcgac agctggggac agggcacact agtgaccgtg    360
tccagcgcca gcaccaaggg ccccagcgtg ttccccctgg ccccagcag caagagcacc    420
agcggcggca cagccgccct gggctgcctg gtgaaggact acttccccga accggtgacc    480
gtgtcctgga acagcggagc cctgaccagc ggcgtgcaca ccttcccgc cgtgctgcag    540
agcagcggcc tgtacagcct gagcagcgtg gtgaccgtgc ccagcagcag cctgggcacc    600
cagacctaca tctgtaacgt gaaccacaag cccagcaaca ccaaggtgga caagaaggtg    660
gagcccaaga gctgtgacaa gccccacacc tgccccccct gccctgcccc cgagctgctg    720
ggaggccccca gcgtgttcct gttccccccc aagcctaagg acaccctgat gatcagcaga    780
acccccgagg tgacctgtgt ggtggtggat gtgagccacg aggaccctga ggtgaagttc    840
aactggtacg tggacggcgt ggaggtgcac aatgccaaga ccaagcccag ggaggagcag    900
tacaacagca cctaccgggt ggtgtccgtg ctgaccgtgc tgcaccagga ttggctgaac    960
ggcaaggagt acaagtgtaa ggtgtccaac aaggcccctgc ctgcccctat cgagaaaacc   1020
atcagcaagg ccaagggcca gccagagag ccccaggtgt acaccctgcc cctagcaga    1080
gatgagctga ccaagaacca ggtgtccctg acctgcctgg tgaagggctt ctaccccagc   1140
gacatcgccg tggagtggga gagcaacggc cagcccgaga caactacaa gaccaccccc   1200
cctgtgctgg acagcgatgg cagcttcttc ctgtacagca agctgaccgt ggacaagagc   1260
agatggcagc agggcaacgt gttcagctgc tccgtgatgc acgaggccct gcacaatcac   1320
tacacccaga gagcctgag cctgtccccct ggcaag                             1356
```

<210> SEQ ID NO 62
<211> LENGTH: 444
<212> TYPE: PRT
<213> ORGANISM: Artificial Sequence
<220> FEATURE:
<223> OTHER INFORMATION: SAP-E humanised heavy chain H1 full mature amino
      acid sequence

<400> SEQUENCE: 62

```
Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ala Thr Tyr
            20                  25                  30

Asn Met His Trp Val Arg Gln Ala Pro Gly Gln Gly Leu Glu Trp Met
        35                  40                  45

Gly Tyr Ile Tyr Pro Gly Asp Gly Asn Ala Asn Tyr Asn Gln Gln Phe
    50                  55                  60

Lys Gly Arg Val Thr Ile Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Arg Asp Phe Asp Tyr Asp Gly Gly Tyr Tyr Phe Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Tyr Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440

<210> SEQ ID NO 63
<211> LENGTH: 642
<212> TYPE: DNA
<213> ORGANISM: Artificial Sequence
<220> FEATURE:
<223> OTHER INFORMATION: SAP-E humanised light chain L1 full mature
      nucleotide sequence
      (codon optimised)
```

<400> SEQUENCE: 63

```
gacatccaga tgacccagag ccccagctca ctgagcgcca gcgtgggcga cagggtgacc       60
attacctgca gggcctccga gaacatctac agctacctgg cctggtacca gcagaagccc      120
ggcaaggccc ccaagctgct gatccacaac gccaagaccc tcgccgaggg cgtccctagc      180
aggttctctg gaagcggcag cggcaccgac ttcaccctga ccatcagcag cctgcagccc      240
gaggacttcg ccacctatta ctgccagcac cactacggcg ccccctgac ctttggccag       300
ggcaccaaac tggagatcaa gcgtacggtg gccgccccca gcgtgttcat cttccccccc      360
agcgatgagc agctgaagag cggcaccgcc agcgtggtgt gtctgctgaa caacttctac      420
ccccgggagg ccaaggtgca gtggaaggtg gacaatgccc tgcagagcgg caacagccag      480
gagagcgtga ccgagcagga cagcaaggac tccacctaca gcctgagcag cacccctgacc    540
ctgagcaagg ccgactacga gaagcacaag gtgtacgcct gtgaggtgac ccaccagggc     600
ctgtccagcc ccgtgaccaa gagcttcaac cggggcgagt gc                        642
```

<210> SEQ ID NO 64
<211> LENGTH: 214
<212> TYPE: PRT
<213> ORGANISM: Artificial Sequence
<220> FEATURE:
<223> OTHER INFORMATION: SAP-E humanised light chain L1 full mature amino acid sequence

<400> SEQUENCE: 64

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

His Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Ala Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 65
<211> LENGTH: 357
<212> TYPE: DNA
<213> ORGANISM: Artificial Sequence
<220> FEATURE:
<223> OTHER INFORMATION: SAP-K humanised heavy chain V region variant H0
      nucleotide sequence non-codon optimised

<400> SEQUENCE: 65
caggtgcagc tggtgcagtc tggggctgag gtgaagaagc ctgggtcctc ggtgaaggtc        60
tcctgcaagg cttctggagg caccttcagc agctactgga tgcactgggt gcgacaggcc       120
cctggacaag gcttgagtg gatgggaatg attcatccta atagtgttaa tactaactac       180
aatgagaagt tcaagagtag agtcacgatt accgcggaca aatccacgag cacagcctac       240
atggagctga gcagcctgag atctgaggac acggccgtgt attactgtgc gagacggaat       300
gattactact ggtacttcga tgtctggggc cagggcaccc tggtcaccgt ctcctca          357

<210> SEQ ID NO 66
<211> LENGTH: 321
<212> TYPE: DNA
<213> ORGANISM: Artificial Sequence
<220> FEATURE:
<223> OTHER INFORMATION: SAP-K humanised light chain V region variant L0
      nucleotide sequence non-codon optimised

<400> SEQUENCE: 66
gacatccaga tgacccagtc tccatcctcc ctgtctgcat ctgtaggaga cagagtcacc        60
atcacttgca aggccagtca gaatgtgaac tctaatgtag cctggtatca gcagaaacca       120
gggaaagccc ctaagctcct gatctattcg gcttcctacc ggtacagtgg ggtcccatca       180
aggttcagtg gcagtggatc tgggacagat ttcactctca ccatcagcag tctgcaacct       240
gaagattttg caacttacta ctgtcagcaa tgtaacaact atccattcac gtttggccag       300
gggaccaagc tggagatcaa a                                                 321

<210> SEQ ID NO 67
<211> LENGTH: 357
<212> TYPE: DNA
<213> ORGANISM: Artificial Sequence
<220> FEATURE:
<223> OTHER INFORMATION: SAP-K humanised heavy chain V region variant H0
      nucleotide sequence (codon optimised)

<400> SEQUENCE: 67
caggtgcagc tggtgcagag cggcgccgaa gtgaagaagc ccggcagcag cgtgaaagtg        60
agctgcaagg ccagcggcgg aaccttcagc agctactgga tgcactgggt gaggcaggca       120
cccggccagg gcctggagtg gatgggcatg atccacccca acagcgtgaa caccaactac       180
aacgagaagt tcaagagcag agtgaccatc accgccgaca gagcaccag caccgcctat       240 atggagctga gctctctgag gagcgaggat accgccgtgt actactgcgc caggaggaac       300
gactactact ggtacttcga cgtctggggc cagggcacac tagtgaccgt gtccagc          357

<210> SEQ ID NO 68
<211> LENGTH: 357
<212> TYPE: DNA
<213> ORGANISM: Artificial Sequence
<220> FEATURE:
<223> OTHER INFORMATION: SAP-K humanised heavy chain V region variant H1
      nucleotide sequence (codon optimised)

<400> SEQUENCE: 68

```
caggtgcagc tggtgcagag cggcgccgaa gtgaagaagc ccggcagcag cgtgaaagtg    60
agctgcaagg ccagcggcta caccttcacc agctactgga tgcactgggt gaggcaggca   120
cccggccagg gcctggagtg gatgggcatg atccacccca acagcgtgaa caccaactac   180
aacgagaagt tcaagagcag agtgaccatc accgccgaca gagcaccag caccgcctat   240 atggagctga gctctctgag gagcgaggat accgccgtgt actactgcgc caggaggaac   300
gactactact ggtacttcga cgtctgggc cagggcacac tagtgaccgt gtccagc      357
```

<210> SEQ ID NO 69
<211> LENGTH: 357
<212> TYPE: DNA
<213> ORGANISM: Artificial Sequence
<220> FEATURE:
<223> OTHER INFORMATION: SAP-K humanised heavy chain V region variant H2 nucleotide sequence (codon optimised)

<400> SEQUENCE: 69

```
caggtgcagc tggtgcagag cggcgccgaa gtgaagaagc ccggcagcag cgtgaaagtg    60
agctgcaagg ccagcggcta caccttcacc agctactgga tgcactgggt gaggcaggca   120
cccggccagg gcctggagtg gatcggcatg atccacccca acagcgtgaa caccaactac   180
aacgagaagt tcaagagcag agccaccatc accgccgaca gagcaccag caccgcctat   240 atggagctga gctctctgag gagcgaggat accgccgtgt actactgcgc caggaggaac   300
gactactact ggtacttcga cgtctgggc cagggcacac tagtgaccgt gtccagc      357
```

<210> SEQ ID NO 70
<211> LENGTH: 357
<212> TYPE: DNA
<213> ORGANISM: Artificial Sequence
<220> FEATURE:
<223> OTHER INFORMATION: SAP-K humanised heavy chain V region variant H3 nucleotide sequence (codon optimised)

<400> SEQUENCE: 70

```
caggtgcagc tggtgcagag cggcgccgaa gtgaagaagc ccggcagcag cgtgaaagtg    60
agctgcaagg ccagcggcta caccttcacc agctactgga tgcactgggt gaggcaggca   120
cccggccagg gcctggagtg gatcggcatg atccacccca acagcgtgaa caccaactac   180
aacgagaagt tcaagagcag agccaccctg accgtggaca gagcaccag caccgcctat   240 atggagctga gctctctgag gagcgaggat accgccgtgt actactgcgc caggaggaac   300
gactactact ggtacttcga cgtctgggc cagggcacac tagtgaccgt gtccagc      357
```

<210> SEQ ID NO 71
<211> LENGTH: 321
<212> TYPE: DNA
<213> ORGANISM: Artificial Sequence
<220> FEATURE:
<223> OTHER INFORMATION: SAP-K humanised light chain V region variant L0 nucleotide sequence (codon optimised)

<400> SEQUENCE: 71

```
gacatccaga tgacccagag cccctcttca ctgagcgcta gcgtgggcga cagggtgacc    60
atcacctgca aggccagcca gaacgtgaac agcaacgtgg cctggtacca gcagaagccc   120
ggcaaagccc ccaagctcct gatctacagc gccagctaca gatatagcgg cgtgcctagc   180
aggtttagcg gcagcggaag cgggaccgat ttcaccctga ccatcagcag cctgcagccc   240
gaggacttcg ccacttacta ctgccagcag tgcaacaact accccttcac cttcggccag   300
```

```
ggcaccaagc tggagatcaa g                                            321
```

<210> SEQ ID NO 72
<211> LENGTH: 321
<212> TYPE: DNA
<213> ORGANISM: Artificial Sequence
<220> FEATURE:
<223> OTHER INFORMATION: SAP-K humanised light chain V region variant L1
      nucleotide sequence (codon optimised)

<400> SEQUENCE: 72

```
gacatccaga tgacccagag cccctcttca ctgagcgcta gcgtgggcga cagggtgacc    60
atcacctgca aggccagcca gaacgtgaac agcaacgtgg cctggtacca gcagaagccc   120
ggcaaagccc ccaaggccct gatctacagc gccagctaca gatatagcgg cgtgcctagc   180
aggtttagcg gcagcggaag cgggaccgat ttcaccctga ccatcagcag cctgcagccc   240
gaggacttcg ccacttacta ctgccagcag tgcaacaact acccccttca cttcggccag   300
ggcaccaagc tggagatcaa g                                            321
```

<210> SEQ ID NO 73
<211> LENGTH: 321
<212> TYPE: DNA
<213> ORGANISM: Artificial Sequence
<220> FEATURE:
<223> OTHER INFORMATION: SAP-K humanised light chain V region variant L0
      91A nucleotide sequence (codon optimised)

<400> SEQUENCE: 73

```
gacatccaga tgacccagag cccctcttca ctgagcgcta gcgtgggcga cagggtgacc    60
atcacctgca aggccagcca gaacgtgaac agcaacgtgg cctggtacca gcagaagccc   120
ggcaaagccc ccaagctcct gatctacagc gccagctaca gatatagcgg cgtgcctagc   180
aggtttagcg gcagcggaag cgggaccgat ttcaccctga ccatcagcag cctgcagccc   240
gaggacttcg ccacttacta ctgccagcag gcgaacaact acccccttca cttcggccag   300
ggcaccaagc tggagatcaa g                                            321
```

<210> SEQ ID NO 74
<211> LENGTH: 107
<212> TYPE: PRT
<213> ORGANISM: Artificial Sequence
<220> FEATURE:
<223> OTHER INFORMATION: SAP-K humanised light chain V region variant L0
      91A amino acid sequence

<400> SEQUENCE: 74

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asn Ser Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Tyr Pro Phe
                85                  90                  95

Thr Phe Gly Gln Gly Thr Lys Leu Glu Ile Lys
                100                 105
```

<210> SEQ ID NO 75
<211> LENGTH: 1347
<212> TYPE: DNA
<213> ORGANISM: Artificial Sequence
<220> FEATURE:
<223> OTHER INFORMATION: SAP-K humanised H3 heavy chain nucleotide sequence
      (codon optimised)

<400> SEQUENCE: 75

```
caggtgcagc tggtgcagag cggcgccgaa gtgaagaagc ccggcagcag cgtgaaagtg      60
agctgcaagg ccagcggcta caccttcacc agctactgga tgcactgggt gaggcaggca     120
cccggccagg gcctggagtg gatcggcatg atccacccca cagcgtgaa caccaactac     180
aacgagaagt tcaagagcag agccaccctg accgtggaca gagccaccag caccgcctat     240
atggagctga gctctctgag gagcgaggat accgccgtgt actactgcgc caggaggaac     300
gactactact ggtacttcga cgtctggggc cagggcacac tagtgaccgt gtccagcgcc     360
agcaccaagg gccccagcgt gttccccctg gcccccagca gcaagagcac cagcggcggc     420
acagccgccc tgggctgcct ggtgaaggac tacttccccg aaccggtgac cgtgtcctgg     480
aacagcggag ccctgaccag cggcgtgcac accttcccg ccgtgctgca gagcagcggc     540
ctgtacagcc tgagcagcgt ggtgaccgtg cccagcagca gcctgggcac ccagacctac     600
atctgtaacg tgaaccacaa gcccagcaac accaaggtgg acaagaaggt ggagcccaag     660
agctgtgaca gacccacac ctgcccccc tgccctgccc ccgagctgct gggaggcccc      720
agcgtgttcc tgttcccccc caagcctaag gacaccctga tgatcagcag aaccccgag     780
gtgacctgtg tggtggtgga tgtgagccac gaggaccctg aggtgaagtt caactggtac     840
gtggacggcg tggaggtgca caatgccaag accaagccca gggaggagca gtacaacagc     900
acctaccggg tggtgtccgt gctgaccgtg ctgcaccagg attggctgaa cggcaaggag     960
tacaagtgta aggtgtccaa caaggccctg cctgcccta tcgagaaaac catcagcaag    1020
gccaagggcc agcccagaga gccccaggtg tacaccctgc ccctagcag agatgagctg    1080
accaagaacc aggtgtccct gacctgcctg gtgaagggct tctacccag cgacatcgcc    1140
gtggagtggg agagcaacgg ccagcccgag aacaactaca agaccacccc ccctgtgctg    1200
gacagcgatg gcagcttctt cctgtacagc aagctgaccg tggacaagag cagatggcag    1260
cagggcaacg tgttcagctg ctccgtgatg cacgaggccc tgcacaatca ctacacccag    1320
aagagcctga gcctgtcccc tggcaag                                       1347
```

<210> SEQ ID NO 76
<211> LENGTH: 443
<212> TYPE: PRT
<213> ORGANISM: Artificial Sequence
<220> FEATURE:
<223> OTHER INFORMATION: SAP-K humanised H3 heavy chain amino acid sequence

<400> SEQUENCE: 76

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Met Ile His Pro Asn Ser Val Asn Thr Asn Tyr Asn Glu Lys Phe
    50                  55                  60

Lys Ser Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Arg Asn Asp Tyr Tyr Trp Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Tyr Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Lys Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 77
<211> LENGTH: 642
<212> TYPE: DNA
<213> ORGANISM: Artificial Sequence
<220> FEATURE:

<223> OTHER INFORMATION: SAP-K humanised L0 light chain nucleotide sequence
(codon optimised)

<400> SEQUENCE: 77

```
gacatccaga tgacccagag cccctcttca ctgagcgcta gcgtgggcga cagggtgacc      60
atcacctgca aggccagcca gaacgtgaac agcaacgtgg cctggtacca gcagaagccc     120
ggcaaagccc ccaagctcct gatctacagc gccagctaca gatatagcgg cgtgcctagc     180
aggtttagcg gcagcggaag cgggaccgat ttcaccctga ccatcagcag cctgcagccc     240
gaggacttcg ccacttacta ctgccagcag tgcaacaact accccttcac cttcggccag     300
ggcaccaagc tggagatcaa agtacggtg gccgccccca gcgtgttcat cttccccccc     360
agcgatgagc agctgaagag cggcaccgcc agcgtggtgt gtctgctgaa caacttctac     420
ccccgggagg ccaaggtgca gtggaaggtg gacaatgccc tgcagagcgg caacagccag     480
gagagcgtga ccgagcagga cagcaaggac tccacctaca gcctgagcag caccctgacc     540
ctgagcaagg ccgactacga aaagcacaag gtgtacgcct gtgaggtgac ccaccagggc     600
ctgtccagcc ccgtgaccaa gagcttcaac cggggcgagt gc                        642
```

<210> SEQ ID NO 78
<211> LENGTH: 214
<212> TYPE: PRT
<213> ORGANISM: Artificial Sequence
<220> FEATURE:
<223> OTHER INFORMATION: SAP-K humanised L0 light chain amino acid sequence

<400> SEQUENCE: 78

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asn Ser Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Cys Asn Asn Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 79
<211> LENGTH: 19
<212> TYPE: PRT
<213> ORGANISM: Mus musculus
<220> FEATURE:
<223> OTHER INFORMATION: Signal sequence for immunoglobulin chains

<400> SEQUENCE: 79

Met Gly Trp Ser Cys Ile Ile Leu Phe Leu Val Ala Thr Ala Thr Gly
1               5                   10                  15

Val His Ser
```